US008182990B2

(12) United States Patent
Mashima

(10) Patent No.: US 8,182,990 B2

(45) Date of Patent: May 22, 2012

(54) METHOD FOR DIAGNOSING OR PREDICTING SUSCEPTIBILITY TO OPTIC NEUROPATHY

(75) Inventor: Yukihiko Mashima, Tokyo-to (JP)

(73) Assignee: Rusk Intellectual Reserve AG, Zug (CH)

( * ) Notice: Subject to any disclaimer, the term of this patent is extended or adjusted under 35 U.S.C. 154(b) by 749 days.

(21) Appl. No.: 10/593,103

(22) PCT Filed: Mar. 18, 2005

(86) PCT No.: PCT/JP2005/005601

§ 371 (c)(1),
(2), (4) Date: Sep. 15, 2006

(87) PCT Pub. No.: WO2005/090602

PCT Pub. Date: Sep. 29, 2005

(65) Prior Publication Data

US 2008/0221050 A1 Sep. 11, 2008

Related U.S. Application Data

(60) Provisional application No. 60/553,986, filed on Mar. 18, 2004, provisional application No. 60/604,704, filed on Aug. 27, 2004, provisional application No. 60/607,359, filed on Sep. 7, 2004.

(51) Int. Cl.
*C12Q 1/68* (2006.01)
*C07H 21/02* (2006.01)

(52) U.S. Cl. ...................................... 435/6.11; 536/23.1

(58) Field of Classification Search ........................ None
See application file for complete search history.

(56) References Cited

FOREIGN PATENT DOCUMENTS

| | | | |
|---|---|---|---|
| WO | WO 02/22881 | A | 3/2002 |
| WO | WO 02/24747 | A2 | 3/2002 |

OTHER PUBLICATIONS

Brown, Michael et al. Clustering of Caucasian Leber hereditary optic neuropathy patients containing the 11778 or 14484 mutations on an mtDNA lingeage. 1997. American Journal of Human Genetics. vol. 60 pp. 381-387.*

Ishikawa, Karin et al. Novel MYOC gene mutation Phe369Leu is Japanese patients with primary open angle claucoma detected by denaturing high performance liquid chromatography. 2004 Journal of Glaucoma vol. 13 No. 6 pp. 466-471.*

Umeda, T et al. Optineurin gene polymoprhisms in Japanese glaucoma pateints and normal individuals. 2003. Investigative Ophthalmology and Visual Science. 2003 vol. 44 E-Abstract 1111.*

Mukhopadhyay, Arijit et al. Bioinformatic approaches for identification and characterization of olfactomedin related genes with a potential role in pathogenesis of ocular disorders. 2004. Molecular Vision vol. 10 pp. 304-314.*

Mukhopadhyay, Arijit et al. Mutations in MYOC gene of Indian primary open angle glaucoma patients. 2002 Molecular Vision vol. 8 pp. 442-448.*

Lucentini, Jack. Gene Association Studies Typically Wrong. 2004. The Scientist vol. 18, pp. 1-3.*

Tabor, Holly et al. Candidate gene approaches for studying complex genetic traits: practical considerations. Nature Reviews Genetics. 2002 vol. 3 pp. 1-7.*

Wacholder, Sholom et al. Assessing the probability that a positive report is false: an approach for molecular epidemiology studies. Journal of the National Cancer Institute. 2004. vol. 96 pp. 434-442.*

Thisted What is a P value? The University of Chicago 1998 http://www.stat.uchicago.edu/~thisted.*

Fingert, John et al. Analysis of myocilin mutations in 1703 glaucoma patients from five different populations. Human Molecular Genetics 1999 vol. 8 No. 5 pp. 899-905.*

Michael D. Brown, et al, "Phylogenetic Analysis of Leber's Hereditary Optic Neuropathy Mitochondrial DNA's Indicates Multiples Independent Occurrences of the Common Mutations", Human Mutation, vol. 6, No. 4, 1995, pp. 311-325, XP009054854, ISSN: 1059-7794.

D. A. Hollander, et al, "Outflow Pathway Anomalies Associated With Multiple CYP1B1 Mutations in Congenital Glaucoma", ARVO Annual Meeting Abstract Search and Program Planner, vol. 2003, 2003, Page Abstract No. 1117, XP009054897 & Annual Meeting of the Association for Research in Vision and Ophthalmology; Fort Lauderdale, FL, USA; May 4-8, 2003.

X. Bu, et al, "X Chromosome-Linked and Mitochondrial Gene Control of Leber Hereditary Optic Neuropathy Evidence From Segregation Analysis for Dependence on X Chromosome Inactivation", Proceedings of the National Academy of Sciences of the United States of America, vol. 88, No. 18, 1991, pp. 8198-8202, XP002347836.

P. F. Chinnery, et al, "The Mitochondrial ND6 Gene Is a Hot Spot for Mutations That Cause Leber's Hereditary Optic Neuropathy", Brain, vol. 124, No. 1, Jan. 2001, pp. 209-218, XP002347837, ISSN: 0006-8950.

Mashima, Yukihiko et al. "Optic disc excavation in the atrophic state of Leber's hereditary optic neuropathy: comparison with normal tension glaucoma", Arch Clinical Exp Ophthalmology, vol. 241, pp. 75-80, Jan. 25, 2003.

Brown, Michael et al. "Spectrum of Mitochondrial DNA Mutations in Leber's Hereditary Optic Neuropathy", Clinical Neuroscience, vol. 2, pp. 138-145, 1994.

Mackey, David et al., "Primary Pathogenic mtDNA Mutations in Multigenreation Pedigrees with Leber Hereditary Optic Neuropathy", The American Society of Human Genetics, 59, pp. 481-485, 1996.

Brierley, Elizabeth, "Normal Respiratory Chain Function in Patients With Low-tension Glaucoma", Arch Opthalmology; vol. 114, pp. 142-146, Feb. 1996.

Opial, Danielle et al., "Leber's hereditary optic neuropathy mitochondrial DNA mutations in normal-tension glaucoma", Graefe's Arch Clin. Exp. Ophthalmology; vol. 239, pp. 437-440, Jun. 22, 2001.

(Continued)

*Primary Examiner* — Amanda Shaw
(74) *Attorney, Agent, or Firm* — Sughrue Mion, PLLC

(57) ABSTRACT

Disclosed is a set of genetic polymorphisms linked to optic neuropathy including glaucoma and Leber's disease. Those polymorphisms are useful for diagnosing and predicting susceptibility to optic neuropathy.

8 Claims, 5 Drawing Sheets

OTHER PUBLICATIONS

Oostra, R.J., "Leber's hereditary optic neuropathy: correlations between mitochondrial genotype and visual outcome", J Med Genet, vol. 31, pp. 280-286, Oct. 14, 1993.

Riordan-Eva, P. et al., "The clinical features of Leber's hereditary optic neuropathy defined by the presence of the a pathogenic mitochondrial DNA mutation", Brain, vol. 118, pp. 319-337, 1995.

Mashima, Yukihiko et al., "Spectrum of pathogenic mitochondrial DNA mutations and clinical features in Japanese families with Leber's hereditary optic neuropathy", Current Eye Research, vol. 17, pp. 403-408, Jan. 1998.

Stone, Edwin et al., "Visual Recovery in Patients with Leber's Hereditary Optic Neuopathy and the 11778 Mutation", Journal of Clinical Neuro-opthalmology, vol. 12, pp. 10-14, 1992.

Zhu, Danping et al., "Mitochondrial DNA Mutation and Heteroplasmy in Type I Leber Hereditary Optic Neuropathy", American Journal of Medical Genetics, vol. 42, pp. 173-179, Apr. 1992.

Salmaggi, Andrea et al, "Remarkable Recovery of Visual Function in a Patient with Leber's Optic Neuropathy and Multiple Mutations of Mitochondrial DNA", Intern. Journal Neuroscience, vol. 77, pp. 261-266, 1994.

Oostra, R.J. et al., "On the many faces of Leber hereditary optic neuropathy", Clinical Genetics, vol. 51, pp. 388-393, Mar. 21, 1997.

Mashima, Yukihiko et al., "Macular Nerve Fibers Temporal to Fovea may have a Greater Potential to Recover Function in Patients with Leber's Hereditary Optic Neuropathy", Journal of Ophthalmology, vol. 46 pp. 660-667 2002.

Man, P. Y. W. et al. "Leber hereditary optic neuropathy" Journal of Medical Genetics, vol. 39 pp. 162-169 2002.

Chalmers, R. M. et al., "Evidence against an X-Linked Visual Loss Susceptibility Locus in Leber Hereditary Optic Neuropathy", American Journal of Human Genetics, vol. 59 pp. 103-108 1996.

Pegoraro, Elena et al., "X-Inactivation Pattern in Multiple Tissues From Two Leber's Hereditary Optic Neuropathy (LHON) Patients", American Journal of Medical Genetics, vol. 119A pp. 37-40 2003.

Brown, Michael et al., "Clustering of Caucasain Leber Hereditary Optic Neuropathy Patients Containing the 11778 or 14484 Mutations on an mtDNA Lineage", American Journal of Human Genetics, vol. 60 pp. 381-387 1997.

Torroni, Antonio et al., "Haplotype and Phylogenetic Analysis Suggest That One European-Specific mtDNA Background Plays a Role in the Expression of Leber Hereditary Optic Neuropathy by Increasing the Penetrance of the Primary Mutations 11778 and 14484", American Journal of Human Genetics, vol. 60 pp. 1107-1121 1997.

Smith, P. R. et al., "Smoking and Mitochondrial function: a model for environmental toxins", Quarterly Journal of Medicine, vol. 86 pp. 657-660 1993.

Chalmers, R. M. et al., "A case-control study of Leber's hereditary optic neuropathy", Brain vol. 119 pp. 1481-1486 1996.

Tsao, Kailenn, et al., "Smoking as an actiological factor in a pedigree with Leber's hereditary optic neuropathy", British Journal of Ophthalmology, vol. 83 pp. 577-581 1999.

Kerrison, John et al., "A Case-control Study of Tobacco and Alcohol Consumption in Leber Hereditary Optic Neuropathy", American Journal of Ophthalmology, vol. 130 pp. 803-812 2000.

Qi, Xiaoping et al., "Optic Neuropathy Induced by Reductions in Mitochondrial Superoxide Dismutase", Investigative Ophthalmology & Visual Science, vol. 44 pp. 1088-1096 Mar. 2003.

Danielson, Steven et al., "Cells Bearing Mutations Causing Leber's Hereditary Optic Neuropathy Are Sensitized to Fas-induced Apoptosis", The Journal of Biological Chemistry, vol. 277 No. 8 pp. 5810-5815 Feb. 22, 2002.

Kimura, Katsuaki et al., "Genetic Association of Manganese Superoxide Dismutase With Exodative Age-related Macular Degeneration", American Journal of Ophthalmology, vol. 130 pp. 769-773 Apr. 21, 2000.

Ara, S. et al., "Codon 72 polymorphism of the TP53 gene", Nucleic Acids Research, vol. 18, No. 16 p. 4961 1996.

Bonafe, Massimiliano et al., "p53 codon 72 genotype affects apoptosis by cytosine arabinoside in blood leukocytes", Biochemical and Biophysical Research Communications, vol. 299 pp. 539-541 2002.

Dumont, Patrick et al., "The codon 72 polymorpic variants of p53 have markedly different apoptotic potential", Nature Genetics, vol. 33 pp. 357-365 Feb. 3, 2003.

Frossard, Philippe et al., "An *MboI* Two-Allele Polymorphism May Implicate the Human Renin Gene in Primary Hypertension", Hypertens Res. vol. 21 No. 3 pp. 221-225 1998.

Nalogowska-Glosnicka, Krystyna et al., "Angiotensin II type I receptor gene A1166C polymorphism is associated with the increased risk of pregnancy-induced hypertension", Medical Science Monitor, vol. 6 No. 3 pp. 523-529 2000.

Erdman, J. et al., "Characterization of polymorphisms in the promoter of the human angiotension II subtype I (AT1) receptor gene", American Human Genetics, vol. 63 pp. 36-374 1999.

Katsuya, Tomohiro et al., "Genomic organization and polymorphism of human angiotensin II type 2 receptor: no evidence for its gene mutation in two families of human premature ovarian failure syndrome", Molecular and Cellular Endocrinology, vol. 127, pp. 221-228 1997.

Tsujita, Vasuyuki et al., "Lack of Association between Genetic Polymorphism of *CYP11B2* and Hypertension in Japanese: The Suita Study", Hypertens Res, vol. 24 No. 2 pp. 105-109 2001.

Lindpaintner, Klaus et al., "A Prospective Evaluation of an Angiotensin-Converting Enzyme Gene Polymorphism and the Risk of Ischemic Heart Disease", The New England Journal of Medicine, vol. 332 No. 11 pp. 706-711 Mar. 16, 1995.

Lyamichev, Victor et al., "Polymorphism identification and quantitative detection of genomic DNA by invasive cleavage of oligonucleotide probes", Nature Biotechnology, vol. 17 pp. 292-296 Mar. 1999.

Narayanaswami, Gowri et al., "Improve Efficiency of Mutation Detection by Dematuring High-Performance Liquid Chromatography Using Modified Primers and Hybridization Procedure", Genetic Testing, vol. 5, No. 1 pp. 9-16 2001.

Altomare, K. et al., "The allele$(A)_{110}$in the promoter region of the HSP70-1 gene is unfavorable to longevity in womem", Biogerontology, vol. 4, pp. 215-220 2003.

Wu, Yih-Ru et al., "Analysis of heat-shock protein 70 gene polymorphisms and the risk of Parkinson's disease", Hum Genet, vol. 114 pp. 236-241 2004.

* cited by examiner

METHOD FOR DIAGNOSING OR PREDICTING SUSCEPTIBILITY TO OPTIC NEUROPATHY

CROSS-REFERENCE TO RELATED APPLICATIONS

This Application is a 371 National Stage Entry of PCT/JP2005/005601, filed Mar. 18, 2005, which claims the benefit of U.S. Provisional Patent Applications 60/553,986, filed Mar. 18, 2004, 60/604,704, filed Aug. 27, 2004, and 60/607,359, filed Sep. 7, 2004.

TECHNICAL FIELD

The present invention relates to a set of genetic polymorphisms linked to optic neuropathy.

BACKGROUND ART

Glaucoma is a major cause of blindness worldwide, and estimated approximately 67 million people suffered from some form of glaucoma. The majority of cases occur as late adult onset (typically over age 40 years) of primary open-angle glaucoma (POAG), which is the most common form of glaucoma and affects approximately 2% in white population and 7% of black population over 40 years old. POAG results in a characteristic visual field changes corresponding to the excavation of the optic disc that is usually associated with an elevation of intraocular pressure (IOP). Normal-tension glaucoma (NTG) is a form of open-angle glaucoma in which typical glaucomatous cupping of the optic nerve head and visual field loss are present but in which there is no evidence of increased IOP over 21 mm Hg at all times. In Japan, prevalence of glaucoma is approximately 3.5% over 40 years old: POAG 0.58% and NTG 2.04%. Prevalence of NTG in Japanese population is high compared with that in other populations. Glaucoma is a multifactorial disorder characterized by a progressive optic neuropathy associated with a specific visual field loss, and results from the interaction of multiple genes and environmental influences, although intraocular pressure (IOP) is a major risk factor for glaucoma.

Risk factors to develop glaucoma include high IOP, age, race, positive family history, myopia, the presence of diabetes or hypertension, and genetic factors. Although the exact pathogenesis of glaucomatous optic neuropathy is remains unclear, it is generally accepted that an increased IOP is a major risk factor. Current treatment for glaucoma consists of interventions which lower IOP. However, in some patients with glaucoma, NTG or advanced stage of POAG, reduction of IOP does not prevent the progression of the disease, indicating that factors other than an increased IOP may be involved in the development or progress of glaucoma.

POAG and NTG are a heterogeneous group of conditions probably with different multi-factorial etiologies resulting in the observed patterns of neuronal loss in the optic disk. The association between glaucoma and the presence of many systemic vascular diseases including low systemic blood pressure, nocturnal dips in blood pressure, hypertension, migraine, vasospasm, and diabetes has been reported. The presence of optic disc hemorrhages in NTG patients suggests that vascular insufficiencies are deeply involved in the development and progression of NTG. A high percentage of patients with POAG receive a wide variety of medications for coexisting disorder. Especially, systemic hypertension was the most common disorder, occurring in 48% of the total population.

Glaucoma-like morphological changes have been reported in patients with Leber's hereditary optic neuropathy (LHON) at the atrophic stage and dominant optic atrophy (DAO). Recently, the inventor has reported optic disc excavation by a quantitative analysis using Heidelberg retinal tomography (HRT) in the atrophic stage of Japanese 15 patients with LHON harboring the 11778 mutation (Mashima Y et. al., Arch Clin Exp Ophthalmol 2003; 241:75-80, the contents of the cited reference are herein incorporated by reference). LHON is a maternally-transmitted eye disease that mainly affects young adult men. Approximately 70% of patients were male. This disease usually causes severe and permanent loss of vision resulting in a visual acuity of less than 0.1. Visual field defects are present as central or cecocentral scotomas. So far more than 20 point mutations of mitochondrial DNA (mtDNA) have been reported in LHON patients worldwide (Brown M D et. al., Clin Neurosci 1994; 2:138-145, the contents of the cited reference are herein incorporated by reference), and more than 80% of LHON patients carry one of three mtDNA mutations at nucleotide position 3460, 11778, or 14484 (Mackey D A et. al., Am J Hum Genet 1996; 59:481-485, the contents of the cited references are herein incorporated by reference). Although NTG patients were tested for the three LHON mutations of mtDNA nucleotide positions 3460, 11778 and 14484, no mutations and no defects in respiratory chain activity in skeletal muscle samples were detected (Brierley E J et. al., Arch Ophthalmol 114:142-146 and Opial D et. al., Graefes Arch Clin Exp Ophthalmol 239: 437-440, the contents of the cited references are herein incorporated by reference).

The major difference among LHON patients with one of these mtDNA mutations is in the clinical course. The 3460 and 14484 mutations are associated with better visual prognosis than the 11778 mutation which shows visual recovery rates of only 4% to 7% (Oostra R J et. al., J med Genet 1994; 31:280-286, Riordan-Eva P et. al., Brain 1995; 118:319-337, Mashima Y et. al., Curr Eye Res 1998; 17:403-408, the contents of the cited reference are herein incorporated by reference). However, visual recovery has been documented in some patients with the 11778 mutation and an age of onset in the low teens (Stone E M et. al., J clin Meuro-Ophthalmol 1992; 12:10-14, Zhu D et. al., Am J Med Genet 1992; 42:173-179, Salmaggi A et. al., Intern J Neuroscience 1994; 77:261-266, Oostra R J et. al., Clin Genet 1997; 51:388-393, Mashima Y et. al., Jpn J Ophthalmol 2002; 46:660-667, the contents of the cited references are herein incorporated by reference). Recovery of vision appears to be more likely when visual deterioration begins at an early age, even in patients with the 11778 mutation.

The clinical variability of LHON patients, which includes age at onset, male predilection, incomplete penetrance, and visual recovery, suggests that the disease most likely results from polygenic or multifactorial mechanisms, possibly involving environmental stressors, X-chromosomal loci, and other mtDNA mutations (Man P Y W et. al., J Med Genet 2002; 39:162-169, the contents of the cited reference are herein incorporated by reference). However, attempts to identify a relevant locus on the X-chromosome have not been successful (Chalmers R M et. al., Am J Hum Genet 1996; 59:103-108 and Pegoraro E et. al., Am J Med Genet 2003; 119A:37-40, the contents of the cited reference are herein incorporated by reference). So-called "secondary LHON mutations" are more frequently found in European LHON patients than in unaffected Europeans and are polymorphisms linked to the European haplotype J. These polymorphisms are not strong autonomous risk factors (Brown M D et. al., Am J Hum Genet 1997; 60:381-387 and Torroni A et. al., Am J Hum Genet 1997; 60:1107-1121, the contents of the cited reference are herein incorporated by reference).

Thus, the primary mutations are the major risk factors in LHON, but additional etiologic factors that augment or modulate the pathogenic phenotypes appear to be necessary. Considerable evidence indicates that heavy alcohol and/or tobacco use increases the risk of optic neuropathy in LHON families (Smith P R et. al., Q J Med 1993; 86:657-660, Chalmers R M et. al., Brain 1996; 119:1481-1486 and Tsao K et. al., Br J Ophthalmol 1999; 83:577-581, the contents of the cited reference are herein incorporated by reference), although one study did not find this association. Possible secondary genetic interactions are complex and not firmly established (Kerrison J B et. al., Am J Ophthalmol 2000; 130:803-812, the contents of the cited reference are herein incorporated by reference).

Oxidative stress has been implicated in many disorders associated with mutations of mtDNA. A recent investigation in an animal model identified reactive oxygen species (ROS) as a likely factor in the pathogenesis of LHON (Qi X et. al., Invest Ophthalmol Vis Sci 2003; 44:1088-1096, the contents of the cited reference are herein incorporated by reference). Additionally, the mtDNA LHON pathogenic mutations were found to predispose cells to Fas-dependent apoptotic death in vitro (Danielson S R et. al., J Biol Chem 2002; 277:5810-5815, the contents of the cited reference are herein incorporated by reference). These findings implied that there must be some nuclear modifier genes involved for developing LHON.

SUMMARY OF THE INVENTION

The inventor has revealed that some known and unknown SNPs are linked to onset of optic neuropathy including glaucoma and Leber's disease and completed the instant invention.

Accordingly, the present invention provides a set of genetic polymorphisms being associated with optic neuropathy, which comprises at least one polymorphism selected from the group consisting of:

(1) AAG to AAT substitution at codon 198 of the Endothelin-1 gene (Lys198Asn);

(2) −1370T>G polymorphism of the Endothelin-1 gene promoter region;

(3) A138 insertion/deletion (A138I/D) polymorphism in exon 1 of the Endothelin-1 gene;

(4) +70C>G polymorphism in 3' non-coding region of the Endothelin receptor A gene;

(5) +1222C>T polymorphism of the Endothelin Receptor A gene;

(6) CAC to CAT substitution at codon 323 in exon 6 of the Endothelin Receptor A gene (His323His);

(7) −231A>G polymorphism of the Endothelin Receptor A gene promoter region;

(8) CTG to CTA substitution at codon 277 in exon 4 of the Endothelin receptor B gene;

(9) 9099C>A polymorphism of the Mitochondrial gene;

(10) 9101T>G polymorphism of the Mitochondrial gene;

(11) 9101T>C polymorphism of the Mitochondrial gene;

(12) 9804G>A polymorphism of the Mitochondrial gene;

(13) 11778G>A polymorphism of the Mitochondrial gene;

(14) −713T>G polymorphism of the Angiotensin II type 1 receptor gene promoter region;

(16) 3123C>A polymorphism of the Angiotensin II type 2 receptor gene;

(25) CAA to CGA substitution at codon 192 of the Paraoxonase 1 gene (Gln192Arg);

(26) TTG to ATG substitution at codon 55 of the Paraoxonase 1 gene (Leu55Met);

(27) CGG to CAG substitution at codon 144 of the Noelin 2 gene (Arg144Gln);

(32) GGA to CGA substitution at codon 389 of the β1 adrenergic receptor gene (Gly389Arg);

(35) 1105T>C polymorphism of the Myocilin gene (Phe369Leu);

(36) 412G>A polymorphism of the Optineurin gene;

(37) 1402C>T polymorphism of the E-Selectin gene;

(38) The combination of polymorphisms of −857C>T of the Tumor necrosis factor α gene promoter region and 412G>A of the Optineurin gene;

(39) The combination of polymorphisms of −863C>A of the Tumor necrosis factor α gene promoter region and 603T>A of the Optineurin gene

(40) CGC to CCC substitution at codon 72 of the TP53 gene (Arg72Pro);

(41) TAC to CAC substitution at codon 113 of the Microsomal epoxide hydrase 1 gene (Tyr113His);

(42) −110A>C polymorphism of the Heatshock protein 70-1 gene promoter region;

(43) −338C>A polymorphism of the Endothelin converting enzyme gene promoter region;

(44) −670A>G polymorphism of the CD95 gene promoter region;

(45) AAG to AAA substitution at codon 119 of the Microsomal epoxide hydrase 1 gene (Lys119Lys);

(47) GGA to AGA substitution at codon 16 of the β2 adrenergic receptor gene (Gly16Arg); and

(48) CAA to GAA substitution at codon 27 of the β2 adrenergic receptor gene (Gln27Glu).

In addition, the present invention also provides a method for diagnosing or predicting susceptibility to optic neuropathy in a human subject, which comprising the steps of:

i) obtaining a biological sample from the subject, ii) determining genotype of the sample in respect of the set of the polymorphisms defined as above, and iii) diagnosing or predicting susceptibility to optic neuropathy in the subject based on the genotype.

According to the present invention, the optic neuropathy may preferably be glaucoma or Laber's disease. The polymorphism (1)-(39) and (42)-(48) may be used especially for glaucoma. Among them, those (1), (2), (5)-(7), (16), (26), (32), (43) and (45) may be used especially for normal tension glaucoma and those (4), (14), (25), (35), (36), (38), (42), (44), (47)-(48) may be used especially for primary open angle glaucoma. The polymorphisms (40) and (41) may be used especially for Laber's disease.

According to the present invention, the set of polymorphisms may further comprise at least one other polymorphism which has been known to be associated with optic neuropathy.

In another aspect of the present invention, a kit for diagnosing or predicting susceptibility to optic neuropathy in a human subject which comprises primer set and/or probe suitable for determining genotype in respect of the set of genetic polymorphisms defined as above.

In further aspect of the present invention, neuly identified SNPs are provided in Mitocondorial gene, Myocilin gene and Noelin 2 gene. Accordingly, the present invention encompass nucleotide fragment covering those SNPs. In general, in order to determine genotype in respect of said SNP, 90 or more contignous nucleotide sequence containing the SNP may be required. Namely, an isolated polynucleotide consisting of a segment of the sequence:

```
8881 tctaagatta aaaatgccct agcccacttc ttaccacaag gcacacctac acccettatc  (SEQ ID NO: 1)

8941 cccatactag ttattatcga aaccatcagc ctactcattc aaccaatagc cctggccgta

9001 cgcctaaccg ctaacattac tgcaggccac ctactcatgc acctaattgg aagcgccacc

9061 ctagcaatat caaccattaa ccttccctct acacttatca tcttcacaat tctaattcta

9121 ctgactatcc tagaaatcgc tgtcgcctta atccaagcct acgttttcac acttctagta

9181 agcctctacc tgcacgacaa cacataatga cccaccaatc acatgcctat catatagtaa
```

wherein the segment comprises at least 90 contignuous nucleotide, and the at least 90 contignuous nucleotide includes position 9099 of the sequence, and wherein position 9099 of the sequence is A or an isolated polynucleotide which is entirely complementary to the above segment; or wherein the segment comprises at least 90 contignuous nucleotide, and the at least 90 contignuous nucleotide includes position 9101 of the sequence, and wherein position 9101 of the sequence is G; or an isolated polynucleotide which is entirely complementary to either of the above segment.

The present invention further provides an isolated polynucleotide consisting of a segment of the sequence:

```
301 actggaaagc acgggtgctg tggtgtactc ggggagcctc tatttccagg gcgctgagtc  (SEQ ID NO: 2)

361 cagaactgtc ataagatatg agctgaatac cgagacagtg aaggctgaga aggaaatccc

421 tggagctggc taccacggac agttcccgta ttcttggggt ggctacacgg acattgactt

481 ggctgtggat gaagcaggcc tctgggtcat ttacagcacc gatgaggcca aaggtgccat

541 tgtcctctcc aaactgaacc cagagaatct ggaactcgaa caaacctggg agacaaacat
```

wherein the segment comprises at least 90 contignuous nucleotide, and the at least 90 contignuous nucleotide includes codon 369, which is corresponding to the underlined nucleotides of the sequence, and wherein codon 369 is substituted such that it codes for Leu, or an isolated polynucleotide which is entirely complementary to the above segment.

The present invention further provides an isolated polynucleotide consisting of a segment of the sequence:

```
79741  ttagttccta caatggagtc atgtctggga agaatctagg gtccaatatg agccacatgt  (SEQ ID NO: 3)

79801  caagggccag gtgtgcatca aagacaaagg gtgaagttat gagtcagagg ttggagtcat

79861  gtctgggtca aaggccaggg gtcaggcttg gccatggttc catcttgatg cacaggagct

79921  gaaggacagg atgacggaac tgttgcccct gagctcggtc ctggagcagt acaaggcaga

79981  cacgcggacc attgtacgct tgcgggagga ggtgaggaat ctctccggca gtctggcggc

80041  cattcaggag gagatgggtg cctacgggta tgaggacctg cagcaacggg tgatggccct

80101  ggaggcccgg ctccacgcct gcgcccagaa gctgggtatg ccttggccct tgaccctgac

80161  ccctgatctc tgactgccac acccaactcc agtatcacct gtttgtgcct agaagctgga

80221  cacagttttg acctctaact tttaaacctc aacccttgac cttcctacct aaggctacac
```

wherein the segment comprises at least 90 contignuous nucleotide, and the at least 90 contignuous nucleotide includes codon 144, which is corresponding to the underlined nucleotides of the sequence, and wherein codon 144 is substituted such that it codes for Gln, or an isolated polynucleotide which is entirely complementary to the above segment.

PREFERRED EMBODIMENT OF THE INVENTION

Figure 1:
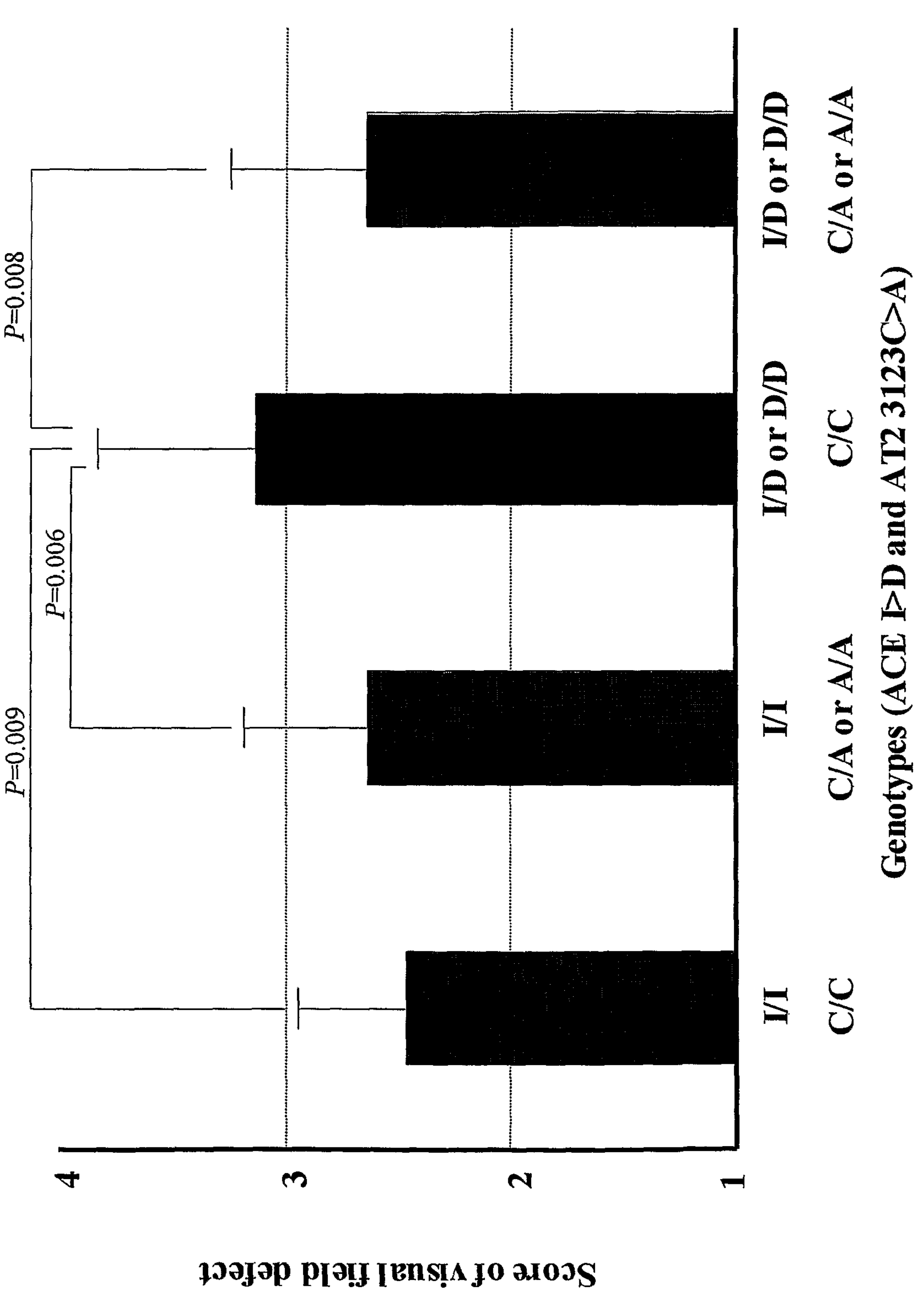
FIG. 1 represents correlation of clinical Characteristics of NTG Patients with AT2R 3123C>A Polymorphism and ACE I/D Polymorphism

In the present specification and claims, "genetic polymorphism" means genomic diversity between individuals at a locus. Genetic polymorphism may be single nucleotide substitution called as "Single nucleotide polymorphisms" or "SNPs" as well as those consisting of plural nucleotides. The genetic polymorphism may or may not be those affect on the phenotype of the individual. In addition, a nucleotide sequence of an individual is different from the corresponding wild type sequence, i.e., having insertion, deletion or substitution on the wild type sequence, said nucleotide sequence is called as "genetic mutant" and the genetic mutant is also included in "polymorphic variant" according to the present invention.

In the present specification and claims, expression like "9099C>A" or "C9099A" means that the gene has a polymorphism at position 9099, that is, there are two alleles of the gene and the one has cytosine or C and the other has adenine or A at 9099 (bi-allelic). It does not necessarily mean the frequent allele has C whereas the rare allele has A at said position.

The expression like "Gln192Arg" represents an amino acid substitution due to the base substitution in the gene coding for the amino acid sequence. For example, Gln192Arg represents Glycine at codon 192, i.e. amino acid number 192, is replaced with Arginine or Arg. This also means that there are polymorphic variants of the protein wherein the amino acid at codon 192 is Gln or Arg.

According to the present invention, determining genotype in respect of the genetic polymorphisms may be carried out by every single polymorphism, or plurality or all polymorphisms may be determined at the same time.

In the present invention, the method for diagnosing or predicting susceptibility to optic neuropathy in a human subject which comprises determining genotype in respect of the set of genetic polymorphism of which relationship with optic neuropathy is newly reported in this application. In addition to the genetic polymorphism identified as being linked to optic neuropathy by the instant invention, any other polymorphism which had been revealed as being linked to optic neuropathy may be detected together. By employing plural genetic polymorphisms linked to optic neuropathy, the diagnostic probability can be improved.

According to the present invention, the method used for determining genotype in respect of the genetic polymorphisms is not limited and may be any of those known to the art. Representative method for determining genotype in respect of the genetic polymorphisms include polymerase chain reaction restriction fragment length polymorphism (PCR-RFLP) analysis, polymerase chain reaction followed by single strand conformation polymorphism (PCR-SSCP) analysis, ASO hybridization analysis, direct sequencing analysis, ARMS analysis, DGGE analysis, RNaseA cleaving analysis, chemical restriction analysis, DPL analysis, TaqMan® PCR analysis, Invader® assay, MALDI-TOF/MS analysis, TDI analysis, single nucleotide extension assay, WAVE assay, one molecular fluorescent detection assay. According to the present invention, the detection method may be one of those or combination of two or more.

According to the present invention, biological sample to be used for detecting the genetic polymorphism is not specifically limited and may be hair, blood, saliva, lymph fluid, respiratory tract mucosa, cultured cells and urine.

In the specification and claims, "diagnosing or predicting susceptibility to optic neuropathy" includes not only diagnosing onset of optic neuropathy but also determining risk factors which hasten onset of the disease as well as accelerate the disease progresses.

According to the present invention, kits for detecting the genetic polymorphism as well as protein polymorphism identified as above are also provided. Said kits may comprise primers and/or probes which are specifically designed for detecting the above-identified genetic polymorphisms; antibodies for detecting the above-identified protein polymorphism. According to the present invention, said kit may be used for diagnosing or predicting susceptibility to optic neuropathy.

In the present specification and claims, the term "primer" denotes a specific oligonucleotide sequence which is complementary to a part of the target nucleotide sequence and used to hybridize to the target nucleotide sequence. A primer serves as an initiation point for nucleotide polymerization catalyzed by either DNA polymerase, RNA polymerase or reverse transcriptase.

The term "probe" denotes a defined nucleic acid segment which can be used to identify a specific polynucleotide sequence present in samples or confirming target DNA or RNA in a gene modifying process, said nucleic acid segment comprising a nucleotide sequence complementary to the specific polynucleotide sequence to be identified.

According to the present invention, primers and probes may be designed based on the targeted sequence so that they are specific to the position at which the targeted polymorphism is expected and/or surrounding sequence of the position so long as they are not identical to some other genes, i.e. it is necessary not to be repeating sequence nor palindrome sequence.

According to the present invention, genetic polymorphisms which are linked to optic neuropathy, especially glaucoma and Leber's disease are identified. Based on the findings, the genotype in respect of the genetic polymorphisms of a biological sample obtained from an individual is determined and based on thus obtained genotype, onset of the disease or predicted risk for onset of the disease can be determined.

In addition to the polymorphisms identified (1)-(48) as above, genotypes in respect of some other genetic polymorphisms which had been known to the art being highly associated with optic neuropathy may be determined for improved reliability of the diagnosis or prediction.

For example, two types of genetic polymorphisms in myocilin as well as optineurin genes have been revealed by the inventor to be associated with onset of primary open-angle glaucoma. In addition to the two genes, 4 other genetic polymorphisms including mutations had been identified to be associated with primary open-angle glaucoma. Almost 100% of the subjects having both the risk genotype in respect of the genetic polymorphisms of the present invention and of those already known to the art may develop glaucoma. That is, the set of the genetic polymorphisms will be useful for preclinical test.

In regard of some SNPS, the inventor confirmed correlation with optic neuropathy in a specific group, such as race or sex. Accordingly, said SNPs may preferably be used for diagnosing or predicting the risk for optic neuropathy in the specified group.

Further, statistical analysis of the genotype in respect of the set of polymorphisms may provide useful information such as predictive age of onset, predictive association with lifestylerelated diseases, predictive association with symptom factors. In addition, effect of some medical treatments may also be predictable based on the information.

According to the present invention, predicting susceptibility to optic neuropathy can be carried out before onset of the disease based on the genotype, and the subject can receive advice on how to remove the risk factor, for example, to improve life style or alter the environment. In addition, it may possible to receive an early treatment such as reduction of the risk gene. an appropriate treatment can be started earlier. Consequently, those "order made treatment" can reduce the risk for vision loss.

For example, in case a subject has the genotype linked to high risk for onset of optic neuropathy, inhibition of onset, reduction of the risk of onset or relief of symptoms can be expected by introducing to the subject the genotype linked to low risk for onset and expressing the same. Further, anti sence to the mRNA of the allele of high risk for onset of optic neuropathy or RNAi method may be used for inhibiting expression of the high risk allele.

In another aspect, based on the genotype determination in respect of the set of polymorphisms shown in the present invention, genetic etiology of optic neuropathy may be revealed and thus obtained etiology may be useful for development of novel medical agents.

Further, by combining genotype information which is associated with optic neuropathy obtained by the present invention and the other genotype information which is associated with life style diseases and the like, comprehensive risk for age-related, life-style related diseases can be predicted and used for high quality of life.

The present invention will be further illustrated by means of the examples shown below. It is to be expressly understood, however, that the examples are for purpose of illustration only and is not intended to limit of the scope of the invention.

EXAMPLE 1

Genetic Variants of TP53 and EPHX1 in Leber's Hereditary Optic Neuropathy and their Relationship to Age at Onset Purpose: To determine whether genetic polymorphisms of the genes for oxidative stress and apoptosis cause the clinical variability in patients with Leber's hereditary optic neuropathy (LHON).

Materials and Methods

Patients

We studied 86 unrelated Japanese patients with LHON carrying the 11778 mutation with homoplasmy. Their mtDNA mutation was confirmed by polymerase chain reaction followed by a restriction-enzyme assay which revealed concordant gain of the MaeIII site (Mashima Y et. al., Curr Eye Res 1998; 17:403-408, the contents of the cited reference are herein incorporated by reference).

The mean age at the onset of visual loss in 86 LHON patients was 25.1±13.0 years with a range 3 to 65 years.

Genomic DNA Extraction and Genotyping

DNA was extracted from peripheral blood leukocytes by the SDS-proteinase K and phenol/chloroform extraction method. Polymorphisms were examined in the oxidative stress-related gene, microsomal epoxide hydrolase (EPHX1) (Kimura K et. al., Am J Ophthalmol 2000; 130:769-773, the contents of the cited reference are herein incorporated by reference).), and the apoptosis-related gene, Arg72Pro in TP53 (Ara S et. al., Nucleic Acids Res 1990; 18:4961, the contents of the cited reference are herein incorporated by reference).

Each polymorphism was identified using polymerase chain reaction-restriction fragment length polymorphism (PCR-RFLP) techniques (Table 1).

TABLE 1

Primer sequences, product size, and annealing temperatures

| Gene | | Primer sequences | Product Size (bp) | Annealing Temperature (° C.) | Restriction Enzyme | |
|---|---|---|---|---|---|---|
| TP53 | F | TTG CCG TCC CAA GCA ATG GAT GA | 199 | 60.0 | Acc II | (SEQ ID NO: 4) |
| | R | TCT GGG AAG GGA CAG AAG ATG AC | | | | (SEQ ID NO: 5) |
| EPHX1 | F | GAT CGA TAA GTT CCG TTT CAC C | 165 | 56.0 | EcoR V | (SEQ ID NO: 6) |
| | R | TCA ATC TTA GTC TTG AAG TGA GGA T | | | | (SEQ ID NO: 7) |

Results

The associations between age at onset and the polymorphisms were presented in Table 2-1 and Table 2-2.

TABLE 2-1

Association between age at onset and TP53 (Arg72Pro) and EPHX1 (Tyr113His) gene polymorphism in Leber's hereditary optic neuropathy

| Gene | Genotype | | P |
|---|---|---|---|
| TP53 (Arg72Pro) | Arg/Arg | Arg/Pro + Pro/Pro | 0.009 |
| Age at onset | 20.7 ± 10.6 (n = 35) | 28.1 ± 13.8 (n = 51) | |
| EPHX1 (Tyr113His) | Tyr/Tyr + Tyr/His | His/His | 0.038 |
| Age at onset | 27.9 ± 13.9 (n = 45) | 22.1 ± 11.4 (n = 41) | |

P Value for t-test

TABLE 2-2

Association between age at onset and TP53 (Arg/Arg) and EPHX1 (His/His) gene polymorphism in Leber's hereditary optic neuropathy

| Group 1 Arg/Arg and His/His | Group 2 Arg/Arg or His/His | Group 3 others | P |
|---|---|---|---|
| 17.7 ± 9.3 (n = 19) | 25.3 ± 11.3 (n = 38) | 29.8 ± 15.1 (n = 29) | 0.0044 |

P value for Kruskal-Wallis

Group 1: Patients who have Arg/Arg at codon 72 in TP53 and His/His at codon 113 in EPHX1

Group 2: Patients who have Arg/Arg at codon 72 in TP53 but not His/His at codon 113 in EPHX1, or His/His at codon 113 in EPHX1 but not Arg/Arg at codon 72 in TP53

Group 3: Patients other than Groups 1 and 2

As shown in Table 2-1, the codon 72 genotype in TP53 and the codon 113 genotype in EPHX1 were significantly associated with younger age at onset of Leber's hereditary optic neuropathy.

As shown in Table 2-2, the co-existence of the Codon 72 genotype in TP53 and the codon 113 genotype in EPHX1 were significantly associated with younger age at onset of Leber's hereditary optic neuropathy.

ant was more efficient than the Pro72 variant at inducing apoptosis, with at least one mechanism underlying this greater efficiency being enhanced localization of Arg72 variant to mitochondria in tumor cells. The synthetic p53 inhibitors might be highly effective in treating LHON in which neurons died by apoptosis triggered by mitochondrial impairment and oxidative stress.

Partial nucleotide sequences for EPHX1 and TP53 genes containing the targeted polymorphism are as follows:

```
EPHX1 Tyr113His Codon 113 (underlined) (TAC to CAC change)
  181 tgctgggctt tgccatctac tggttcatct cccgggacaa agaggaaact ttgccacttg  (SEQ ID NO: 8)

  241 aagatgggtg gtgggggcca ggcacgaggt ccgcagccag ggaggacgac agcatccgcc

  301 ctttcaaggt ggaaacgtca gatgaggaga tccacgactt acaccagagg atcgataagt

  361 tccgtttcac cccacctttg gaggacagct gcttccacta tggcttcaac tccaactacc

  421 tgaagaaagt catctcctac tggcggaatg aatttgactg gaagaagcag gtggagattc

  481 tcaacagata ccctcacttc aagactaaaa ttgaagggct ggacatccac ttcatccacg

  541 tgaagccccc ccagctgccc gcaggccata ccccgaagcc cttgctgatg gtgaacggct

  601 ggcccggctc tttctacgag ttttataaga tcatcccact cctgactgac cccaagaacc

  661 atggcctgag cgatgagcac gtttttgaag tcatctgccc ttccatccct ggctatggct

  721 tctcagaggc atcctccaag aaggggttca actcggtgge caccgccagg atcttttaca

TP 53 Codon 72(underlined): CGC(Arg) to CCC(Pro),
13081 gcaggcccac caccccgacc ccaaccccag ccccctagca gagacctgtg ggaagcgaaa  (SEQ ID NO: 9)

13141 attccatggg actgactttc tgctcttgtc tttcagactt cctgaaaaca acgttctggt

13201 aaggacaagg gttgggctgg ggacctggag ggctggggac ctggagggct gggggggctgg

13261 ggggctgagg acctggtcct ctgactgctc ttttcaccca tctacagtcc ccc ttgccgt

13321 cccaagcaat ggatgatttg atgctgtccc cggacgatat tgaacaatgg ttcactgaag

13381 acccaggtcc agatgaagct cccagaatgc cagaggctgc tccccgcgtg gcccctgcac

13441 cagcagctcc tacaccggcg gcccctgcac cagcccctc ctggcccctg tcatcttctg

13501 tcccttccca gaaaacctac cagggcagct acggtttccg tctgggcttc ttgcattctg

13561 ggacagccaa gtctgtgact tgcacggtca gttgccctga ggggctggct tccatgagac

13621 ttcaatgcct ggccgtatcc ccctgcattt cttttgtttg gaactttggg attcctcttc

13681 accctttggc ttcctgtcag tgttttttta tagtttaccc acttaatgtg tgatctctga

13741 ctcctgtccc aaagttgaat attcccccct tgaatttggg cttttatcca tcccatcaca

13801 ccctcagcat ctctcctggg gatgcagaac ttttcttttt cttcatccac gtgtattcct
```

These results indicated that detection of the Arg/Arg homozygote in TP53 and His/His homozygote in EPHX1 make possible the early diagnosis and early treatment of Leber's hereditary optic neuropathy.

These results also indicated that the Codon 72 polymorphism may interact with mitochondrial dysfunction to influence disease expression. Individual variations may exist in the apoptotic response that is correlated with the polymorphism at codon 72 of p53. Bonafe et al (Biochem Biophys Res Commun 2002; 299:539-541.). reported that cultured cells from healthy subjects carrying the Arg/Arg genotype underwent more extensive apoptosis than cells from Arg/Pro subjects in response to the cytotoxic drug cytosine arabinoside. Thus, naturally occurring genetic variability at the p53 gene could partly explain individual differences in in vivo susceptibility of cells to a chemotherapeutic drug. Dumount et al (Nat Genet 2003; 33:357-365). reported that the Arg72 vari-

EXAMPLE 2

Mitochondrial DNA Mutations Related with Leber's Hereditary Optic Neuropathy in Primary Open-Angle Glaucoma and Normal-Tension Glaucoma Materials and Methods Patients A total of 651 blood samples were collected at seven institutions in Japan. There were 201 POAG patients, 232 NTG patients, and 218 normal controls, and none of the subjects was related to others in this study.

The mean age at the time of examination was 61.2±16.0 years in POAG, 58.8±13.6 years in NTG, and 70.6±10.9 years in the control subjects. The mean age of the control subjects was significantly older than that of POAG patients (P<0.001)

and the NTG patients (P<0.001). We purposely selected older control subjects to reduce the probability that a subset of them would eventually develop glaucoma. There were 112 (55.7%) men in the POAG group, 108 (46.6%) in the NTG group, and 89 (40.8%) in the control group.

Patients were considered to have POAG if they had a normal open-angle, a cup-disc ratio greater than 0.7 with typical glaucomatous visual field loss on either Goldmann or Humphrey perimetry, and the absence of ocular, rhinologic, neurological, or systemic disorders which might be responsible for the optic nerve damage. Patients with NTG had an IOP of 21 mmHg or lower. Patients with exfoliative glaucoma, pigmentary glaucoma, and corticosteroid-induced glaucoma were excluded.

Two-hundred-eighteen control samples were obtained from Japanese subjects who had no known eye abnormalities except for cataracts. These subjects were older than 40 years, had IOPs below 21 mm Hg, had normal optic discs, and no family history of glaucoma.

Detection of mtDNA Mutations by Invader® Assay

Genomic DNA was isolated from peripheral blood lymphocytes by standard methods of phenol-chloroform extraction.

The primary probes (wild and mutant probes) and Invader® oligonucleotides (Invader® probe) used to detect the six mtDNA mutations (G3460A, T9101C, G9804A, G11778A, T14484C, and T14498C) by the Invader® assay are shown in Table 3.

TABLE 3

The oligonucleotide sequence of wild type, mutant, and Invader probes with Invader assay to detect mutation of mtD

| Nucleotide | Target | Probe | Sequence | Tm | Dye | |
|---|---|---|---|---|---|---|
| G3460A | Anti-sense | Wild | Flap sequence-gccataaaactcttcacca | 63.2 | RED | (SEQ ID NO: 10) |
| | | Mutant | Flap sequence-accataaaactcttcaccaaa | 63.3 | FAM | (SEQ ID NO: 11) |
| | | Invader | ccctacgggctactacaacccttcgctgact | 77.7 | | (SEQ ID NO: 12) |
| T9101C | sense | Wild | Flap sequence-atgataagtgtagagggaagg | 64.1 | FAM | (SEQ ID NO: 13) |
| | | Mutant | Flap sequence-gtgataagtgtagagggaag | 62.2 | RED | (SEQ ID NO: 14) |
| | | Invader | ggcgacagcgatttctaggatagtcagtagaattagaa ttgtgaagT | 76.8 | | (SEQ ID NO: 15) |
| G9804A | anti-sense | Wild | Flap sequence-gccacaggcttcca | 63.7 | FAM | (SEQ ID NO: 16) |
| | | Mutant | Flap sequence-accacaggcttccac | 63.7 | RED | (SEQ ID NO: 17) |
| | | Invader | catttccgacggcatctacggctcaacatttttgtaT | 76.7 | | (SEQ ID NO: 18) |
| G1178A | Anti-sense | Wild | Flap sequence-gcatcataatcctctctcaag | 63.5 | RED | (SEQ ID NO: 19) |
| | | Mutant | Flap sequence-acatcataatcctctctcaag | 62.2 | FAM | (SEQ ID NO: 20) |
| | | Invader | gcctagcaaaactcaaactacgaacgcactcacagtct | 77.7 | | (SEQ ID NO: 21) |
| T14484C | Sense | Wild | Flap sequence-atggttgtctttggatatactac | 63.4 | FAM | (SEQ ID NO: 22) |
| | | Mutant | Flap sequence-gtggttgtctttggatatacta | 62.8 | RED | (SEQ ID NO: 23) |
| | | Invader | ttttgggggaggttatatgggtttaatagttttttta atttatttagggggaatgt | 76.0 | | (SEQ ID NO: 24) |
| T14498C | sense | Wild | Flap sequence-atttagggggaatgatggt | 64.0 | FAM | (SEQ ID NO: 25) |
| | | Mutant | Flap sequence-gtttagggggaatgatgg | 62.7 | RED | (SEQ ID NO: 26) |
| | | Invader | tgttattattctgaattttgggggaggttatatgggtt taatagtttttttaatttT | 74.1 | | (SEQ ID NO: 27) |

Invader® assay FRET-detection 256-well plates (Third Wave Technologies, Inc, Madison, Wis.) contains the generic components of an Invader® assay (Cleavage® enzyme VIII, FRET probes, MOPS buffer, and polyethylene glycol) dried in each of the individual wells. The biplex format of the Invader® assay enabled simultaneous detection of two DNA sequences in a single well.

The detail method was described previously. In brief, 8 μl of the primary probe/Invader®/mixture and total DNA (10 ng) samples were added to each well of a 96-well plate, and were denatured by incubation at 95° C. for 10 min. After 15 μl of mineral oil (Sigma, St. Louis, Mo.) was overlaid on all reaction wells, the plate was incubated isothermally at 63° C. for 2 hours in a PTC-100 thermal cycler (MJ Research, Waltham, Mass.) and then kept at 4° C. until fluorescence measurements. The fluorescence intensities were measured on a CytoFlour 4000 fluorescence plate reader (Applied Biosystems, Foster City, Calif.) with excitation at 485 nm/20 nm (wavelength/bandwidth) and emission at 530 nm/25 nm for FAM dye; excitation at 560 nm/20 nm and emission at 620 nm/40 nm for Redmond RED (RED) dye. Each samples was tested in duplicate in the same plate and two fluorescence measurements were performed in each plate. Thus, four measurements were obtained for each sample and they were averaged.

Direct DNA Sequencing

To detect mutations by direct sequencing, the PCR products were first purified with the QIAquick PCR Purification Kit (QIAGEN, Valenica, Calif., USA) to remove unreacted primers and precursors. The sequencing reactions were then performed using the ABI PRISM BigDye Terminator (v.3.1) Cycle Sequencing Kit, according to the manufacturer's protocol (Applied Biosystems). The data were collected by the ABI PRISM 310 Genetic Analyzer and analyzed by the ABI PRISM sequencing analysis program (v.3.7).

TABLE 4

Primer sequences

| mutation | | Primer Sequences (5' to 3') | |
|---|---|---|---|
| 3460 | F | CAG TCA GAG GTT CAA TTC CTC | (SEQ ID NO: 28) |
| | R | TGG GGA GGG GGG TTC ATA GTA | (SEQ ID NO: 29) |
| 11778 | F | GGC GCA GTC ATT CTC ATA AT | (SEQ ID NO: 30) |
| | R | AAG TAG GAG AGT GAT ATT TG | (SEQ ID NO: 31) |
| 14484 | F | none | |
| | R | GCT TTG TTT CTG TTG AGT GT | (SEQ ID NO: 32) |
| 9101 | F | AAA ATG CCC TAG CCC ACT TC | (SEQ ID NO: 33) |
| | R | GTC ATT ATG TGT TGT CGT GC | (SEQ ID NO: 34) |
| 9804 | F | CAC ATC CGT ATT ACT CGC AT | (SEQ ID NO: 35) |
| | R | CGG ATG AAG CAG ATA GTG AG | (SEQ ID NO: 36) |

Results

A total of 651 Japanese subjects were studied. When a nucleotide substitution is located within a primary probe or an invader probe, the examined cases showed no reaction to both probes by Invader assay. In such cases, direct sequence analysis showed single nucleotide polymorphisms (SNPs) at the nucleotide position of 9099, 9101, 9102, 9797, and 9815.

As shown in Table 5, 7 patients including 5 females and 2 males harbored 5 mutations of mtDNA, and have not developed LHON. Two patients (Cases 1 and 2) harbored novel amino acid changes which have not been to associated with LHON, and 5 patients (Cases 3 to 7) harbored LHON mutations.

These mtDNA mutations were not detected in normal controls.

TABLE 5

| Case | mtDNA mutation | Patient |
|---|---|---|
| 1 | C9099A mutation (Ile to Met) | POAG (Male) |
| 2 | T9101G mutation (Ile to Ser) | POAG (Female) |

TABLE 5-continued

| Case | mtDNA mutation | Patient |
|---|---|---|
| 3 | T9101C mutation (Ile to Thr) | POAG (Female) |
| 4 | G9804A mutation (Ala to Thr) | POAG (Male) |
| 5 | G9804A mutation (Ala to Thr) | NTG (Female) |
| 6 | G11778A mutation (Arg to His) heteroplasmy 80% | POAG (Female) |
| 7 | G11778A mutation (Arg to His) heteroplasmy 15% | NTG (Male) |

As described above, we found 5 mtDNA mutations including 2 novel mtDNA mutations in glaucoma patients. These results indicated that mtDNA mutations is one of the risk factor to develop or progress the glaucoma, and detection of the mtDNA mutations makes possible the early diagnosis and early treatment of glaucoma.

Partial nucleotide sequences of mitochondrial gene containing the targeted mutations/polymorphism are as follows:

C9099A, T9101G (underlined)

8881 tctaagatta aaaatgccct agcccacttc ttaccacaag gcacacctac accccttatc (SEQ ID NO: 37)

8941 cccataatag ttattatcga aaccatcagc ctactcattc aaccaatagc cctggccgta 9001 cgcctaaccg ctaacattac tgcaggccac ctactcatgc acctaattgg aagcgccacc 9061 ctagcaatat caaccattaa ccttccctct acacttatca tcttcacaat tctaattcta 9121 ctgactatcc tagaaatcgc tgtcgcctta atccaagcct acgttttcac acttctagta 9181 agcctctacc tgcacgacaa cacataatga cccaccaatc acatgcctat catatagtaa G9804A (underlined)

9541 taggagggca ctggccccca acaggcatca ccccgctaaa tcccctagaa gtcccactcc (SEQ ID NO: 38)

9601 taaacacatc cgtattactc gcatcaggag tatcaatcac ctgagctcac catagtctaa 9661 tagaaaacaa ccgaaaccaa ataattcaag cactgcttat tacaatttta ctgggtctct 9721 attttaccct cctacaagcc tcagagtact tcgagtctcc cttcaccatt tccgacggca 9781 tctacggctc aacatttttt gtagccacag gcttccacgg acttcacgtc attattggct 9841 caactttcct cactatctgc ttcatccgcc aactaatatt tcactttaca tccaaacatc 9901 actttggctt cgaagccgcc gcctgatact ggcattttgt agatgtggtt tgactatttc -continued G11778A (underlined)

```
11641  agccctcgta gtaacagcca ttctcatcca aaccccctga agcttcaccg gcgcagtcat  (SEQ ID NO: 39)

11701  tctcataatc gcccacgggc ttacatcctc attactattc tgcctagcaa actcaaacta

11761  cgaacgcact cacagtcgca tcataatcct ctctcaagga cttcaaactc tactcccact

11821  aatagctttt tgatgacttc tagcaagcct cgctaacctc gccttacccc ccactattaa

11881  cctactggga gaactctctg tgctagtaac cacgttctcc tgatcaaata tcactctcct

11941  acttacagga ctcaacatac tagtcacagc cctatactcc ctctacatat ttaccacaac

12001  acaatggggc tcactcaccc accacattaa caacataaaa ccctcattca cacgagaaaa
```

EXAMPLE 3

Gene Polymorphisms of the Renin-Angiotensin Aldosterone System Associate with Risk for Developing Primary Open-Angle Glaucoma and Normal-Tension Glaucoma Purpose: Multiple environmental and genetic factors may be involved in pathogenesis of glaucoma. To predict genetic risk of glaucoma, an association study in gene polymorphisms of the renin-angiotensin-aldosterone (R-A-A) system was performed.

Materials and Methods

Patients and Control Study Subjects

A total of 551 blood samples were collected at seven institutes in Japan. They were 162 POAG patients, 193 NTG patients, and 196 normal subjects, and none of the subjects was related to others in this study.

The average age at examination was 58.8±13.7 years in NTG, 62.0±15.4 years in POAG, and 71.2±10.4 years in normal subjects. The average age of the normal control subjects is significantly higher than NTG patients ($p<0.001$) or POAG patients ($p<0.001$), respectively. This could reduce the possibility that a subset will eventually develop glaucoma. The familial history was recorded in 66 (34.2%) out of 127 NTG patients and 49 (30.2%) out of 113 POAG patients. Male patients were 89 (46.1%) in NTG and 87 (53.7%) in POAG, and 77 (39.3%) in normal subjects.

One hundred ninety-six Japanese control samples were obtained from individuals who had no known eye abnormalities except cataract. These subjects were older than 40 years with IOP below 21 mmHg, no glaucomatous disc change, and no family history of glaucoma.

Genotyping

Seven genes and 10 polymorphisms in the R-A-A system were determined for each subject with glaucoma or normal Japanese control with renin (REN) 18-83G>A (Frossard P M et. al., Hypertens Res 1998; 21:221-225, the contents of the cited reference are herein incorporated by reference), angiotensin II type 1 receptor (AT1R) 1166A>C, −521C>T, −713T>G (Nalogowska-Glosnicka K et. al., Med Sci Monit 2000; 6:523-529 and Erdmann J et. al., Ann Hum Genet 1999; 63:369-374, the contents of the cited reference are herein incorporated by reference), angiotensin II type 2 receptor (AT2R) 3123C>A (Katsuya T et. al., Mol Cell Endocrinol 1997; 127:221-228, the contents of the cited reference are herein incorporated by reference), cytochrome P45011B1 (CYP11B1) −344T>C (Tsujita Y et. al., Hypertens Res 2001; 24:105-109, the contents of the cited reference are herein incorporated by reference), and chymase (CYM) 3123C>A, were identified using by polymerase chain reaction-restriction fragment length polymorphism (PCR-RFLP). The angiotensin-converting enzyme (ACE) insertion/deletion (I/D) was determined only by PCR and agarose gel electrophoresis. To avoid the false determination of ACE/ID polymorphism, I allele specific amplification was carried out following the protocol of Lindpaintner et al (N Engl J Med 1995; 332: 706-711, the contents of the cited reference are herein incorporated by reference). Genomic DNA was isolated from peripheral blood lymphocytes by phenol-chloroform extraction. The primer sets and restriction enzymes used were listed in Table 6.

TABLE 6

Primer pair sequences used for PCR amplification and restriction enzymes of polymorphic sites in renin angiotensin system

| Gene | Polymorphism | Primer sequences | Annealing temp | Product size | Restriction enzyme | Digested products | |
|---|---|---|---|---|---|---|---|
| REN | I8-83G > A | TGAGGTTCGAGTCGGCCCCCT | 68° C. | 250 bp | MboI | G: 250 bp | (SEQ ID NO: 40) |
| | | TCGCCAAACATGGCCACACAT | | | | A: 171 + 79 bp | (SEQ ID NO: 41) |
| ACE | I/D 1st step | GCCCTGCAGGTGTCTGCAGCATGT | 63° C. | D: 319 bp | | | (SEQ ID NO: 42) |
| | | GGATGGCTCTCCCCGCCTTGTCTC | | I: 597 bp | | | (SEQ ID NO: 43) |
| | 2nd step | TCCCAGCACACCCCCCCCCACTAC | 67° C. | D/D: no product | | | (SEQ ID NO: 44) |
| | | TCGCCAGCCCTCCCATGCCCATAA | | I: 335 bp | | | (SEQ ID NO: 45) |
| AT1 | 1166A > C | GAGGTTGAGTGACATGTTCGAAAC | 60° C. | 253 bp | DdeI | A: 253 bp | (SEQ ID NO: 46) |
| | | CGTCATCTGTCTAATGCAAAATGT | | | | C: 155 + 98 bp | (SEQ ID NO: 47) |
| | −521C > T | CGTGATGTCTTTATCTGGTTTTG | 60° C. | 270 bp | SspI | C: 270 bp | (SEQ ID NO: 48) |
| | | CGAACTTTGGTAATACAGTTGTGG | | | | T: 144 + 126 bp | (SEQ ID NO: 49) |
| | −713T > G | AAACTACAGTCACCCTACTCACCT | 55° C. | 292 bp | HinfI | T: 170 + 122 bp | (SEQ ID NO: 50) |
| | | TTCTTCACAAACTCTTCCAA | | | | G: 292 bp | (SEQ ID NO: 51) |

TABLE 6-continued

Primer pair sequences used for PCR amplification and restriction enzymes of polymorphic sites in renin angiotensin system

| Gene | Polymorphism | Primer sequences | Annealing temp | Product size | Restriction enzyme | Digested products | |
|---|---|---|---|---|---|---|---|
| AT2 | 3123C > A | GGATTCAGATTTCTCTTTGAA<br>GCATAGGAGTATGATTTAATC | 53° C. | 340 bp | AluI | C: 340 bp<br>A: 227 + 113 bp | (SEQ ID NO: 52)<br>(SEQ ID NO: 53) |
| CYP11B1 | -344C > T | CAGGAGGGATGAGCAGGCAGAGCACAG<br>CTCACCCAGGAACCTGCTCTGGAAACATA | 63° C. | 404 bp | HaeIII | C: 333 bp + 71 bp<br>T: 404 bp | (SEQ ID NO: 54)<br>(SEQ ID NO: 55) |
| CMA | -1903A > G | GGAAATGTGAGCAGATAGTGCAGTC<br>AATCCGGAGCTGGAGAACTCTTGTC | 51° C. | 285 bp | BstX1 | A: 285 bp<br>G: 195 + 90 bp | (SEQ ID NO: 56)<br>(SEQ ID NO: 57) |

The genotyping angiotensinogen (AGT) T174M, M235T was determined using by Invader Assay® (Lyamichev V et. al., Nat Biotechnol 1999; 17:292-296, the contents of the cited reference are herein incorporated by reference).

Results

Genotype Distribution of R-A-A System in Japanese Population

Of 10 polymorphisms in R-A-A system, two showed a significantly difference in frequencies of genotypes: AT1R/−713T>G for POAG, and AT2/3123C>A for NTG (Table 7). A 3123C>A polymorphism was associated with only female patients with NTG.

A frequency of homozygous G genotype (GG) in AT1R/−713T>G polymorphism was significantly higher (p=0.04 for TT+TG v GG) in POAG patients (4.2%) than in controls (0.5%). A frequency of CA+AA genotypes in AT2R/3123C>A polymorphism was significantly higher (p=0.011 for CC v CA+AA) in female patients with NTG (70.8%) than in female controls (55.0%).

TABLE 7

Association between glaucoma (POAG and NTG) and gene polymorphism of the renin-angiotensin aldosterone system.

| Gene | Gene Polymorphism | | Genotype Frequency | | p |
|---|---|---|---|---|---|
| | | | TT + TG | GG | |
| AT1 | −713T > G | POAG (n = 165) | 158 (95.8%) | 7 (4.2%) | 0.04 |
| | | NTG (n = 208) | 208 (100%) | 0 (0.0%) | |
| | | Control (n = 198) | 197 (99.5%) | 1 (0.5%) | |
| | | | CC | CA + AA | |
| AT2 | 3123C > A (Female) | POAG (n = 79) | 34 (43.0%) | 45 (56.0%) | |
| | | NTG (n = 120) | 35 (29.2%) | 85 (70.8%) | 0.011 |
| | | Control (n = 111) | 54 (45.0%) | 66 (55.0%) | |

Association Between Two Promoter Polymorphisms in AT1R in POAG Patients

A frequency of POAG carriers with combined homozygous −521T and homozygous −713G (4.2%) was significantly higher (p=0.011) than that of normals (0%) (Table 8-1). Only POAG patients, neither NTG nor normal subjects, had this genotype.

TABLE 8-1

Distribution of genotypes of AT1R −521T allele and −713G allele

| Group | A | B | p |
|---|---|---|---|
| POAG (n = 165) | 7 (4.2%) | 158 (95.8%) | 0.011 |
| NTG (n = 208) | 0 (0.0%) | 208 (100.0%) | |
| Control (N = 198) | 0 (0.0%) | 198 (100.0%) | |

A: Subjects with two −521 alleles and two −713G alleles
B: Subjects not satisfying the criteria for Group A.

These results indicated that gene polymorphism of the renin-angiotensin aldosterone system is one of important genetic risk factors for development of glaucoma. Detection of AT1R/−731T>G polymorphisms makes possible the early diagnosis and early treatment of POAG. Especially, specific genotype of combined homozygous −521T and homozygous −713G in the AT1R gene is useful for the early diagnosis of POAG. Detection of the AT2R/3123C>A polymorphisms make possible the early diagnosis and early treatment of female patient with NTG.

Clinical Characteristics of NTG Patients with AT2R 3123C>A Polymorphism and ACE I/D Polymorphism The clinical features recorded in the glaucoma patients were age at diagnosis, untreated maximum IOP (defined as IOP at diagnosis), and visual field defects at the initial examination (defined as visual field defects at diagnosis. The severity of the visual field defects was scored from 1 to 5. Data obtained with different perimeters were combined using a five-point scale defined as follows: 1=no alteration; 2=early defect; 3=moderate defect; 4=severe defect; and 5=light perception only or no vision. Field defects were judged to be early, moderate, or severe according to Kozaki's classification based on the results of Goldmann perimetry or the classification used for the Humphrey field analyzer. The former classification is most widely used in Japan.

Significant association of the clinical characteristics of visual field score was detected between male glaucoma patients with AT2R genotype. Visual field score in male POAG patients with C genotype had worse than those with A genotype (P=0.04, Table 8-2). No significant association of the clinical characteristics (age, IOP, and visual field score) was detected between female glaucoma patients with C/C and those with C/A+A/A genotypes. The visual field score had a tendency to be worse in NTG patients with C/C genotype than those with C/A+A/A genotypes (P=0.165).

However, when combined with ACE insertion/deletion polymorphism, female patients with NTG who carried C/C in the AT2R gene as well as ID+DD in the ACE gene had significantly worse visual field scores than the other three combined genotypes (P=0.012; Table 8-3, FIG. 1).

TABLE 8-2

Comparison of Clinical characteristics of male glaucoma patients according to AT2R genotypes

| AT2 3123G > A Male Phenotype | Phenotype Variable | C | A | P value* |
|---|---|---|---|---|
| POAG | Age at diagnosis (ys) | 57.0 ± 10.9 (n = 62) | 56.9 ± 14.0 (n = 46) | 0.808 |
| | IOP at diagnosis (mmHg) | 26.8 ± 6.7 (n = 55)) | 27.5 ± 6.7 (n = 43) | 0.522 |
| | Visual field score at diagnosis | 3.27 ± 0.96 (n = 62) | 2.89 ± 0.74 (n = 46) | 0.015 |

*P value for logistic regression analysis

TABLE 8-3

Comparison of clinical characteristcs of female patients with NTG according to ACE genotypes (Insertion/deletion) and AT2R genotypes (3123C > A)

| | ACE | I/I | | I/D + D/D | | |
|---|---|---|---|---|---|---|
| Clinical characteristcs | AT2R | C/C | C/A + A/A | C/C | C/A + A/A | P |
| Age at diagnosis (ys) | | 63.6 ± 10.9 (n = 15) | 57.0 ± 11.2 (n = 47) | 56.2 ± 14.1 (n = 23) | 58.5 ± 12.0 (n = 51) | 0.313 |
| IOP at diagnosis (mm Hg) | | 16.0 ± 2.2 (n = 16) | 16.5 ± 2.6 (n = 43) | 16.1 ± 2.7 (n = 20) | 16.5 ± 2.2 (n = 49) | 0.75 |
| Visual field score at diagnosis | | 2.47 ± 0.51 (n = 17) | 2.64 ± 0.53 (n = 47) | 3.13 ± 0.76 (n = 23) | 2.65 ± 0.59 (n = 52) | 0.012† |

* P value tested by Kruskal-Wallis test
†P < 0.05

Partial nucleotide sequences of AT1R and AT2R genes containing the targeted polymorphism are as follows:

```
AT1R -713 (the underlined "t") T > G
1861 attactgtaa actacagtca ccctactcac ctatctaaca ttaattgatt tttggtaaac  (SEQ ID NO: 58)

1921 taatctaatc ttgctttctg gcatcaacct cacttgacca tggtgtatag tccctttcat

1981 atgttattgg atTcaatttg cctacatttt gttgagaatt tttatctata ctcttaagaa

2041 atattgatct gtagtctcgt gatgtcttta tctggttttg ttatcagggt gatactggcc

2101 tcatagcatg agttgggaga tcatccttac tcttctattt tttggaagag tttgtgaaga

2161 attgatatta tttcttcttt aaatatttat tgggttttta aaatacattt ttaaaatgca

AT2R 3123 (the underlined "c") C > A, the underlined
oligonucleotide sequences were used for primers
ggattcagatttctctttgaaacatgcttgtgtttcttagtggggttttatatccatttttatcaggatt  (SEQ ID NO: 59)

tcctcttgaaccagaaccagtctttcaactcattgcatcatttacaagacaacattgtaagagagatgag

cacttcttagttgagtatattataatagattagtactggattattcaggctttaggcatatgcttcttta

aaaacgctataaattatattcctcttgcatttcacttgagtggaggtttatagttaatctataactacat

attgaatagggctaggaatatagattaaatcatactcctatgc

(Based on GenBank accession No. AY536522, the AT2R 3123 corresponds
nucleotide number 4926)
4741 gtgtttctta gtggggtttt atatccattt ttttcaggat ttcctcttga accagaacca  (SEQ ID NO: 60)

4801 gtctttcaac tcattgcatc atttacaaga catcattgta agagagatga gcacttctaa
```

-continued

```
4861 gttgagtata ttataataga ttagtactgg attattcagg ctttaggcat atgcttcttt

4921 aaaaacgcta taaattatat tcctcttgca tttcacttga gtggaggttt atagttaatc

4981 tataactaca tattgaatag ggctaggaat attgattaaa tcatactcct atgctttagc

5041 ttatttttac agttatagaa agcaagatgt actataacat agaattgcaa tctataatat

5101 ttgtgtgttc actaaactct gaataagcac tttttaaaaa actttctact cattttaatg
```

EXAMPLE 4

Gene Polymorphisms of the Endothelin Gene Associate with Risk for Developing Normal-Tension Glaucoma Methods Patients A total of 605 blood samples were collected. There were 178 POAG patients, 214 NTG patients, and 213 normal controls, and none of the subjects was related to others in this study. Patients were considered to have POAG if they had a normal open-angle, a cup-disc ratio greater than 0.7 with typical glaucomatous visual field loss on either Goldmann or Humphrey perimetry, and the absence of ocular, rhinologic, neurological or systemic disorders which might be responsible for the optic nerve damage. Patients with NTG had an IOP of 21 mmHg or lower. Patients with exfoliative glaucoma, pigmentary glaucoma, and corticosteroid-induced glaucoma were excluded. Control samples were obtained from Japanese subjects who had no known eye abnormalities except for cataracts. These subjects had IOPs below 21 mm Hg, had normal optic discs, and no family history of glaucoma.

Detection of G/T Polymorphism of Endothelin (ET) Gene by Invader Assay

DNA was isolated from peripheral blood lymphocytes by standard methods of phenol-chloroform extraction, and G/T polymorphism (Lys/lys, Lys/Asn and Asn/Asn) at codon 198 in exon 5 of ET gene was determined by the Invader® assay. The primary probes (wild and mutant probes) and Invader® oligonucleotides (Invader® probe) used to detect the G/T polymorphism of ET gene are shown in Table 9.

Invader® assay FRET-detection 96-well plates (Third Wave Technologies, Inc, Madison, Wis.) contains the generic components of an Invader® assay (Cleavase® enzyme VIII, FRET probes, MOPS buffer, and polyethylene glycol) dried in each of the individual wells. In brief, 8 μl of the primary probe/Invader®/mixture and total DNA (10 ng) samples were added to each well of a 96-well plate, and were denatured by incubation at 95° C. for 10 min. After 15 μl of mineral oil (Sigma, St. Louis, Mo.) was overlaid on all reaction wells, the plate was incubated isothermally at 63° C. for 2 hours in a PTC-100 thermal cycler (MJ Research, Waltham, Mass.) and then kept at 4° C. until fluorescence measurements. The fluorescence intensities were measured on a CytoFlour 4000 fluorescence plate reader (Applied Biosystems, Foster City, Calif.) with excitation at 485 nm/20 nm (wavelength/bandwidth) and emission at 530 nm/25 nm for FAM dye; excitation at 560 nm/20 nm and emission at 620 nm/40 nm for Redmond RED (RED) dye. Each sample was tested in duplicate in the same plate and two fluorescence measurements were performed in each plate. Thus, four measurements were obtained for each sample and they were averaged.

Results

The genotype frequencies of G/T polymorphism (Lys/lys, Lys/Asn and Asn/Asn) at codon 198 in exon 5 of ET gene are presented in Table 10.

TABLE 9

| Mutation | nucleotide change | Target | Probe | Sequence | Tm | Dye | |
|---|---|---|---|---|---|---|---|
| EDN Ex5 GT | G to T | Sense | Wild | Flap sequence-CTTGCCTTTCAGCRTTGG | 64.6 | FAM | (SEQ ID NO: 61) |
| | | | Mutant | Flap sequence-ATTGCCTTTCAGCTTGG | 64.0 | RED | (SEQ ID NO: 62) |
| | | | Invader | GTTGTGGGTCACATAACGCTCTCTGGAGGGT | 76.9 | | (SEQ ID NO: 63) |

TABLE 10

The genotype frequency at codon 198 in exon 5 of ET gene

| Group | n | Genotype Frequency | | | p | Genotype Frequency | | p |
|---|---|---|---|---|---|---|---|---|
| | | Lys/lys | Lys/Asn | Asn/Asn | | Lys/lys | Lys/Asn + Asn/Asn | |
| Control | 213 | 94 (44.1%) | 93 (43.7%) | 26 (12.2%) | | 94 (44.1%) | 119 (55.9%) | |
| NTG | 214 | 120 (56.1%) | 72 (33.6%) | 22 (10.3%) | 0.046 | 120 (56.1%) | 94 (43.9%) | 0.014 |
| POAG | 178 | 82 (46.1%) | 77 (43.3%) | 19 (10.7%) | | 82 (46.1%) | 96 (53.9%) | |

These results indicated that Lys/Lys homozygote of ET-1 gene at codon 198 in exon 5 is one of the risk factor to develop or progress the NTG, and detection of the Lys/Lys homozygote makes possible the early diagnosis and early treatment of NTG.

Partial sequence of EDN1 comprising codon 198 is as follows:

```
EDN1 Codon 198 (underlined): aag (Lys) to aat (Asn)

9061 ttgaggtttt atcaaagagt tgcggcgggt ggtgaaagtt cacaaccaga ttcaggtttt(SEQ ID NO: 64)

9121 gtttgtgcca gattctaatt ttacatgttt cttttgccaa agggtgattt ttttaaaata

9181 acatttgttt tctcttatct tgctttatta ggtcggagac catgagaaac agcgtcaaat

9241 catctttca tgatcccaag ctgaaaggca agccctccag agagcgttat gtgacccaca

9301 accgagcaca ttggtgacag accttcgggg cctgtctgaa gccatagcct ccacggagag

9361 ccctgtggcc gactctgcac tctccaccct ggctgggatc agagcaggag catcctctgc

(tga is the translation termination codon)
```

EXAMPLE 5

Novel MYOC Gene Mutation, Phe369Leu, in Japanese Patients with Primary Open-Angle Glaucoma Detected by Denaturing High-Performance Liquid Chromatography Purpose: To screen for mutations in the MYOC gene in Japanese patients with primary open-angle glaucoma (POAG) using denaturing high-performance liquid chromatography (DHPLC).

Materials and Methods

Patients

Blood samples were collected from 171 POAG patients and 100 normal subjects at seven Japanese medical institutions. The subjects were unrelated, and their mean age at the time of examination was 55.1±16.0 (±standard deviation) years for the patients with POAG and 70.5±10.6 years for the normal subjects. We purposely selected older control subjects to reduce the probability that a subset of them would develop glaucoma.

A detailed family history was obtained by interviews in 55 POAG patients (32.2%). There were 91 men (53.2%) in the POAG patients, and 41 men (41.0%) in the normal subjects.

DNA Extraction and PCR Conditions

Genomic DNA was isolated from peripheral blood lymphocytes by standard methods. The seven exonic regions of the MYOC gene were amplified by polymerase chain reaction (PCR) using the primer sets listed in Table 11. For high-throughput analysis of the patients, samples from three patients were pooled. The PCR reaction was performed with a thermal cycler (iCycler; Bio Rad, Hercules, Calif.) in a total volume of 25 μl. The PCR conditions were: denaturation at 95° C. for 9 min; followed by 35 cycles at 95° C. for 1 min; 58° C. for 30 sec (Table 1); and 72° C. for 1.5 min; a final extension step was then carried out at 72° C. for 7 min. For heteroduplex formation, each PCR product (25 μl) was denatured at 95° C. for 5 min and gradually cooled to 25° C.

For analyses of a few samples, each of seven exonic regions was amplified simultaneously by PCR in a 96-well plate (96-well Multiplate, MLP-9601; MJ Research, Waltham, Mass.). Seven wells were used for each patient. Primer sets were designed to be effective using a single annealing temperature of 58° C. (Table 11).

TABLE 11

Primer sequences, product size, and PCR annealing and DHPLC analysis temperatures

| Exon | Primer sequences (5' to 3') | Product size (bp) | PCR Tm (° C.) | DHPLC Tm (° C.) | |
|---|---|---|---|---|---|
| 1A | F AGC ACA GCA GAG CTT TCC AGA GGA | 302 | 58.0 | 61.9 | (SEQ ID NO: 65) |
| | R CTC CAG GTC TAA GCG TTG G | | | | (SEQ ID NO: 66) |
| 1B | F CAG GCC ATG TCA GTC ATC CA | 298 | 58.0 | 61.2, 64.5 | (SEQ ID NO: 67) |
| | R TCT CAT TTT CTT GCC TTA GTC | | | | (SEQ ID NO: 68) |
| 1C | F GAA ACC CAA ACC AGA GAG | 255 | 58.0 | 61.0, 63.5 | (SEQ ID NO: 69) |
| | R ATA TCA CCT GCT GAA CTC AGA GTC | | | | (SEQ ID NO: 70) |
| 2A | F CCT CAA CAT AGT CAA TCC TTG GGC | 245 | 58.0 | 56.3, 59.3 | (SEQ ID NO: 71) |
| | R ACA TGA ATA AAG ACC ATG TGG GCA | | | | (SEQ ID NO: 72) |
| 3A | F GAT TAT GGA TTA AGT GGT GCT TCG | 375 | 58.0 | 59.3, 61.3, 62.3 | (SEQ ID NO: 73) |
| | R TGT CTC GGT ATT CAG CTC AT | | | | (SEQ ID NO: 74) |
| 3B | F CAT ACT GCC TAG GCC ACT GGA | 337 | 58.0 | 60.9, 61.4 | (SEQ ID NO: 75) |
| | R ATT GGC GAC TGA CTG CTT AC | | | | (SEQ ID NO: 76) |
| 3C | F GAA TCT GGA ACT CGA ACA AA | 333 | 58.0 | 59.7, 61.7 | (SEQ ID NO: 77) |
| | R CTG AGC ATC TCC TTC TGC CAT | | | | (SEQ ID NO: 78) |

Denaturing HPLC Analysis

For high-throughput analysis, a 25 μl volume of PCR products from the three patients was automatically injected into the chromatograph for analysis using the WAVE® System for DHPLC analysis (Transgenomic, Omaha, Nebr.). The DHPLC melting temperatures are listed in Table 1. For analysis of a small number of samples, following 96-well-plate PCR, the plate was next placed in a WAVE® System programmed to automatically analyze each well at two to three melting temperatures. Approximately 3 hrs was sufficient time to analyze one individual's sample.

When abnormal chromatographic patterns were detected in the pooled samples by the high-throughput protocol, the sample was reanalyzed individually in the WAVE® System. The PCR product that showed the abnormal chromatographic pattern was then sequenced.

Direct DNA Sequencing

For direct sequencing, PCR products were purified with a QIA Quick PCR purification kit (Qiagen, Valencia, Calif.) to remove unused primers and precursors. The PCR products were directly sequenced with the same forward and reverse PCR amplification primers on an ABI310 automated sequencer using BigDye chemistry according to the manufacturer's recommended protocol (Applied Biosystems, Foster City, Calif.).

Results

Screening of Pools of DNA in 171 Patients

Figure 2:
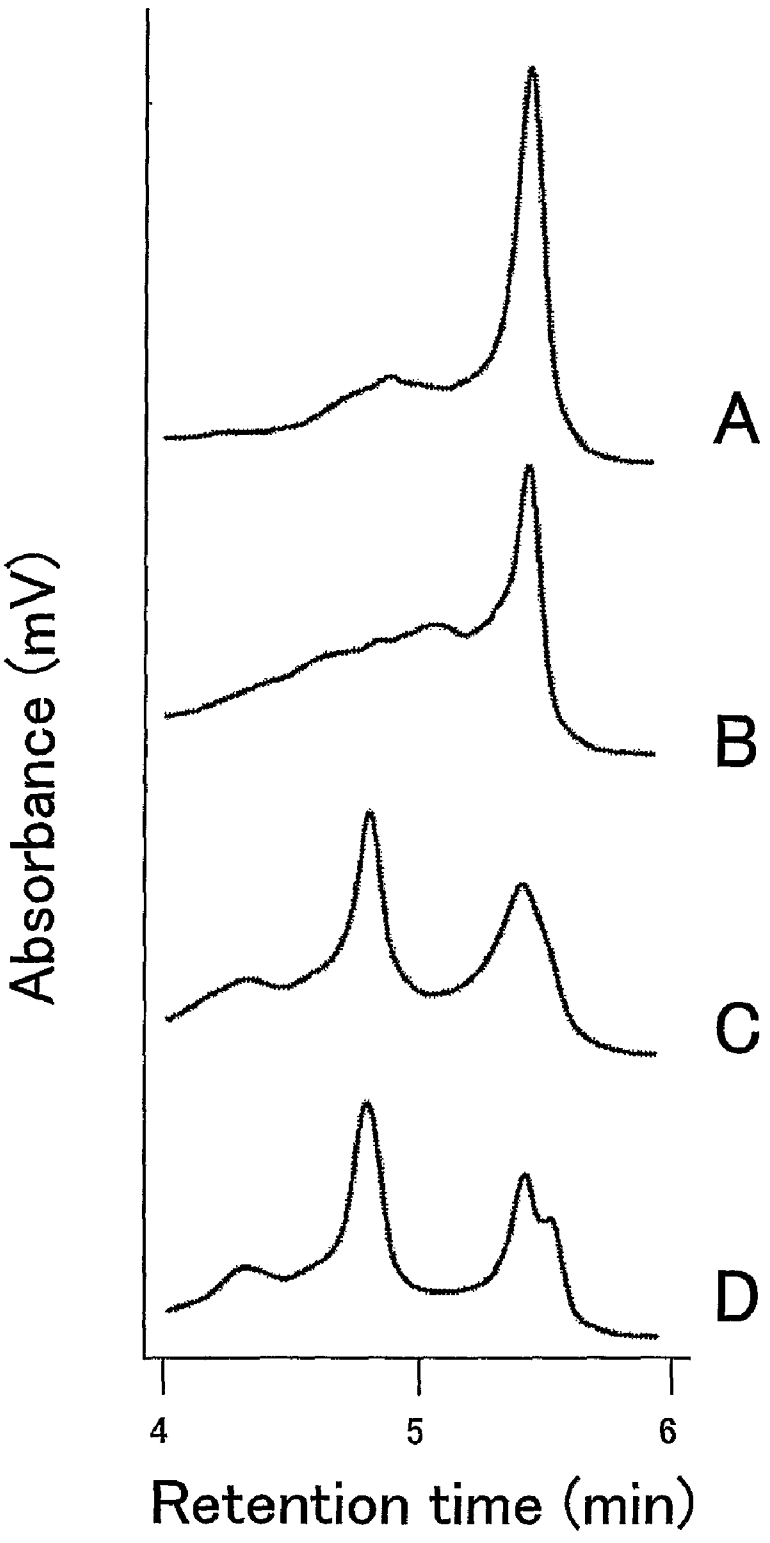
FIG. 2 represents DHPLC tracing patterns in the Exon3C of the MYOC gene.

Four DHPLC tracing patterns in the Exon3C region were shown in FIG. 2. The upper most pattern (A) has a normal appearance, while the middle pattern (B) showed a broad shoulder, and the lower patterns (C and D) had a characteristic double peak pattern indicative of sequence variations in this region. Sequencing analysis of samples B, C, and D revealed Thr448Pro, Pro481Ser, and Ala488Ala mutations (Table 12).

Figure 3:
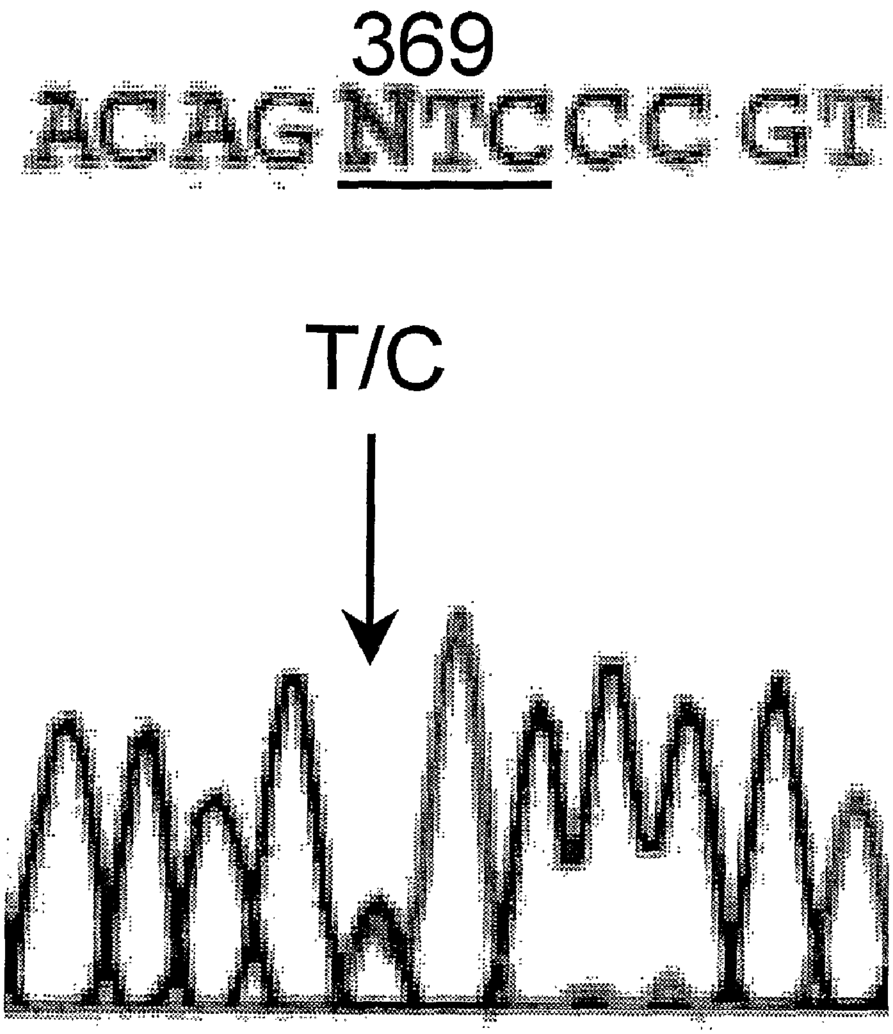
FIG. 3 represents novel missense mutation, Phe369Leu detected in exon 3 of the MYOC gene. Sequencing data depicting the mutation is shown (SEQ ID NO: 210).

Four glaucoma-causing mutations were identified in 5 (2.9%) of 171 patients with POAG. In addition, eight polymorphisms and five synonymous codon changes were identified (Table 12). One novel missense mutation, Phe369Leu detected in exon 3 (FIG. 3) was not present in 100 normal Japanese subjects. The three other missense mutations, Ile360Asn, Ala363Thr, and Thr448Pro have been reported in Japanese patients with POAG.

TABLE 12

MYOC mutations and polymorphisms in patients with POAG and controls

| | Exon | Sequence change | Amino acid change | Frequency patients | Frequency controls |
|---|---|---|---|---|---|
| Mutations | 3 | c.1079T > A | Ile360Asn | 1/171 | 0/100 |
| | 3 | c.1087G > A | Ala363Thr | 2/171 | 0/100 |
| | 3 | c.1105T > C | Phe369Leu* | 1/171 | 0/100 |
| | 3 | c.1342A > C | Thr448Pro | 1/171 | 0/100 |
| Polymorphisms | 1 | c.34G > C | Gly12Arg | 1/171 | 2/100 |
| | 1 | c.57G > T | Gln19His | 1/171 | 1/100 |
| | 1 | c.136C > T | Arg46Stop | 1/171 | 1/100 |
| | 1 | c.210C > T | Val70Val† | 2/171 | 0/100 |
| | 1 | c.227G > A | Arg76Lys | 14/171 | 9/100 |
| | 1 | c.369C > T | Thr123Thr | 1/171 | 0/100 |
| | 1 | c.473G > A | Arg158Gln | 1/171 | 1/100 |
| | 2 | c.611C > T | Thr204Met | 0/171 | 1/100 |
| | 2 | c.624C > G | Asp208Glu | 5/171 | 2/100 |
| | 3 | c.864C > T | Ile288Ile | 1/171 | 0/100 |
| | 3 | c.1110G > A | Pro370Pro | 0/171 | 1/100 |
| | 3 | c.1441C > T | Pro481Ser | 1/171 | 0/100 |
| | 3 | c.1464C > T | Ala488Ala | 3/171 | 1/100 |

*Novel myocilin mutation;
†novel myocilin polymorphism.

Screening of Individual Patients by Plate PCR Followed by DHPLC

Figure 4:
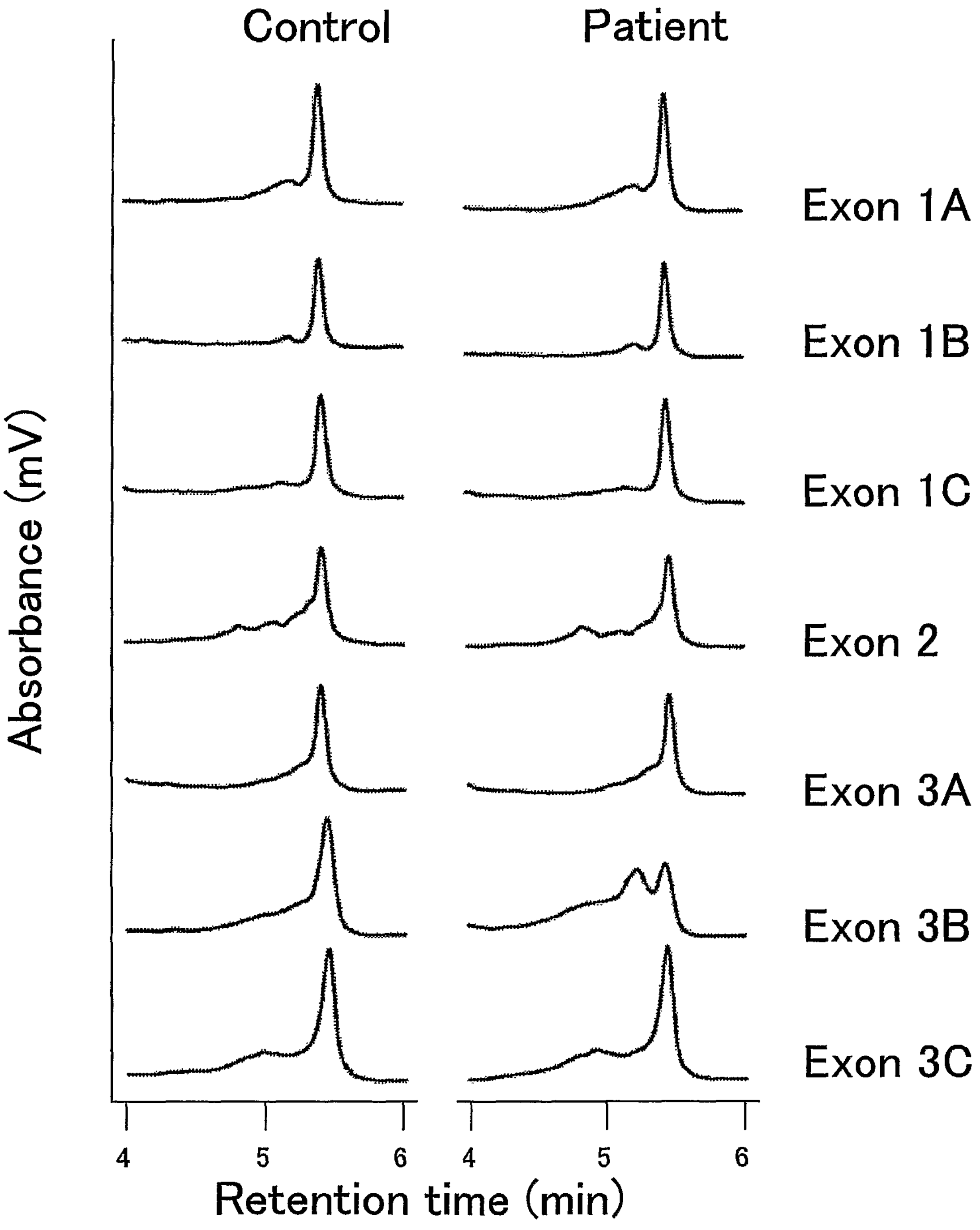
FIG. 4 represents a DHPLC tracing of MYOC gene from a patient with POAG.

A DHPLC tracing from a patient with POAG is shown in FIG. 4. In the exon3B region, an abnormal tracing indicative of sequence variation can be seen, which proved to represent a Phe369Leu mutation on direct sequencing.

Partial nucleotide sequences for MYOC exon 3 gene containing the targeted polymorphism is as follows:

```
MYOC Exon 3, codon 369(underlined) TTC(Phe) to CTC(Leu)
301 actggaaagc acgggtgctg tggtgtactc ggggagcctc tatttccagg gcgctgagtc  (SEQ ID NO: 79)

361 cagaactgtc ataagatatg agctgaatac cgagacagtg aaggctgaga aggaaatccc

421 tggagctggc taccacggac agttcccgta ttcttggggt ggctacacgg acattgactt

481 ggctgtggat gaagcaggcc tctgggtcat ttacagtacc gatgaggcca aaggtgccat

541 tgtcctctcc aaactgaacc cagagaatct ggaactcgaa caaacctggg agacaaacat
```

The nucleotide sequences of MYOC exon 1-3 are available from GenBank, Accession Nos. AB006686-AB006688

EXAMPLE 6

Variants in Optineurin Gene and their Association with Tumor Necrosis Factor-α Polymorphisms in Japanese Patients with Glaucoma Purpose: To investigate sequence variations in the optineurin (OPTN) gene and their association with TNF-α polymorphism in Japanese patients with glaucoma.

Subjects and Methods

Patients and Control Subjects

A total of 629 blood samples were collected at seven institutions in Japan. There were 194 POAG patients, 217 NTG patients, and 218 normal controls, and none of the subjects was related to others in this study. The patients whose age at diagnosis was less than 35 years and patients with over −5.5 D of myopia were excluded. POAG patients with MYOC mutations were also excluded.

DNA Extraction and PCR Conditions

Genomic DNA was isolated from peripheral blood lymphocytes by phenol-chloroform extraction. The 13 exonic coding regions of the OPTN gene were amplified by polymerase chain reaction (PCR) using the primer sets listed in Table 13. A 20-base GC-clamp was attached to some of the forward primers to detect mutations in the higher melting temperature domain by DHPLC analysis (Narayanaswami G et. al., Genet Test. 2001; 5:9-16). In high-throughput analysis, samples from three patients were pooled. PCR was performed with a thermal cycler (iCycler, Bio-Rad; Hercules, Calif.) in a total volume of 20 μl containing; 45 ng of genomic DNA, 2 μl GeneAmp 10×PCR buffer II, 2 μl of GeneAmp dNTP mix with a 2.0 mM concentration of each dNTP, 2.4 μl of a 25 mM $MgCl_2$ solution; 4 pmol of each primer, and 0.1 U of AmpliTaq Gold DNA polymerase (Applied Biosystems, Foster City, Calif.). PCR conditions were; denaturation at 95° C. for 9 min, followed by 35 cycles at 95° C. for 1 min, 55° to 60° C. for 30 sec (Table 13), and 72° C. for 1 min and 30 sec, and a final extension step at 72° C. for 7 min.

TABLE 13

Primer sequences, PCR product sizes, and PCR annealing and DHPLC analysis temperatures

| Exon | Primer Sequences (5' to 3') | PCR product size (bp) | PCR Tm (° C.) | DHPLC Tm (° C.) | |
|---|---|---|---|---|---|
| 4 | F CCAGTGGGTTTGTGGGACTCC | 317 | 60 | 61.7 | (SEQ ID NO: 80) |
| | R AAAGGGATGGCATTTCTTGCA | | | | (SEQ ID NO: 81) |
| 5 | F GTCCACTTTCCTGGTGTGTGACT | 277 | 55 | 58.7 | (SEQ ID NO: 82) |
| | R CAACATCACAATGGATCG | | | | (SEQ ID NO: 83) |
| 6 | F AGCCTTAGTTTGATCTGTTCATTCA | 293 | 60 | 57.0, 62.5 | (SEQ ID NO: 84) |
| | R GTTTCATCTTTCCAGGGGAGGCT | | | | (SEQ ID NO: 85) |
| 7 | F GC-clamp AATCCCTTGCATTTCTGTTTTT | 188 | 55 | 59.4, 61.4, 62.4 | (SEQ ID NO: 86) |
| | R GTGACAAGCACCCAGTGACGA | | | | (SEQ ID NO: 87) |
| 8 | F GC-clamp GGTTACTCTCTTCTTAGTCTTTGGA | 320 | 57 | 54.6, 58.5 | (SEQ ID NO: 88) |
| | R GGGTGAACTGTATGGTATCTTAATT | | | | (SEQ ID NO: 89) |
| 9 | F GC-clamp GCTATTTCTCTTAAAGCCAAAGAGA | 242 | 55 | 57.4, 59.4 | (SEQ ID NO: 90) |
| | R CAGTGGCTGGACTACTCTCGT | | | | (SEQ ID NO: 91) |
| 10 | F GC-clamp GTCAGATGATAATTGTACAGATAT | 227 | 55 | 57.8, 59.8 | (SEQ ID NO: 92) |
| | R AATGTATATTTCAAAGGAGGATAAA | | | | (SEQ ID NO: 93) |
| 11 | F CCACTGCGACGTAAAGCAGCA | 286 | 60 | 57.5, 59.5 | (SEQ ID NO: 94) |
| | R CAAATCCGAATTCCAATCTGTATAA | | | | (SEQ ID NO: 95) |
| 12 | F GC-clamp GGTTGGGAGGCAAGACTATAAGTT | 233 | 60 | 55.5, 56.5 | (SEQ ID NO: 96) |
| | R TTCTGTTCATTACTAGGCTATGGAA | | | | (SEQ ID NO: 97) |
| 13 | F CAGGCAGAATTATTTCAAAACCAT | 264 | 60 | 58.9, 61.9 | (SEQ ID NO: 98) |
| | R CGAGAATACAGTCAGGGCTGG | | | | (SEQ ID NO: 99) |
| 14 | F GCACTACCTCCTCATCGCATAAACA | 260 | 60 | 56.7, 59.7 | (SEQ ID NO: 100) |
| | R GGCCATGCTGATGTGAGCTCT | | | | (SEQ ID NO: 101) |

TABLE 13-continued

Primer sequences, PCR product sizes, and PCR annealing and DHPLC analysis temperatures

| Exon | Primer Sequences (5' to 3') | PCR product size (bp) | PCR Tm (° C.) | DHPLC Tm (° C.) | |
|---|---|---|---|---|---|
| 15 | F GC-clamp GGACTGTCTGCTCAGTGTTGTCA | 282 | 60 | 56.0, 59.0, 61.0 | (SEQ ID NO: 102) |
| | R GGTGCCTTGATTTGGAATCCA | | | | (SEQ ID NO: 103) |
| 16 | F GC-clamp CACAACTGCCTGCAAAATGGAACT | 294 | 60 | 61.7 | (SEQ ID NO: 104) |
| | R GAGGCAAAATATTTGAGTGAAAACA | | | | (SEQ ID NO: 105) |

GC-clamp: CGCCCGCCGCCGCCCGCCGC

Denaturing HPLC Analysis

DHPLC analysis was performed using the WAVE® SYSTEMS (Transgenomic, Omaha, Nebr.). For heteroduplex formation, products of each PCR (20 μl) were denatured at 95° C. for 5 min and gradually cooled to 25° C. The annealed PCR products from the three mixed samples were automatically injected into a DNASep® cartridge (Transgenomic, Omaha, Nebr.).

Buffer A (Transgenomic, Omaha, Nebr.) was made up of 0.1 M triethylammonium acetate (TEAA), and Buffer B of 0.1 M TEAA and 25% acetonitrile. Analysis was carried out at a flow rate of 0.9 ml/min and the Buffer B gradient increased by 2%/min for 4.5 min. Elution of DNA fragments from the cartridge was detected by absorbance at 260 nm. The temperatures used for the analysis were selected according to the sequences of the DNA fragments. The WAVEMAKER software (v.4.1, Transgenomic, Omaha, Nebr.) predicted the melting behavior of the DNA fragments at various temperatures. The predicted melting domains within the DNA fragment determined the temperatures for the DHPLC analysis (Table 13). When abnormal chromatographic patterns were detected in a pool of three samples, each of the three samples was re-analyzed individually in the WAVE® SYSTEM. Then, the PCR product that showed an abnormal chromatographic pattern was sequenced. Once a correlation between abnormal chromatographic patterns and base changes was confirmed by direct sequencing analysis, additional sequencing analyses were not performed when any of the known abnormal chromatographic patterns were observed in the DHPLC analysis.

Direct DNA Sequencing

To detect mutations by direct sequencing, the PCR products were first purified with the QIAquick PCR Purification Kit (QIAGEN, Valenica, Calif., USA) to remove unreacted primers and precursors. The sequencing reactions were then performed using the ABI PRISM BigDye Terminator (v.3.1) Cycle Sequencing Kit, according to the manufacturer's protocol (Applied Biosystems). The data were collected by the ABI PRISM 310 Genetic Analyzer and analyzed by the ABI PRISM sequencing analysis program (v.3.7).

Genotyping OPTN c.412G>A (Thr34Thr) Polymorphism

The G to A substitution at position c.412 in exon 4 of the OPTN gene was detected by using restriction enzyme, $HpyCH_4IV$ (New England BioLabs, Beverly, Mass.), with the same primers listed in Table 13 for the DHPLC analysis. The G allele sequence was cut into two fragments (188 bp+129 bp) by $HpyCH_4IV$, while the A allele sequence remained intact (317 bp). The polymorphism was confirmed by restriction-enzyme assay and the chromatographic pattern of DHPLC.

Genotyping OPTN c.603T>A (Met98Lys) Polymorphism

The T to A substitution at position c.603 in exon 5 of the OPTN gene was detected by restriction enzyme, Stu I (TaKaRa, Shiga, Japan), using the same primers as for the DHPLC analysis (Table 13). The A allele sequence was cut into two fragments (175 bp+102 bp) by Stu I, while the T allele sequence remained intact (277 bp). The polymorphism was confirmed by restriction-enzyme assay and the chromatographic pattern of DHPLC.

Genotyping OPTN c.1944G>A (Arg545Gln) Polymorphism

The G to A substitution at position c.1944 in exon of the OPTN gene was analyzed by the Invader assay provided by the Research Department of R&D Center, BML (Saitama, Japan). The polymorphism was confirmed by Invader® assay and by the chromatographic pattern of DHPLC.

Genotyping TNF-α −308G>A Polymorphism

Genotyping the −308G>A polymorphism in the TNF-α promoter region was performed by using restriction enzyme NcoI (New England BioLabs, Beverly, Mass.), with the forward primer, 5'-AGGCAATAGGTTTTGAGGGCCAT-3' (SEQ ID NO:106), and the reverse primer, 5'-GTAGTGGGCCCTGCACCTTCT-3'(SEQ ID NO:107). The forward primer contained one nucleotide mismatch (bold and underlined), which allowed the use of the restriction enzyme. The G allele sequence was cut into two fragments (192 bp+20 bp) by NcoI while the A allele sequence remained intact (212 bp).

Genotyping TNF-α −857C>T Polymorphism

Genotyping the −857C>T polymorphism in the TNF-α promoter region was performed by using restriction enzyme HincII (TaKaRa, Shiga, Japan), with the forward primer, 5'-AAGTCGAGTATGGGGACCCCCCGTTAA-3' (SEQ ID NO:108), and the reverse primer, 5'-CCCCAGTGTGTGGCCATATCTTCTT-3' (SEQ ID NO:109). The forward primer contained one nucleotide mismatch (bold and underlined), which allowed the use of the restriction enzyme. The C allele sequence was cut into two fragments (106 bp+25 bp) by HincII, while the T allele sequence remained intact (131 bp).

Transcriptional activity of the −857T allele was significantly greater than that of −857C allele.

Genotyping TNF-α −863C>A Polymorphism

Genotyping the −863C>A polymorphism in the TNF-α promoter region was done by using restriction enzyme EcoNI (New England BioLabs, Beverly, Mass.) with the forward primer, 5'-GCTGAGAAGATGAAGGAAAAGTC-3' (SEQ ID NO:110), and the reverse primer, 5'-CCTCTACATGGC-CCTGTCCT-3' (SEQ ID NO:111). The reverse primer contained one nucleotide mismatch (bold and underlined), which allowed the use of the restriction enzyme. The C allele sequence was cut into two fragments (183 bp+23 bp) by EcoNI, while the A allele sequence remained intact (206 bp). Transcriptional activity of the −863A allele was significantly greater than that of −863C allele.

Statistical Analyses

The frequencies of the genotypes and alleles in patients and controls were compared with the chi-square test and Fisher's exact test. The odds ratio and 95% confidence intervals (CI) also were calculated. The Hardy-Weinberg equilibrium for the observed frequencies was also calculated. Comparisons of the clinical characteristics between the two groups were performed using Mann-Whitney U test or Student's unpaired t-test when appropriate. Logarithmic transformation was performed on skewed distribution clinical data which were the IOP at diagnosis of POAG, visual field score at diagnosis of NTG, and POAG to obtain a normal distribution for performing analysis of variance (ANOVA). One-way ANOVA was used to compare three clinical characteristics among patients with 4 different combinations of the TNF-α/−857C>T and optineurin/412G>A genotypes, or the TNF-α/−863C>A and optineurin/603T>A genotypes (see Table 17).

Statistical analysis was performed with SPSS program (SPSS Inc., Chicago, USA). A P value of <0.05 was considered to be significant.

Results

OPTN Variants in Japanese Subjects

A total of 629 Japanese subjects were studied, and the results are presented in Table 14.

Seventeen sequence changes were identified in the glaucoma patients and control subjects. Among these, three were missense changes, one was a deletion of one amino acid residue, four were synonymous codon changes, and nine were changes in noncoding sequences. One possible disease causing-mutation, His26Asp, was identified in one POAG proband and was not present in the 218 normal Japanese controls. Her brother aged 55 harbored the mutation and was diagnosed as NTG. Her brother's daughter aged 23 also had the mutation and showed cupping of the optic nerve head with a cup/disk ratio of 0.7 with no sign of visual field defect by Humphrey perimetry.

A deletion of Leu47 (3-bp deletion, CTC) was found in 1 control. A Met98Lys was identified in 33 POAG patients, NTG patients, and 36 controls, and an Arg545Gln was identified in 11 POAG patients, 15 NTG patients, and 11 controls.

Four synonymous nucleotide substitutions, c.412G>A (Thr34Thr), c.421G>A (Pro37Pro), c.457C>T (Thr49Thr), and c.2023C>T (His571His) were found. The Thr34Thr substitution was present in 69 (35.6%) POAG patients, 69 (31.8%) NTG patients, and 52 (23.9%) controls, and the Pro37Pro was found in 1 NTG patient. The Thr49Thr was identified in 1 POAG patient, and the His571H is was present in 2 controls.

Distribution of OPTN Variants in Japanese Subjects

The Thr34Thr (c.412G>A) polymorphism was significantly associated with POAG and NTG (Table 15). A significant association was found in patients with POAG (P=0.009 in genotype frequency: G/G vs G/A+A/A, and P=0.003 in allele frequency). No significant difference was detected between glaucoma patients and controls in either genotype or allele frequency for the Met98Lys (c.603T>A) or the Arg545Gln (c.1944G>A) polymorphisms. However, the Met98Lys polymorphism had a higher tendency to be associated with NTG than with POAG. The observed genotype frequencies were in agreement with those predicted by the Hardy-Weinberg equilibrium.

TABLE 14

OPTN variants observed in glaucoma patients and control subjects

| | Sequence | Codon | Frequency in Subjects (%) | | |
|---|---|---|---|---|---|
| Location | Changes | Changes | POAG | NTG | Control |
| Exon 4 | c.386C > G | His26Asp | 1/201 (0.5) | 0/232 (0) | 0/218 (0) |
| Exon 4 | c.449 − 451delCTC | Leu47del | 0/201 (0) | 0/232 (0) | 1/218 (0.5) |
| Exon 5 | c.603T > A | Met98Lys | 33/201 (16.4) | 50/232 (21.6) | 36/218 (16.5) |
| Exon 16 | c.1944G > A | Arg545Gln | 14/192 (7.3) | 15/222 (6.8) | 11/214 (5.1) |
| Exon 4 | c.412G > A | Thr34Thr | 69/201 (34.3) | 74/232 (31.9) | 52/218 (23.9) |
| Exon 4 | c.421G > A | Pro37Pro | 0/201 (0) | 1/232 (0.4) | 0/218 (0) |
| Exon 4 | c.457C > T | Thr49Thr | 2/201 (1) | 0/232 (0) | 0/218 (0) |
| Exon 16 | c.2023C > T | His571His | 0/162 (0) | 0/193 (0) | 2/196 (1.0) |
| Intron 4 | c.476 + 15C > A | | 0/201 (0) | 0/232 (0) | 1/218 (0.5) |
| Intron 6 | c.863 − 10G > A* | | N/C† | N/C | N/C |
| Intron 6 | c.863 − 5C > T* | | N/C | N/C | N/C |
| Intron 8 | c.1089 + 20G > A | | 4/133 (3.0) | 11/172 (6.4) | 4/126 (3.2) |
| Intron 9 | c.1192 + 19C > T | | 0/133 (0) | 4/172 (2.3) | 3/130 (2.3) |
| Intron 11 | c.1458 + 28G > C | | 1/133 (0.8) | 4/172 (2.3) | 0/157 (0) |
| Intron 15 | c.1922 + 10G > A | | 2/133 (1.5) | 4/172 (2.3) | 1/157 (0.6) |
| Intron 15 | c.1922 + 12G > C | | 0/133 (0) | 1/172 (0.6) | 0/157 (0) |
| Intron 15 | c.1923 − 48C > A* | | N/C | N/C | N/C |

*Sequence variation was found by direct sequencing analysis.

†Not checked

TABLE 15

Genotype distribution and allele frequency of optineurin gene polymorphisms in glaucoma patients and controls c. 412G > A (Thr34Thr)

| | | Genotype frequency (%) | | | | Genotype frequency (%) | | |
|---|---|---|---|---|---|---|---|---|
| Phenotype | n | G/G | G/A | A/A | P value* | G/G | G/A + A/A | P value* |
| POAG | 194 | 125 (64.4) | 61 (31.4) | 8 (4.1) | 0.011‡ | 125 (64.4) | 69 (35.6) | 0.009§ |
| NTG | 217 | 148 (68.2) | 62 (28.6) | 7 (3.2) | 0.078 | 148 (68.2) | 69 (31.8) | 0.064 |
| Control | 218 | 166 (76.1) | 50 (22.9) | 2 (1.0) | | 166 (76.1) | 52 (23.9) | |

| | | Genotype frequency (%) | | | Allele frequency (%) | | |
|---|---|---|---|---|---|---|---|
| Phenotype | n | G/G + G/A | A/A | P value† | G | A | P value* |
| POAG | 194 | 186 (95.9) | 8 (4.1) | 0.051 | 311 (80.2) | 77 (19.8) | 0.003§ |
| NTG | 217 | 210 (96.8) | 7 (3.2) | 0.105 | 358 (82.5) | 76 (17.5) | 0.034‡ |
| Control | 218 | 216 (99.0) | 2 (1.0) | | 382 (87.6) | 54 (12.4) | |

c.603T > A (Met98Lys)

| | | Genotype frequency (%) | | | | Genotype frequency (%) | | |
|---|---|---|---|---|---|---|---|---|
| Phenotype | n | T/T | T/A | A/A | P value* | T/T | T/A + A/A | P value* |
| POAG | 194 | 161 (83.0) | 32 (16.5) | 1 (0.5) | 0.990 | 161 (83.0) | 33 (17.0) | 0.893 |
| NTG | 217 | 169 (77.9) | 43 (19.8) | 5 (2.3) | 0.133 | 189 (77.9) | 48 (22.1) | 0.139 |
| Control | 218 | 182 (83.5) | 35 (16.0) | 1 (0.5) | | 182 (83.5) | 36 (16.5) | |

| | | Genotype frequency (%) | | | Allele frequency (%) | | |
|---|---|---|---|---|---|---|---|
| Phenotype | n | T/T + T/A | A/A | P value† | T | A | P value* |
| POAG | 194 | 193 (99.5) | 1 (0.5) | 1 | 354 (91.2) | 34 (8.8) | 0.888 |
| NTG | 217 | 212 (97.7) | 5 (2.3) | 0.122 | 391 (87.8) | 53 (12.2) | 0.071 |
| Control | 218 | 217 (99.5) | 1 (0.5) | | 399 (91.5) | 37 (8.5) | |

*P value for $\chi 2$ test.
†P value for Fisher's exact test.
‡P < 0.05
§P < 0.01

Three clinical characteristics of the glaucoma patients, viz., age at diagnosis, IOP at diagnosis, and visual field score at diagnosis, were examined for association with c.412G>A (Thr34Thr) or c.603T>A (Met98Lys) polymorphisms (Table 16). The glaucoma patients did not show an association with the clinical characteristics with the c.412G>A polymorphism. POAG patients with the G/A+A/A genotype (or 412A carriers) tended to have more advanced visual field scores than those with the G/G genotype (or non-412A carriers; P=0.093). POAG patients with the 603T>A polymorphism showed a weak association with age at diagnosis (P=0.046).

TABLE 16

Comparison of clinical characteristcs of glaucoma patients according to OPTN genotypes c.412G > A (Thr34Thr)

| | Phenotype Variable | G/G | G/A + AA | P value* |
|---|---|---|---|---|
| POAG | Age at diagnosis (ys) | 58.1 ± 11.8 (n = 123) | 58.8 ± 12.6 (n = 69) | 0.663 |
| | IOP at diagnosis (mmHg) | 27.0 ± 6.5 (n = 112) | 26.1 ± 5.0 (n = 60) | 0.360 |
| | Visual field score at diagnosis | 3.0 ± 0.9 (n = 125) | 3.2 ± 0.9 (n = 69) | 0.093 |
| NTG | Age at diagnosis (ys) | 58.7 ± 11.7 (n = 148) | 56.6 ± 11.2 (n = 69) | 0.206 |
| | IOP at diagnosis (mmHg) | 16.4 ± 2.6 (n = 139) | 16.6 ± 2.2 (n = 67) | 0.848 |
| | Visual field score at diagnosis | 2.8 ± 0.7 (n = 148) | 2.7 ± 0.7 (n = 69) | 0.135 |

c.603T > A (Met98Lys)

| | Phenotype Variable | T/T | T/A + A/A | P value* |
|---|---|---|---|---|
| POAG | Age at diagnosis (ys) | 57.6 ± 11.9 (n = 159) | 62.2 ± 12.4 (n = 33) | 0.046† |
| | IOP at diagnosis (mmHg) | 26.8 ± 5.8 (n = 143) | 26.5 ± 7.1 (n = 29) | 0.931 |
| | Visual field score at diagnosis | 3.1 ± 0.9 (n = 161) | 3.2 ± 0.9 (n = 33) | 0.280 |

TABLE 16-continued

Comparison of clinical characteristcs of glaucoma patients according to OPTN genotypes

| | | | | |
|---|---|---|---|---|
| NTG | Age at diagnosis (ys) | 58.4 ± 11.6 (n = 169) | 56.6 ± 11.6 (n = 48) | 0.304 |
| | IOP at diagnosis (mmHg) | 16.4 ± 2.4 (n = 160) | 16.8 ± 2.6 (n = 46) | 0.270 |
| | Visual field score at diagnosis | 2.8 ± 0.7 (n = 169) | 2.8 ± 0.6 (n = 48) | 0.318 |

*P values for Mann-Whitney U test.
†P < 0.05

Association between OPTN polymorphism and TNF-α Polymorphism in Glaucoma Patients No significant difference in genotype or allele frequency was noted between patients and controls for the three polymorphisms of the −308G>A, −857C>T or −863C>A. In addition, the glaucoma patients did not show an association with the clinical characteristics for the three polymorphisms (data not shown). The observed genotype frequencies were in agreement with those predicted by the Hardy-Weinberg equilibrium.

However, among individuals with the C/T+T/T genotype (or −857T carriers) in the TNF-α gene, 44.1% of POAG patients were G/A+A/A genotypes (or 412A carriers) in the OPTN gene compared to 21.6% of controls (Table 17). This difference in frequency was significant (P=0.006). Among individuals with the C/A+A/A genotype (or −863A carriers) in the TNF-α gene, 603A carriers (or Lys98 carriers) in the OPTN gene were significantly associated with POAG as well as NTG (P=0.008 and 0.027, respectively).

TABLE 17

Distribution of optineurin genotypes (c.412G > A and c.603T > A) according to TNF-α genotypes (−857C > T and −863C > A)

| c.412G > A (Thr34Thr) | | | | | | | | | |
|---|---|---|---|---|---|---|---|---|---|
| | −857C > T | C/C (%) | | | Odds ratio | C/T + T/T (%) | | | Odds ratio |
| Phenotype | c.412G > A | G/G | G/A + A/A | P value* | 95% CI | G/G | G/A + A/A | P value* | 95% CI |
| POAG | | 92 (68.1) | 43 (31.9) | 0.204 | 1.40 (0.83-2.37) | 33 (55.9) | 26 (44.1) | 0.006‡ | 2.86 (1.34-6.08) |
| NTG | | 97 (65.5) | 51 (34.5) | 0.077 | 1.58 (0.95-2.62) | 51 (73.9) | 18 (26.1) | 0.531 | 1.28 (0.59-2.77) |
| Control | | 108 (75.0) | 36 (25.0) | | | 58 (78.4) | 16 (21.6) | | |
| | −863C > A | C/C (%) | | | Odds ratio | C/A + A/A(%) | | | Odds ratio |
| Phenotype | c.412G > A | G/G | G/A + A/A | P value* | 95% CI | G/G | G/A + A/A | P value* | 95% CI |
| POAG | | 91 (64.5) | 50 (35.5) | 0.017 | 1.84 (1.11-3.05) | 34 (64.2) | 19 (35.8) | 0.280 | 1.56 (0.69-3.53) |
| NTG | | 110 (69.2) | 49 (30.8) | 0.114 | 1.49 (0.91-2.46) | 38 (65.5) | 20 (34.5) | 0.341 | 1.47 (0.66-3.28) |
| Control | | 124 (77.0) | 37 (23.0) | | | 42 (73.7) | 15 (26.3) | | |
| c.603T > A (Met98Lys) | | | | | | | | | |
| | −857C > T | C/C (%) | | | Odds ratio | C/T + T/T (%) | | | Odds ratio |
| Phenotype | c.603T > A | T/T | T/A + A/A | P value* | 95% CI | T/T | T/A + A/A | P value* | 95% CI |
| POAG | | 112 (83.0) | 23 (17.0) | 0.811 | 1.08 (0.57-2.03) | 49 (83.1) | 10 (16.9) | 0.925 | 0.96 (0.39-2.37) |
| NTG | | 111 (75.0) | 37 (25.0) | 0.056 | 1.75 (0.98-3.13) | 58 (84.1) | 11 (15.9) | 0.795 | 0.89 (0.37-2.14) |
| Control | | 121 (84.0) | 23 (16.0) | | | 61 (82.4) | 13 (17.6) | | |
| | −863C > A | C/C (%) | | | Odds ratio | C/A + A/A (%) | | | Odds ratio |
| Phenotype | c.603T > A | T/T | T/A + A/A | P value* | 95% CI | T/T | T/A + A/A | P value* | 95% CI |
| POAG | | 123 (87.2) | 18 (12.8) | 0.127 | 0.61 (0.33-1.15) | 38 (71.7) | 15 (28.3) | 0.008‡ | 4.11 (1.37-12.27) |
| NTG | | 125 (78.6) | 34 (21.4) | 0.636 | 1.14 (0.66-1.97) | 44 (75.9) | 14 (24.1) | 0.027† | 3.31 (1.10-9.91) |
| Control | | 130 (80.7) | 31 (19.3) | | | 52 (91.2) | 5 (8.8) | | |

*P values for $\chi 2$ test.
†P < 0.05
‡P < 0.01

The clinical characteristics of these combined genotypes, such as age at diagnosis, IOP at diagnosis, and visual field score at diagnosis are shown in Table 18. The POAG patients who were TNF-α/−857T and optineurin/412A carriers had significantly worse (P=0.020) visual field scores than those who were TNF-α/−857T and non-optineurin/412A carriers. However, there was no significant difference in the three clinical features of POAG patients among the four genotypes of combined −857T>A and c.412G>A polymorphisms (Table 6) by one-way ANOVA: P=0.823 for age at diagnosis; P=0.692 for IOP at diagnosis; and P=0.152 for visual field score at diagnosis.

POAG patients who were TNF-α/−863A and optineurin/603A carriers had significantly worse (P=0.026) visual field scores than those who were TNF-α/−863A and non-optineurin/603A carriers. However, there was no significant difference in the visual field score of POAG patients among the four genotypes of combined −863C>A and −603T>A polymorphisms (Table 6, one-way ANOVA: P=0.200).

TABLE 18

Comparison of clinical characteristics of glaucoma patients according to TNF-α genotypes (−857T and −863A) and optineurin genotypes (412A and 603A)

c.412G > A (Thr34Thr)

| | (TNF-α genotypes) | C/T + T/T (−857T carrier) | | |
|---|---|---|---|---|
| | (OPTN genotypes) | G/G | G/A + A/A | P value* |
| POAG | Age at diagnosis (ys) | 57.1 ± 10.7 (n = 32) | 57.6 ± 13.1 (n = 26) | 0.802 |
| | IOP at diagnosis (mmHg) | 26.4 ± 6.1 (n = 30) | 26.4 ± 5.5 (n = 20) | 0.786 |
| | Visual field score | 2.9 ± 0.9 (n = 33) | 3.3 ± 0.8 (n = 26) | 0.020† |
| NTG | Age at diagnosis (ys) | 58.4 ± 11.1 (n = 51) | 59.3 ± 10.5 (n = 18) | 0.790 |
| | IOP at diagnosis (mmHg) | 16.4 ± 2.6 (n = 46) | 16.1 ± 2.3 (n = 17) | 0.520 |
| | Visual field score | 2.8 ± 0.8 (n = 51) | 2.6 ± 0.5 (n = 18) | 0.335 |

c.603T > A (Met98Lys)

| | (TNF-α genotypes) | C/A + A/A (−863A carrier) | | |
|---|---|---|---|---|
| | (OPTN genotypes) | T/T | T/A + A/A | P value* |
| POAG | Age at diagnosis (ys) | 56.3 ± 10.5 (n = 38) | 62.0 ± 13.8 (n = 15) | 0.074 |
| | IOP at diagnosis (mmHg) | 27.9 ± 6.5 (n = 36) | 26.9 ± 8.7 (n = 14) | 0.488 |
| | Visual field score | 3.0 ± 0.8 (n = 38) | 3.5 ± 0.9 (n = 15) | 0.026† |
| NTG | Age at diagnosis (ys) | 57.9 ± 11.4 (n = 44) | 56.9 ± 11.9 (n = 14) | 0.579 |
| | IOP at diagnosis (mmHg) | 16.2 ± 2.4 (n = 40) | 16.9 ± 2.4 (n = 14) | 0.364 |
| | Visual field score | 2.9 ± 0.5 (n = 44) | 2.7 ± 0.6 (n = 14) | 0.296 |

*P values for Mann-Whitney U test.
†P < 0.05

Partial nucleotide sequence of OPTN exon 4, comprising the targeted polymorphism, 412G>A (underlined)

```
caacagtgac ttttccacag gaacttctgc aatgtcccat caacctctca gctgcctcac  (SEQ ID NO: 112)
tgaaaaggag gacagcccca gtgaaagcac aggaaatgga cccccccacc tggcccaccc
aaacctggac acttttaccc cggaggagct gctgcagcag atgaaagagc tcctgaccga
gaaccaccag ctgaaaggtg agcagggctg gcccctgtgt gccccattca tcctgggcct
```

Sequence of OPTN gene, GeneBank Accession No. AF423071

```
  1 atcccggtcg ggagttctct ccaggcggca cgatgccgag gaaacagtga ccctgagcga  (SEQ ID NO: 113)
 61 agccaagccg ggcggcaggt gtggctttga tagctggtgg tgccacttcc tggccttgga
121 tgagccgtac gcctctgtaa acccaacttc ctcacctttg aaacagctgc ctggttcagc
181 attaatgaag attagtcagt gacaggcctg gtgtgctgag tccgcacata gaagaatcaa
241 aaatgtccaa aatgtaactg gagagaaagt gggcaacttt tggagtgact tttccacagg
301 aacttctgca atgtcccatc aacctctcag ctgcctcact gaaaaggagg acagccccag
361 tgaaagcaca ggaaatggac ccccccacct ggcccaccca aacctggaca cgtttacccc
421 ggaggagctg ctgcagcaga tgaaagagct cctgaccgag aaccaccagc tgaaagaagc
```

-continued

```
 481 catgaagcta aataatcaag ccatgaaagg gagatttgag gagctttcgg cctggacaga
 541 gaaacagaag gaagaacgcc agtttttga gatacagagc aaagaagcaa aagagcgtct
 601 aatggccttg agtcatgaga atgagaaatt gaaggaagag cttggaaaac taaaagggaa
 661 atcagaaagg tcatctgagg accccactga tgactccagg cttcccaggg ccgaagcgga
 721 gcaggaaaag gaccagctca ggacccaggt ggtgaggcta caagcagaga aggcagacct
 781 gttgggcatc gtgtctgaac tgcagctcaa gctgaactcc agcggctcct cagaagattc
 841 ctttgttgaa attaggatgg ctgaaggaga agcagaaggg tcagtaaaag aaatcaagca
 901 tagtcctggg cccacgagaa cagtctccaa tggcacggca ttgtctaaat ataggagcag
 961 atctgcagat ggggccaaga attacttcga acatgaggag ttaactgtga gccagctcct
1021 gctgtgccta agggaaggga atcagaaggt ggagagactt gaagttgcac tcaaggaggc
1081 caaagaaaga gtttcagatt ttgaaaagaa aacaagtaat cgttctgaga ttgaaaccca
1141 gacagagggg agcacagaga aagagaatga tgaagagaaa ggcccggaga ctgttggaag
1201 cgaagtggaa gcactgaacc tccaggtgac atctctgttt aaggagcttc aagaggctca
1261 tacaaaactc agcgaagctg agctaatgaa gaagagactt caagaaaagt gtcaggccct
1321 tgaaaggaaa aattctgcaa ttccatcaga gttgaatgaa aagcaagagc ttgtttatac
1381 taacaaaaag ttagagctac aagtggaaag catgctatca gaaatcaaaa tggaacaggc
1441 taaaacagag gatgaaaagt ccaaattaac tgtgctacag atgacacaca acaagcttct
1501 tcaagaacat aataatgcat tgaaaacaat tgaggaacta acaagaaaag agtcagaaaa
1561 agtggacagg gcagtgctga aggaactgag tgaaaaactg gaactggcag agaaggctct
1621 ggcttccaaa cagctgcaaa tggatgaaat gaagcaaacc attgcctagc aggaagagga
1681 cctggaaacc atgaccatcc tcagggctca gatggaagtt tactgttctg attttcatgc
1741 tgaaagagca gcgagagaga aaattcatga ggaaaaggag caactgtcat tgcagctggc
1801 agttctgctg aaagagaatg atgctttcga agacggaggc aggcagtcct tgatggagat
1861 gcagagtcgt catggggcga gaacaagtga ctctgaccag caggcttacc ttgttcaaag
1921 aggagctgag gacagggact ggcggcaaca gcggaatatt ccgatttatt cctgccccaa
1981 gtgtggagag gttctgcctg acatagacac gttacagatt cacgtgttgg attgcatcat
2041 ttaagtgttg atgtatcacc tccccaaaac tgttggt
```

Partial nucleotide sequence for TNF-α gene comprising the targeted polymorphic position is as follows:

```
TNF-α -863C > A; -857C > T (underlined)
3121 ccacatgtag cggctctgag gaatgggtta caggagacct ctggggtgat gtgaccacag  (SEQ ID NO: 114)

3181 caatgggtag gagaatgtcc agggctatga aagtcgagta tggggacccc cccttaacga

                                                     -863C > A -857C > T

3241 agacagggcc atgtagaggg ccccagggag tgaaagagcc tccaggtcct ccaggtatgg

3301 aatacagggg acgtttaaga agatatggcc acacactggg gccctgtgaa gtgagagctt
```

EXAMPLE 7

Effect of Oral Angiotensin II Receptor Blocker on IOP in Normal Subjects and its Association with SNPs in AT1R and AT2R Genes

EXAMPLE 7-1

Methods

Relationship between polymorphism at nucleotide number 3123 (C or A) of the angiotensin II receptor 2 gene (AT2R) on chromosome-X and the effect of candesartan cilexetil, an angiotensin II receptor blocker was examined. This study was performed on 20 healthy volunteers (13 men and 8 women) without systemic and eye diseases. Among them, 9 men had C, 4 men had A, 4 women had CC and 4 women had CA genotype at the polymorphic point. The each subject was given candesartan cilexetil orally and the IOP was recorded from 1 to 24 hours after the administration.

Results

Change in Intraocular pressure 1-24 hours after the drug administration is shown in Table 19.

TABLE 19

| time 0 | Lowering IOP mmHg | | | | | | | AT2R 3123C > A | | | | |
|---|---|---|---|---|---|---|---|---|---|---|---|---|
| Base Line | 1 Hr | 2 Hr | 3 Hr | 4 Hr | 5 Hr | 6 Hr | 24 Hr | M | M | F | F | |
| 0 | −2 | −1 | −3 | −2 | −1 | −1 | −1 | | A | | | I |
| 0 | −2 | −2 | 0 | 0 | −1 | 1 | 1 | | A | | | |
| 0 | 1 | 1 | 0 | 0 | −2 | −2 | 0 | | A | | | |
| 0 | 0 | 0 | −2 | 1 | 0 | 0 | −1 | C | | | | |
| 0 | −1 | −3 | −5 | −2 | −3 | −3 | −3 | C | | | | II |
| 0 | 0 | −3 | −2 | −4 | −3 | 0 | 0 | | | | CA | |
| 0 | −1 | −1 | −4 | −3 | −4 | −3 | 1 | C | | | | |
| 0 | −2 | −4 | −4 | −4 | −4 | −5 | −2 | C | | | | |
| 0 | −2 | −3 | −3 | −2 | −2 | 1 | 2 | | | CC | | |
| 0 | −2 | −3 | −2 | −5 | −3 | −3 | 0 | C | | | | |
| 0 | −4 | −6 | −6 | −6 | −6 | −4 | −5 | | | | CA | III |
| 0 | −4 | −5 | −6 | −5 | −5 | −5 | −7 | C | | | | |
| 0 | −4 | −6 | −6 | −8 | −5 | −5 | −4 | | | | CA | |
| 0 | −2 | −3 | −6 | −5 | −6 | −3 | −3 | C | | | | |
| 0 | −2 | −4 | −4 | −6 | −3 | −4 | −5 | | | | CA | |
| 0 | −4 | −8 | −6 | −7 | −6 | −6 | −2 | | | CC | | |
| 0 | −4 | −4 | −5 | −3 | −5 | −4 | −3 | C | | | | |
| 0 | −1 | −4 | −6 | −3 | −6 | −4 | 0 | | | CC | | |
| 0 | −2 | −4 | −7 | −5 | −7 | −6 | −3 | | | CC | | |
| 0 | −2 | −7 | −6 | −4 | −6 | −6 | −1 | C | | | | |
| 0 | −6 | −8 | −8 | −12 | −12 | −12 | −12 | | A | | | |

| | IOP Lowering Effect | genotype |
|---|---|---|
| Group I | − | 3 of 4 had A |
| Group II | + | 5 of 6 had C or CC |
| Group III | ++ | 7 of 11 had C or CC |

In male, oral administration of candesartan cilexetil hardly lowered the IOP of 75% of those with A genotype at nucleotide 3123 of AT2R gene, whereas the IOP of 100% of those with C genotype was effectively lowered. In female, oral administration of candesartan cilexetil was effectively lower the IOP of 100% of those with CC genotype.

This result suggest that nucleotide 3123 of AT2(AGTR2) gene polymorphism associate with the effect of candesartan cilexetil.

EXAMPLE 7-2

Methods

This study was performed on 20 healthy volunteers (13 men and 7 woman, age 23 to 28 years) without systemic and eye diseases. In the morning (10:00 hr), each subject was given either 12 mg oral candesartan cilexetil (Blopress®, Takeda, Japan) or the placebo in a randomized crossover double-blind fashion.

The baseline heart rate, systolic/diastolic arterial pressures (SBP/DBP), and IOP were recorded. The subjects then received oral candesartan cilexetil or placebo, and measurements were repeated hourly for 6 hr and after 24 hr. One month later, each subject received the alternative treatment. Only the right eye was measured and analyzed.

The ocular perfusion pressure (OPP) is defined as the difference between the pressure in the arteries entering the tissue and the veins leaving it. The OPP can be approximated by the following formula using the mean blood pressure (BPm) and the IOP.

$$OPP = \frac{2}{3} \times BPm - IOP, \text{ where } BPm = DBP + \frac{1}{3} \times (SBP - DBP).$$

A search for polymorphisms in ATR1 and ATR2 was performed in the 20 subjects and correlated with the changes in the IOP. This research followed the tenets of the Declaration of Helsinki. Written informed consent was obtained after the nature and possible consequences of the study were explained. Where applicable, the research was approved by the institutional human experimentation committee for analysis of DNA.

Statistical Analysis

Statistical analysis of the results following ARB was performed with StatView (SAS Institute, USA) using repeated measure ANOVA test. ANOVA test with Bonferroni correction was used for statistical analysis of each IOP values: a P value <0.0004 was considered to be statistically significant.

Results

Figure 5:
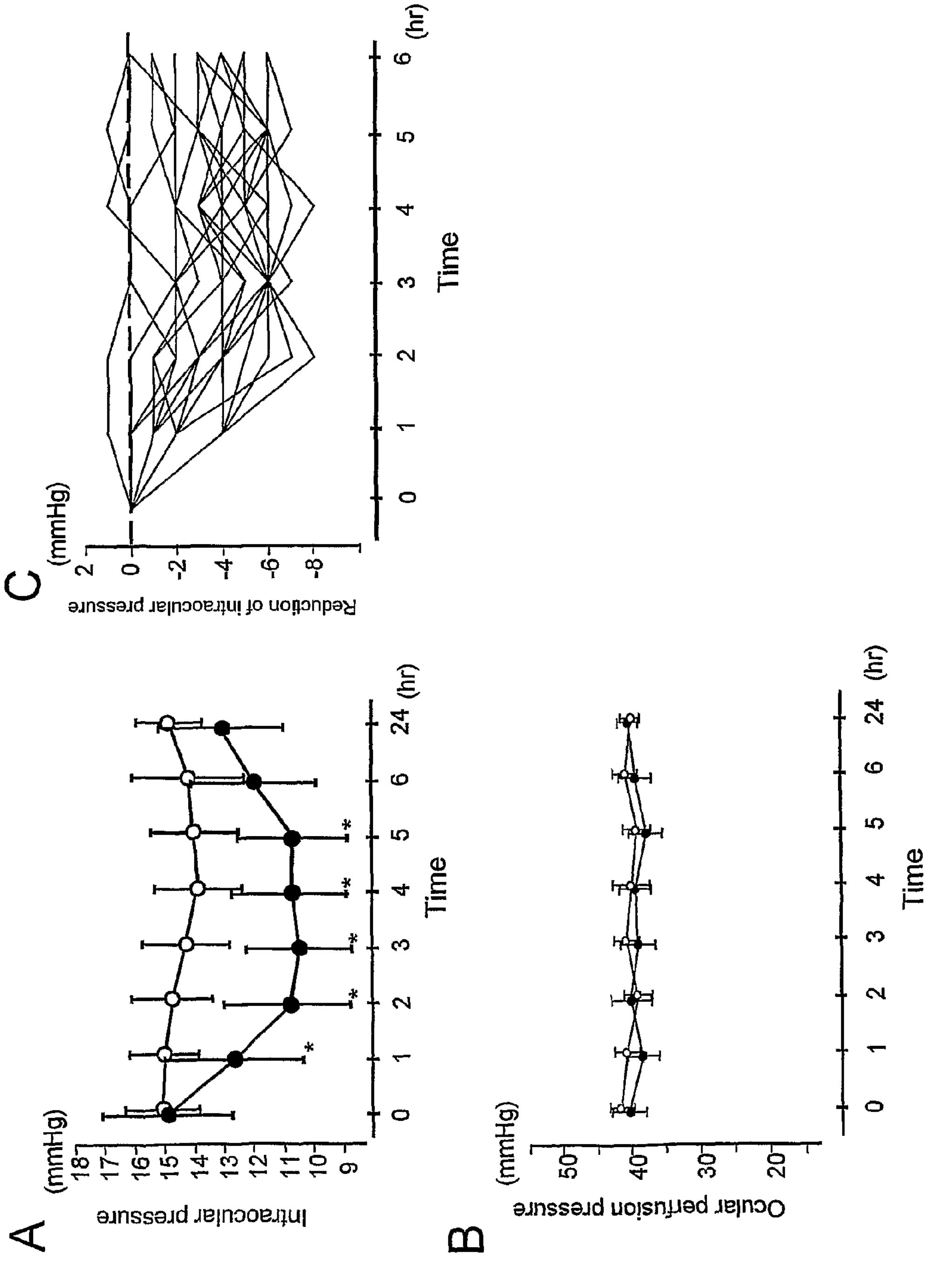
FIG. 5A represents the IOP after oral candesartan cilexetil or placebo.
FIG. 5B represents the ocular perfusion pressure after oral candesartan cilexetil or placebo
FIG. 5C represents the IOP after oral candesartan cilexetil in each of the 15 subjects.

The changes in the IOP after oral candesartan cilexetil or placebo are shown in FIG. 5A. The IOP in the subjects who received the placebo was not altered significantly. On the other hand, as early as 1 hr after oral candesartan cilexetil, the IOP had fallen significantly and remained low for 5 hr (P<0.0001) compared with placebo. Candesartan cilexetil did not significantly affect perfusion pressures (FIG. 5B). No significant change in SBP, DBP, and heart rate was detected after a single oral dose of candesartan cilexetil or placebo (data not shown).

The changes in the IOP after oral candesartan cilexetil in each of the 20 subjects are shown in FIG. 5C. There was no significant association between the effects of candesartan cilexetil and the three SNPs in the ATR1 gene in the 20 control subjects (Table 19-2). For the ATR2 genotype, however, 4 men with the A genotype showed a reduction of the IOP by 2.3±0.5 mmHg, which was the same value as that of subjects who received placebo, and a significantly less decrease in the IOP than in the 9 men with the C genotype (5.0±1.1 mmHg, P=0.014). No woman had the AA genotype in this study.

TABLE 19-2

Effects of angiotensin II receptor blocker on intraocular pressure in association with genotypes of the angiotensin II receptor genes

| Polymorphisms | Genotype | Number (eyes) | Maximum reduction of IOP (mmHg) | P* |
|---|---|---|---|---|
| AGTR1 −713T > G | TT | 18 | 4.9 ± 1.8 | P = 0.898 |
| | TG | 2 | 5.0 ± 4.2 | |
| | GG | 0 | 0 | |
| AGTR1 −521C > T | CC | 18 | 4.9 ± 1.8 | P† = 0.117 |
| | CT | 1 | 2 | |
| | TT | 1 | 8 | |
| AGTR1 1166A > C | AA | 18 | 5.1 ± 2.0 | P = 0.405 |
| | AC | 2 | 5.2 ± 1.6 | |
| | CC | 0 | 0 | |
| AGTR2 3123C > A | C (male) | 9 | 5.0 ± 1.1 | P = 0.014‡ |
| | A (male) | 4 | 2.3 ± 0.5 | |
| | CC (female) | 3 | 7.0 ± 1.0 | P = 0.354 |
| | CA (female) | 4 | 6.0 ± 1.6 | |
| | AA (female) | 0 | 0 | |

*P value for Mann-Whitney U test
†P value for Kruskal-Wallis test
‡P < 0.05

EXAMPLE 8

Associations Between Glaucoma and Gene Polymorphisms of Endothelin-1 and Endothelin type A Receptor Purpose: Endothelin 1 (ET-1), a potent vasoconstrictor, may affect regulation of intraocular pressure and ocular vessel tone. Thus, ET-1 and its receptors may contribute to development of glaucoma. We investigated whether gene polymorphisms of ET-1 (EDN1) and its receptors $ET_A$ (EDNRA) and $ET_B$ (EDNRB) were associated with glaucoma phenotypes and clinical features.

Methods

Study Population:

A total of 650 Japanese subjects (224 normal controls, 176 POAG patients, and 250 NTG patients), recruited from seven Japanese medical institutions, were examined in this study. All subjects were unrelated. Mean age (±standard deviation) at diagnosis of OAG was 57.2±12.8 years. OAG subjects were divided into POAG patients and NTG patients, aged 58.8±12.2 and 56.1±13.2 years at diagnosis, respectively (Table 1). Mean age at the time of examination was 70.0±11.2 years in controls. We purposely selected older control subjects to reduce the likelihood that a subset of controls would later develop glaucoma.

Ophthalmic examinations included slit-lamp biomicroscopy, optic disc examination, IOP measurement by Goldmann applanation tonometry, and gonioscopy. Visual fields were assessed with Humphrey automated perimetry (program 30-2) or Goldmann perimetry. Severity of visual field defects was scored from 1 to 5. Data obtained by two types of perimetry were combined using a five-point scale: 1, no alterations; 2, early defects; 3, moderate defects; 4, severe defects; and 5, light perception only or no light perception. This severity scale followed Kozaki's classification, which has been used most widely in Japan so far, based on Goldmann perimetry, or by the classification established for the Humphrey Field Analyzer.

POAG was diagnosed on fulfillment of all of the following criteria: maximum IOP was above 21 mm Hg; open angles on gonioscopy; typical glaucomatous disc cupping associated with visual field changes; and absence of other ocular, rhinologic, neurological, or systemic disorders potentially causing optic nerve damage. We excluded patients with elevated IOP secondary to defined causes (e.g., trauma, uveitis, steroid administration, or exfoliative, pigmentary, or neovascular glaucoma). POAG patients with MYOC mutations and JOAG patients were also excluded. NTG was diagnosed by the same criteria as POAG except that IOP did not exceed 21 mm Hg at all times during the follow-up period. Normal control subjects had IOP less than 20 mm Hg, no glaucomatous disc changes, and no family history of glaucoma.

DNA Extraction and Genotyping of the Polymorphisms

Genomic DNA was isolated from peripheral blood lymphocytes by standard methods. Nine single nucleotide polymorphisms (SNPs) were detected among all participants: four for EDN1 (T-1370G, +138/ex1 del/ins, G8002A, K198N); four for EDNRA (G-231A, H323H, C+70G, C+1222T); and one for EDNRB (L277L). These polymorphisms are listed at http://genecanvas.idf.inserm.fr/. We genotyped these SNPs using the Invader® assay (Third Wave Technologies, Inc, Madison, Wis.), which was recently developed for high-throughput genotyping of SNPs (Lyamichev V et. al., Nat Biotechnol 1999; 17:292-296, the contents of the cited reference are herein incorporated by reference).

The oligonucleotide sequences of primary probes and Invader® probes used in this study are listed in Table 20.

TABLE 20

Sequences of primary probes and Invader oligonucleotides used in assays

| Polymorphism | Location | Nucleotide change | Target | Probe | Sequence (The lower case letters indicate the flap sequences) | |
|---|---|---|---|---|---|---|
| EDN1/T - 1370G | 5'- flanking region | T/G | Anit- sense | T probe | Flap sequence-TTGGTGGAGAACAAACAA | (SEQ ID NO: 115) |
| | | | | G probe | Flap sequence-GTGGTGGAGAACAAACA | (SEQ ID NO: 116) |
| | | | | Invader | GGTCTTACTGGGCCACTGTGAGCGCTC | (SEQ ID NO: 117) |

TABLE 20-continued

Sequences of primary probes and Invader oligonucleotides used in assays

| Poly-morphism | Location | Nucle-otide change | Target | Probe | Sequence (The lower case letters indicate the flap sequences) | |
|---|---|---|---|---|---|---|
| EDN1/+138/ex1 del/ins | Exon 1 | del/ins | Sense | A del probe | Flap sequence-TAACGGGGAGAAAAGG | (SEQ ID NO: 118) |
| | | | | A ins probe | Flap sequence-TTAACGGGGAGAAAAGG | (SEQ ID NO: 119) |
| | | | | Invader | GCGATCCTTCAGCCCAAGTGCCCTTC | (SEQ ID NO: 120) |
| EDN1/G8002A | Intron 4 | G/A | Anti-sense | G probe | Flap sequence-GAAAATCATTTTGGGGAGC | (SEQ ID NO: 121) |
| | | | | A probe | Flap sequence-AAAAATCATTTTGGGGAGC | (SEQ ID NO: 122) |
| | | | | Invader | TGCCTCTCTGAGTCAATGTATTTACCACTTTCCCTGAGAAATCT | (SEQ ID NO: 123) |
| EDN1K198N | Exon 5 | G/T | Sense | G probe | Flap sequence-CTTGCCTTTCAGCTTGG | (SEQ ID NO: 124) |
| | | | | T probe | Flap sequence-ATTGCCTTTCAGCTTGG | (SEQ ID NO: 125) |
| | | | | Invader | GTTGTGGGTCACATAACGCTCTCTGGAGGGT | (SEQ ID NO: 126) |
| ENDRA/G - 231 A | Exon 1 | G/A | Sense | G probe | Flap sequence-CTCCTGGGGCACTGC | (SEQ ID NO: 127) |
| | | | | A probe | Flap sequence-TTCCTGGGCACTGC | (SEQ ID NO: 128) |
| | | | | Invader | CTGCACAGCTTCCCCGGCTTCAGAAAACA | (SEQ ID NO: 129) |
| EDNRA/H323H | Exon 6 | T/C | Anti-sense | T probe | Flap sequence-TTTAAGCCGTATATTGAAGAAAA | (SEQ ID NO: 130) |
| | | | | C probe | Flap sequence-CTTAAGCCGTATATTGAAGAAAA | (SEQ ID NO: 131) |
| | | | | Invader | CTTGGTTGTAATTTTTGCTCTTTGCTGGTTCCCTCTTCAA | (SEQ ID NO: 132) |
| EDNRA/C + 70G | Exon 8 | C/G | Sense | C probe | Flap sequence-GTCACAGTTGCCTTGT | (SEQ ID NO: 133) |
| | | | | G probe | Flap sequence-CTCACAGTTGCCTTGT | (SEQ ID NO: 134) |
| | | | | Invader | GGAAGAAGGATCAGAGAAGAGATTCCCGGAT | (SEQ ID NO: 135) |
| EDNRA/C + 1222T | Exon 8 | C/T | Anti-sense | C probe | Flap sequence-CTTGGGGTTTTCAGTATGA | (SEQ ID NO: 136) |
| | | | | T probe | Flap sequence-TTTGGGGTTTTCAGTATGA | (SEQ ID NO: 137) |
| | | | | Invader | CCCACAAATGCCACCAGAACTTAACGATTCTTCACTTA | (SEQ ID NO: 138) |
| EDNRB/L277L | Exon 4 | A/G | Anti-sense | A probe | Flap sequence-ATTCAGTTTCTATTTCTGCTTG | (SEQ ID NO: 139) |
| | | | | G probe | Flap sequence-GTTCAGTTTCTATTTCTGCTTG | (SEQ ID NO: 140) |
| | | | | Invader | CTCATCCCTATAGTTTTACAAGACAGCAAAAGATTGGTGGCTT | (SEQ ID NO: 141) |

Nine polymorphisms were detected among all participants. These polymorphisms are listed at http://genecanvas.icif.inserm.fr/. Genotyping of the polymorphisms were performed by the Invader ® assay using the pobes listed above.

Statistical Analysis

Comparisons of genotype distributions in normal controls with those in OAG patients, POAG patients, and NTG patients were performed by $\chi^2$ analysis. Associations of clinical characteristics (age at diagnosis, untreated maximum of IOP, and visual field score at diagnosis) with genotypes were assessed by the Mann-Whitney U test. Statistical analyses were carried out with SPSS for Windows (version 12.0; SPSS Inc, Chicago, Ill.). A value of $p<0.05$ was considered to be significant.

Results

Table 21 shows genotype and allele frequencies obtained in this study. Distributions were consistent with Hardy-Weinberg equilibrium. For the EDN1/+138/ex1 del/ins polymorphism, frequencies of the del/del and del/ins+ins/ins genotypes respectively were 74.2% and 25.8% in OAG patients overall (p=0.016), 74.4% and 25.6% in POAG patients (p=0.047), and 74.0% and 26.0% in NTG patients (p=0.037), compared with 65.2% and 34.8% in control subjects. For the EDN1/K198N polymorphism, 53.2% of OAG patients were found to have the KK genotype, which was significantly higher than the 43.8% prevalence in control subjects (p=0.022). When OAG patients were divided into those with POAG and those with NTG, frequency of the KK genotype in NTG patients was much higher than in controls (p=0.008), while genotype and allele frequency distributions in POAG patients did not differ statistically from those in controls. A gender difference was noted; specifically, the KK genotype was significantly more prevalent in female NTG patients (p=0.010 vs. female controls) than in male NTG patients (p=0.251 vs. male controls; Table 22). Polymorphism of EDN1/G8002A in the intron 4 region was highly coincident with EDN1/K198N, except in one sample (data not shown).

Frequencies of EDNRA/C+1222T genotypes (CC vs. CT+TT) differed slightly between OAG patients and controls (p=0.036). Distribution of genotypes for other polymorphisms showed no significant differences between any patient group and controls.

Characteristics of patients are examined in dominant model and recessive model of each polymorphism, and data with significant differences are shown in Table 23. In OAG patients overall and in POAG patients, no characteristic showed a significant difference between genotype groups. In NTG patients, however, the AA group of EDNRA/G-231A had poorer visual field scores at diagnosis than the GG+GA group (3.0±0.8 vs. 2.7±0.6, p=0.043). We also found significantly poorer visual field scores at diagnosis in the GG group for EDNRA/C+70G than the CC+CG group among NTG patients (3.0±0.7 vs. 2.7±0.7, p=0.014). Untreated maximum of IOP in the TT group for EDNRA/H323H was statistically higher than in the CC+CT group in NTG patients (17.2±2.2 vs. 16.6±2.3, p=0.040). Other polymorphisms in NTG patients showed no significant differences in characteristics between genotype groups.

TABLE 21

Genotype and allele frequencies of EDN1, EDNRA, and EDNRB polymorphisms in control subjects and glaucoma patients

| Polymorphism | | Genotype frequency | | p value | Allele frequency | | p value |
|---|---|---|---|---|---|---|---|
| | | TT | TG + GG | | T | G | |
| EDN1/T − 1370G | Control (n = 224) | 133 (59.4) | 91 (40.6) | | 350 (78.1) | 98 (21.9) | |
| | OAG (n = 426) | 273 (64.1) | 153 (35.9) | 0.239 | 675 (79.2) | 177 (20.8) | 0.644 |
| | POAG (n = 176) | 108 (61.4) | 68 (38.6) | 0.687 | 275 (78.1) | 77 (21.9) | 1.000 |
| | NTG (n = 250) | 165 (66.0) | 85 (34.0) | 0.136 | 400 (80.0) | 100 (20.0) | 0.478 |
| | | del del | del ins + ins ins | | del | ins | |
| EDN1/+138/ex1 del/ins | Control (n = 224) | 146 (65.2) | 78 (34.8) | | 364 (81.3) | 84 (18.8) | |
| | OAG (n = 426) | 316 (74.2) | 110 (25.8) | 0.016* | 734 (86.2) | 118 (13.8) | 0.020* |
| | POAG (n = 176) | 131 (74.4) | 45 (25.6) | 0.047* | 303 (86.1) | 49 (13.9) | 0.069 |
| | NTG (n = 250) | 185 (74.0) | 65 (26.0) | 0.037* | 431 (86.2) | 69 (13.8) | 0.039* |
| | | KK | KN + NN | | K | N | |
| EDN1/K198N | Control (n = 224) | 98 (43.8) | 126 (56.3) | | 295 (65.8) | 153 (34.2) | |
| | OAG (n = 425) | 226 (53.2) | 199 (46.8) | 0.022* | 609 (71.6) | 241 (28.4) | 0.031* |
| | POAG (n = 175) | 86 (49.1) | 89 (50.9) | 0.284 | 245 (70.0) | 105 (30.0) | 0.213 |
| | NTG (n = 250) | 140 (56.0) | 110 (44.0) | 0.008* | 364 (72.8) | 136 (27.2) | 0.020* |
| | | GG | GA + AA | | G | A | |
| EDNRA/G − 231A | Control (n = 224) | 62 (27.7) | 162 (72.3) | | 244 (54.5) | 204 (45.5) | |
| | OAG (n = 425) | 118 (27.8) | 307 (72.2) | 0.981 | 455 (53.5) | 395 (46.5) | 0.748 |
| | POAG (n = 176) | 52 (29.5) | 124 (70.5) | 0.681 | 195 (55.4) | 157 (44.6) | 0.792 |
| | NTG (n = 249) | 66 (26.5) | 183 (73.5) | 0.774 | 260 (52.2) | 238 (47.8) | 0.488 |
| | | TT | TC + CC | | T | C | |
| EDNRA/H323H | Control (n = 224) | 122 (54.5) | 102 (45.5) | | 327 (73.0) | 121 (27.0) | |
| | OAG (n = 426) | 228 (53.5) | 198 (46.5) | 0.819 | 626 (73.5) | 226 (26.5) | 0.852 |
| | POAG (n = 176) | 95 (54.0) | 81 (46.0) | 0.923 | 259 (73.6) | 93 (26.4) | 0.852 |
| | NTG (n = 250) | 133 (53.2) | 117 (46.8) | 0.783 | 367 (73.4) | 133 (26.6) | 0.887 |
| | | CC | CG + GG | | C | G | |
| EDNRA/C + 70G | Control (n = 224) | 61 (27.2) | 163 (72.8) | | 229 (51.1) | 219 (48.9) | |
| | OAG (n = 426) | 128 (30.0) | 298 (70.0) | 0.453 | 462 (54.2) | 390 (45.8) | 0.286 |
| | POAG (n = 176) | 57 (32.4) | 119 (67.6) | 0.262 | 196 (55.7) | 156 (44.3) | 0.199 |
| | NTG (n = 250) | 71 (28.4) | 179 (71.6) | 0.777 | 266 (53.2) | 234 (46.8) | 0.521 |
| | | CC | CT + TT | | C | T | |
| EDNRA/C + 1222T | Control (n = 224) | 137 (61.2) | 87 (38.8) | | 347 (77.5) | 101 (22.5) | |
| | OAG (n = 426) | 224 (52.6) | 202 (47.4) | 0.036* | 620 (72.8) | 232 (27.2) | 0.066 |
| | POAG (n = 176) | 92 (52.3) | 84 (47.4) | 0.074 | 254 (72.2) | 98 (27.8) | 0.085 |
| | NTG (n = 250) | 132 (52.8) | 118 (47.2) | 0.067 | 366 (73.2) | 134 (26.8) | 0.130 |
| | | AA | AG + GG | | A | G | |
| EDNRB/L277L | Control (n = 224) | 77 (34.4) | 147 (65.6) | | 254 (56.7) | 194 (43.3) | |
| | OAG (n = 425) | 118 (27.8) | 307 (72.2) | 0.081 | 443 (52.1) | 407 (47.9) | 0.116 |
| | POAG (n = 176) | 48 (27.3) | 128 (72.7) | 0.128 | 184 (52.3) | 168 (47.7) | 0.212 |
| | NTG (n = 249) | 70 (28.1) | 179 (71.9) | 0.142 | 259 (52.0) | 239 (48.0) | 0.148 |

Data are n (%).

*$P < 0.05$ ($\chi^2$ test).

Genotype distributions showed significant differences for EDN1/+138/ex1 del/ins (p = 0.016) and EDN1/K198N (p = 0.022) polymorphisms, and a slight difference for EDNRA/C + 1222T polymorphism (p = 0.036) between OAG patients and controls. After dividing the OAG group into POAG and NTG, frequency of the KK genotype for the EDN1/K198N polymorphism in NTG patients was much higher than in controls (p = 0.008).

TABLE 22

Genotype frequency of EDN1/K198N polymorphism in male and female subjects

| Polymorphism | Male | | | | Female | | | |
|---|---|---|---|---|---|---|---|---|
| | | Genotype frequency | | | | Genotype frequency | | |
| | | KK | KN + NN | p value | | KK | KN + NN | p value |
| EDN1/K198N | Control (n = 100) | 46 (46.0) | 54 (54.0) | | Control (n = 124) | 52 (41.9) | 72 (58.1) | |
| | OAG (n = 218) | 112 (51.4) | 106 (48.6) | 0.373 | OAG (n = 207) | 114 (55.1) | 93 (44.9) | 0.021* |
| | POAG (n = 99) | 48 (48.5) | 51 (51.5) | 0.726 | POAG (n = 76) | 38 (50.0) | 38 (50.0) | 0.266 |
| | NTG (n = 119) | 64 (53.8) | 55 (46.2) | 0.251 | NTG (n = 131) | 76 (58.0) | 55 (42.0) | 0.010* |

Data are n (%).

*P < 0.05 ($\chi^2$ test).

In the EDN1/K198N polymorphism, genotype distributions diversed according to gender. The KK genotype for this polymorphism was significantly more prevalent in female NTG patients (p = 0.010 vs. female controls) than in male NTG patients (p = 0.251 vs. male controls).

TABLE 23

Characteristics of glaucoma patients according to genotype

| Polymorphism | Type of glaucome | Characteristic | Genotype | | p value |
|---|---|---|---|---|---|
| | | | GG + GA | AA | |
| EDNRA/G – 231A | NTG | Age at diagnosis (years) | 56.9 ± 13.1 (n = 192) | 53.6 ± 13.5 (n = 55) | 0.102 |
| | | Untreated maximum IOP (mmHg) | 17.1 ± 2.3 (n = 188) | 16.4 ± 2.2 (n = 52) | 0.052 |
| | | Visual field score at diagnosis | 2.7 ± 0.6 (n = 194) | 3.0 ± 0.8 (n = 55) | 0.043* |
| | | | TT | TC + CC | |
| EDNRA/H323H | NTG | Age at diagnosis (years) | 55.7 ± 13.5 (n = 131) | 56.6 ± 12.9 (n = 117) | 0.508 |
| | | Untreated maximum IOP (mmHg) | 17.2 ± 2.2 (n = 129) | 16.6 ± 2.3 (n = 112) | 0.040* |
| | | Visual field score at diagnosis | 2.8 ± 0.7 (n = 133) | 2.7 ± 0.7 (n = 117) | 0.307 |
| | | | CC + CG | GG | |
| EDNRA/C + 70G | NTG | Age at diagnosis (years) | 55.7 ± 13.3 (n = 194) | 57.8 ± 12.7 (n = 54) | 0.373 |
| | | Untreated maximum IOP (mmHg) | 17.0 ± 2.2 (n = 188) | 16.5 ± 2.3 (n = 53) | 0.141 |
| | | Visual field score at diagnosis | 2.7 ± 0.7 (n = 195) | 3.0 ± 0.7 (n = 55) | 0.014* |

Data are means ± SD.

*P < 0.05 (Mann-Whitney U test).

The AA genotype of EDNRA/G – 231A and the GG genotype of EDNRA/C + 70G were associated with worse visual field defects in NTG patients (p = 0.043 and 0.014, respectively). The EDNRA/H323H polymorphism influenced untreated maximum IOP among NTG patients (p = 0.040).

In male subjects, the following correlations were confirmed:

1) The A138 insertion/deletion (A138I/D) polymorphism in exon 1 of the Endothelin-1 gene is associated with both of POAG and NTG (Table 24).

2) The −231A>G polymorphism of promoter region of the Endothelin receptor A gene is associated with NTG, especially with patients with intraocular pressure at less than 15 mmHg (Table 25).

3) The CAC to CAT substitution at codon No. 233 in exon 6 of the Endothelin receptor A gene (His323His) is associated with NTG, especially with patients with intraocular pressure at less than 15 mmHg (Table 26).

4) The CTG to CTA substitution at codon No. 277 in exon 4 of the Endothelin receptor B gene is associated with both of POAG and NTG (Table 27).

In female patients, following correlations were confirmed:

1) The AAG to AAT substitution at codon No. 198 of the endothelin-1 gene (Lys198Asn) is associated with NTG (Table 28).

2) The −1370T>G polymorphism of the Endothelin-1 gene promoter region is associated with NTG (Table 29).

3) The +70C>G (70 bases from the stop codon) polymorphism in 3' non-coding region of the Endothelin receptor A is associated with POAG (Table 30).

4) The +1222C>T (1222 bases from the stop codon) polymorphism in 3' non-coding region of the Endothelin receptor A is associated NTG (wherein the intraocular pressure is 16 mmHg-21 mmHg) (Table 31).

TABLE 24

| Endothelin A138I/D (Male) | | | | | | | | | | | |
|---|---|---|---|---|---|---|---|---|---|---|---|
| | | Genotype Frequency | | | | Genotype Frequency | | | Genotype Frequency | | $\chi^2$ |
| | N | I/I | I/D | D/D | p | I/I | I/D + D/D | p | I/I + I/D | D/D | test p |
| Control | 100 | 4 | 34 | 62 | | 4 | 96 | | 38 | 62 | |
| POAG | 100 | 3 | 21 | 76 | | 3 | 97 | | 24 | 76 | 0.032 |
| NTG | 119 | 1 | 28 | 90 | | 1 | 118 | | 29 | 90 | 0.029 |

TABLE 25

| Endothelin Receptor A −231A > G (Male) | | | | | | | | | | | |
|---|---|---|---|---|---|---|---|---|---|---|---|
| | | Genotype Frequency | | | | Genotype Frequency | | | Genotype Frequency | | $\chi^2$ |
| | N | AA | AG | GG | p | AA | AG + GG | p | AA + AG | GG | test p |
| Control | 100 | 22 | 45 | 33 | | 22 | 78 | | 67 | 33 | |
| POAG | 100 | 24 | 51 | 25 | | 24 | 76 | | 75 | 25 | |
| NTG | 119 | 30 | 60 | 29 | | 30 | 89 | | 90 | 29 | |
| H-NTG | 89 | 17 | 45 | 27 | | 17 | 72 | | 62 | 27 | |
| L-NTG | 25 | 11 | 12 | 2 | 0.017 | 11 | 14 | 0.026 | 23 | 2 | 0.025 |

H-NTG: NTG patients with intraocular pressure at 16 mmHg-21 mmHg.
L-NTG: NTG patients with maximal intraocular pressure at 15 mmHg or less.

TABLE 26

| Endothelin Receptor A H323H C > T His323His (Male) | | | | | | | | | | | |
|---|---|---|---|---|---|---|---|---|---|---|---|
| | | Genotype Frequency | | | | Genotype Frequency | | | Genotype Frequency | | $\chi^2$ |
| | N | CC | CT | TT | p | CC | CT + TT | p | CC + CT | TT | test p |
| Control | 100 | 9 | 40 | 51 | | 9 | 91 | | 49 | 51 | |
| POAG | 100 | 7 | 38 | 55 | | 7 | 93 | | 45 | 55 | |
| NTG | 119 | 11 | 50 | 58 | | 11 | 108 | | 61 | 58 | |
| H-NTG | 89 | 7 | 32 | 50 | | 7 | 82 | | 39 | 50 | |
| L-NTG | 25 | 4 | 14 | 7 | | 4 | 21 | | 18 | 7 | 0.039 |

H-NTG: NTG patients with intraocular pressure at 16 mmHg-21 mmHg.
L-NTG: MTG patients with maximal intraocular pressure at 15 mmHg or less.

TABLE 27

| Endothelin Receptor B L277L G > A Leu277Leu (Male) | | | | | | | | | | | |
|---|---|---|---|---|---|---|---|---|---|---|---|
| | | Genotype Frequency | | | | Genotype Frequency | | | Genotype Frequency | | $\chi^2$ |
| | n | GG | GA | AA | p | GG | GA + AA | p | GG + GA | AA | test p |
| Control | 100 | 18 | 41 | 41 | | 18 | 82 | | 59 | 41 | |
| POAG | 100 | 26 | 48 | 26 | | 26 | 74 | | 74 | 26 | 0.025 |
| NTG | 119 | 26 | 61 | 32 | | 26 | 93 | | 87 | 32 | 0.027 |

TABLE 28

| Endothelin Lys198Asn G > T or K198N (Female) | | | | | | | | | | | |
|---|---|---|---|---|---|---|---|---|---|---|---|
| | | Genotype Frequency | | | | Genotype Frequency | | | Genotype Frequency | | $\chi^2$ |
| | N | KK | KN | NN | p | KK | KN + NN | p | KK + KN | NN | test p |
| Control | 124 | 52 | 59 | 13 | | 52 | 72 | | 111 | 13 | |
| POAG | 76 | 38 | 33 | 5 | | 38 | 38 | | 71 | 5 | |
| NTG | 131 | 76 | 38 | 17 | 0.009 | 76 | 55 | 0.010 | 114 | 17 | |

TABLE 29

| Endothelin −1370T > G (Female) | | | | | | | | | | | |
|---|---|---|---|---|---|---|---|---|---|---|---|
| | | Genotype Frequency | | | | Genotype Frequency | | | Genotype Frequency | | $\chi^2$ |
| | N | TT | TG | GG | p | TT | TG + GG | p | TT + TG | GG | test p |
| Control | 124 | 66 | 56 | 2 | | 66 | 58 | | 122 | 2 | |
| POAG | 76 | 49 | 24 | 3 | | 49 | 27 | | 73 | 3 | |
| NTG | 131 | 84 | 39 | 8 | 0.013 | 84 | 47 | | 123 | 8 | |

TABLE 30

| Endothelin Receptor A +70C > G (Female) | | | | | | | | | | | |
|---|---|---|---|---|---|---|---|---|---|---|---|
| | | Genotype Frequency | | | | Genotype Frequency | | | Genotype Frequency | | $\chi^2$ |
| | N | CC | CG | GG | p | CC | CG + GG | p | CC + CG | GG | test p |
| Control | 124 | 29 | 59 | 36 | | 29 | 95 | | 88 | 36 | |
| POAG | 76 | 28 | 32 | 16 | | 28 | 48 | 0.041 | 60 | 16 | |
| NTG | 131 | 35 | 66 | 30 | | 35 | 96 | | 101 | 30 | |

TABLE 31

| Endothelin Receptor A +1222C > T (Female) | | | | | | | | | | | |
|---|---|---|---|---|---|---|---|---|---|---|---|
| | | Genotype Frequency | | | | Genotype Frequency | | | Genotype Frequency | | |
| | N | CC | CT | TT | p | CC | CT + TT | p | CC + CT | TT | $\chi^2$ test p |
| Control | 124 | 74 | 42 | 8 | | 74 | 50 | | 116 | 8 | |
| POAG | 76 | 40 | 30 | 6 | | 40 | 36 | | 70 | 6 | |
| NTG | 131 | 66 | 54 | 11 | | 66 | 65 | | 120 | 11 | |
| H-NTG | 92 | 42 | 42 | 8 | | 42 | 50 | 0.041 | 84 | 8 | |
| L-NTG | 35 | 21 | 11 | 3 | | 21 | 14 | | 32 | 3 | |

H-NTG: NTG patients with intraocular pressure at 16 mmHg-21 mmHg.
L-NTG: MTG patients with maximal intraocular pressure at 15 mmHg or less.

Partial nucleotide sequences of endothelin-1 (EDN1) and endothelin receptor A (EDNRA) and endothelin receptor B (EDNRB) comprising the targeted polymorphisms are shown below

```
EDNI -1370 (underlined) T > G

2101 ttgaattcca ccctccatcc ccagaaaaac tggagtaaaa caaaaagagg agatggacaa  (SEQ ID NO: 142)

2161 agtgtgtatt tgatggcatc ccctgggaag agactctaaa tttatcccat aggtcttact

2221 gggccactgt gagcgcttg gtggagaaca aacaaaaatt ctgggtgctc agttgtctaa

2281 cctgaaaaat gggactagcg gaaaaagcca atgtgttcca tgcacctttt gctttcttta

2341 ttaaggcatg atgtcacctg tacagtaact gccctgtgtg tacttcaggg


EDN1 +138 (underlined) ins/del (each one of the a at 3743-3745)

3661 ccagctctcc accgccgcgt gcgcctgcag acgctccgct cgctgccttc tctcctggca  (SEQ ID NO: 143)

3721 ggcgctgcct tttctccccg ttaaagggca cttgggctga aggatcgctt tgagatctga

3781 ggaacccgca gcgctttgag ggacctgaag ctgtttttct tcgttttcct ttgggttcag

3841 tttgaacggg aggtttttga tcccttttttt tcagaatgga ttatttgctc atgattttct

(atg is the initiation codon)
```

-continued

EDNRA +70 (underlined) C > G 63601 atccagtgga agaaccacga tcaaaacaac cacaacacag accggagcag ccataaggac (SEQ ID NO: 144)

63661 agcatgaact gaccaccctt agaagcactc ctcggtactc ccataatcct ctcggagaaa 63721 aaaatcacaa ggcaactgtg actccgggaa tctcttctct gatccttctt ccttaattca 63781 ctcccacacc caagaagaaa tgctttccaa aaccgcaagg gtagactggt ttatccaccc 63841 acaacatcta cgaatcgtac ttctttaatt gatctaattt acatattctg cgtgttgtat (tga is the translation termination codon)

EDNRA +1222 (underlined) C > T 64741 ttaatttttc ttaaaatgtt aactggcagt aagtcttttt tgatcattcc cttttccata (SEQ ID NO: 145)

64801 taggaaacat aattttgaag tggccagatg agtttatcat gtcagtgaaa aataattacc 64861 cacaaatgcc accagaactt aacgattctt cacttcttgg ggttttcagt atgaacctaa 64921 ctccccaccc caacatctcc ctcccacatt gtcaccattt caaagggccc acagtgactt 64981 ttgctgggca ttttcccaga tgtttacaga ctgtgagtac agcagaaaat cttttactag EDNRA codon No. 323 (underlined) (T > C) His323His 60721 gaggtagagg cagtgtaagc caggctgttc tcctggctct tctttgaatt attctttctc (SEQ ID NO: 146)

60781 tggtgtctgc tacttcttgg tactgtagtt cttgcatcta gtataaaaac actaaatttg 60841 ttgtcctatt tttttctcac tttcctttag cgtcgagaag tggcaaaaac agttttctgc 60901 ttggttgtaa tttttgctct ttgctggttc cctctt*cat*t taagccgtat attgaagaaa 60961 actgtgtata acgagatgga caagaaccga tgtgaattac ttaggtatga tcctgtgtac 61021 tcgctagaaa attggagttt ctcagatttt catatttata atacttttac aaaaccagct EDNRA -231 (underlined) A > G 2041 ggaggagacg gggaggacag actggaggcg tgttcctccg gagttttctt tttcgtgcga (SEQ ID NO: 147)

2101 gccctcgcgc gcgcgtacag tcatcccgct ggtctgacga ttgtggagag gcggtggaga 2161 ggcttcatcc atcccacccg gtcgtcgccg gggattgggg tcccagcgag acctccccgg 2221 gagaagcagt gcccaggagg ttttctgaag ccggggaagc tgtgcagccg aagccgccgc 2281 cgcgccggag cccgggacac cggccaccct ccgcgccacc caccctcgcc ggctccggct 2341 tcctctggcc caggcgccgc gcggacccgg cagctgtctg cgcacgccga gctccacggt EDNRB codon No. 27 (underlined) Leu277Leu (CTG to CTA)

75361 taatcattcc ctgatgaatt tttttaagtt taacatttgt tatataagat tttcttacag (SEQ ID NO: 148)

75421 aggagtatta atcgtaaaaa ttctctcatc cctatagttt tacaagacag caaaagattg 75481 gtgg*ctg*ttc agtttctatt tctgcttgcc attggccatc actgcatttt tttatacact 75541 aatgacctgt gaaatgttga gaaagaaaag tggcatgcag attgctttaa atgatcacct 75601 aaagcaggta agaaaataca aatatttgat aactcgtggt tgaatttata attatgaata

EXAMPLE 9

Association Between Gene Polymorphism of β1 Adrenergic Receptor (ADRB1) and Glaucoma Methods Association between gene polymorphism of ADRB1 and glaucoma was examined among POAG, NTG patients and normal (control) subjects using PCR-RFLP techniques (Table 32-1).

TABLE 32-1

Primer sequences

| Gene | | Primer sequences | Restriction Enzyme | |
|---|---|---|---|---|
| ADRB1 | F | CCG CCT CTT CGT CTT CTT CAA CTG | BsmF1 | (SEQ ID NO: 149) |
| Gly389Arg | R | GAT AGC AGG TGA ACT CGA AGC CCA | | (SEQ ID NO: 150) |

Results

As shown in Table 32-2, the polymorphism of Gly389Arg in ADRB1 is associated with NTG (Table 32-2).

TABLE 32-2

β1-Adrenalin Receptor Gly389Arg

| | N | Genotype Frequency | | | | Genotype Frequency | | | Genotype Frequency | | $\chi^2$ test p |
|---|---|---|---|---|---|---|---|---|---|---|---|
| | | CC | CG | GG | p | CC | CG + GG | p | CC + CG | GG | |
| Control | 240 | 147 | 78 | 15 | | 147 | 93 | | 225 | 15 | |
| POAG | 191 | 127 | 58 | 6 | | 127 | 64 | | 185 | 6 | |
| NTG | 284 | 197 | 80 | 7 | 0.038 | 197 | 87 | | 277 | 7 | 0.031 |

Partial nucleotide sequence of β1-Adrenalin Receptor comprising the targeted polymorphism.

```
B1AR codon 389(underlined GGA(Gly) to CGA(Arg) Gly389Arg
1021 ttcctggcca acgtggtgaa ggccttccac cgcgagctgg tgcccgaccg cctcttcgtc  (SEQ ID NO: 151)

1081 ttcttcaact ggctgggcta cgccaactcg gccttcaacc ccatcatcta ctgccgcagc

1141 cccgacttcc gcaaggcctt ccagggactg ctctgctgcg cgcgcagggc tgcccgccgg

1201 cgccacgcga cccacggaga ccggccgcgc gcctcgggct gtctggcccg gcccggaccc

1261 ccgccatcgc ccggggccgc ctcggacgac gacgacgacg atgtcgtcgg ggccacgccg
```

EXAMPLE 10

Correlation Between Gene Polymorphism of E-Selectin and Glaucoma

Methods

Relationship between a E-selectin gene polymorphism and glaucoma among subject with POAG, NTG and normal subject was examined by means of Invader® method.

Invader® oligonucleotides (Invader® probe) used to detect the C/T polymorphism of SELE gene are shown in Table 33-1.

TABLE 33-1

| Mutation | nucleotide change | Target | Probe | Sequence | Length (bp) | Tm (° C.) | Dye | |
|---|---|---|---|---|---|---|---|---|
| SELE 1402 CT | C to T | Anti-sense | Wild | Flap-CATGGATCAACTCAACTTGA | 32 | 63.8 | RED | (SEQ ID NO: 152) |
| | | | Mutant | Flap-TATGGATCAACTCAACTTGAG | 31 | 63.4 | FAM | (SEQ ID NO: 153) |
| | | | Invader | TCTTGTGCCTTCAGCTGTGAGGAGGGATTTGAATTAA | 37 | 77.2 | | (SEQ ID NO: 154) |

Results

The 1402C>T polymorphism of E-selectin gene was confirmed being associated with both of POAG and NTG. Table 33-2).

TABLE 33-2

E-selectin 1402C > T

| | | Genotype Frequency | | | | Genotype Frequency | | | Genotype Frequency | | |
|---|---|---|---|---|---|---|---|---|---|---|---|
| | N | CC | CT | TT | p | CC | CT + TT | P | CC + CT | TT | $\chi^2$ test p |
| Control | 224 | 138 | 67 | 19 | | 138 | 86 | | 205 | 19 | |
| POAG | 250 | 150 | 90 | 10 | | 150 | 100 | | 240 | 10 | 0.042 |
| NTG | 176 | 117 | 53 | 6 | | 117 | 59 | | 170 | 6 | 0.037 |

Partial nucleotide sequence of E-selectin comprising the targeted polymorphism is as follows:

```
SELE No. 1402 (underlined) C > T
7561 tgtttttatt ttattttaag ataaaaagaa ctattgaaga gcttgggaac ttggttacct  (SEQ ID NO: 155)

7621 tgggaaacgt attgctggag atgcaaacaa acttctaaag tgctctctcg tgtgttccag

7681 ctgtgagatg cgatgctgtc caccagcccc cgaagggttt ggtgaggtgt gctcattccc

7741 ctattggaga attcacctac aagtcctctt gtgccttcag ctgtgaggag ggatttgaat

7801 tacatggatc aactcaactt gagtgcacat ctcagggaca atggacagaa gaggttcctt

7861 cctgccaagg tagaattgag tgcagacttt tttagggtac aggtcaaata cttcataaag

7921 tttctgaacc tagattgccc caaaggggtt tggtcctaat ttcctacatg ctgaaaacta

7981 agtagcgctt acactttaca ttcattgttg acttttaagc aagttttgga agttttccag

8041 tagatttttc tgaaactctg cctgtgtacc taacatttgc agtggtaaaa tgttcaagcc

8101 tggcagttcc gggaaagatc aacatgagct gcagtgggga gcccgtgttt ggcactgtgt
```

EXAMPLE 11

Paraoxonase 1 Gene Polymorphisms are Associated with Clinical Features of Open-Angle Glaucoma Purpose: Oxidative derivatives of low-density lipoprotein (LDL) are injurious to endothelium. Endothelial dysfunction is known to be involved in the pathogenesis of open-angle glaucoma (OAG). High-density lipoprotein (HDL) prevents the oxidative modification of LDL. We examined whether polymorphisms in the paraoxonase 1 (PON1), PON2, and platelet-activating factor acetylhydrolase (PAF-AH) genes, HDL-associated antioxidant enzymes, were associated with OAG in a Japanese population.

Materials and Methods

Patients and Control Study Subjects

Six hundred and ninety-eight blood samples were collected at seven Japanese institutions. Subjects included 190 POAG patients, 268 NTG patients, and 240 normal controls. None subject was related to any other.

Age at the blood sampling (mean±SD) was 65.3±11.9 years in POAG patients, 58.8±13.4 years in NTG patients, and 69.7±11.2 years in normal subjects, normal control subjects were significantly older than POAG patients (p<0.001) or NTG patients (p<0.001), which would reduce the likelihood of control subjects eventually developing glaucoma.

Clinical features recorded in glaucoma patients were age at diagnosis, IOP at diagnosis, and visual field defects at diagnosis. Severity of visual field defects was scored from 1 to 5. Data obtained with different perimeters were combined using a five-point scale defined as follows: 1=no alternation; 2=early defect; 3=moderate defect; 4=severe defect; 5=light perception only or no vision. Field defects were judged to be early, moderate, or severe according to Kozaki's classification based on Goldmann perimetry or by the classification used for the Humphrey field analyzer. The former classification has been most widely used in Japan so far.

All patients received serial ophthalmic examinations including IOP measurements by Goldmann applanation tonometry, Humphrey perimetry (30-2) or Goldmann perimetry, gonioscopy, and optic disc examination including fundus photograph. All of glaucoma patients were diagnosed according to the following criteria: the presence of typical optic disc damage with glaucomatous cupping (cup/disc ratio>0.7) and loss of neuroretinal rim; reproducible visual field defects compatible with the glaucomatous cupping; and open angles on gonioscopy. Among the OAG patients, POAG was diagnosed if they had an IOP>21 mm Hg at any time during the follow-up period. Patients with exfoliative glaucoma, pigmentary glaucoma, and corticosteroid-induced glaucoma were excluded. Among the OAG patients, NTG was diagnosed when: the untreated peak IOP was consistently equal to or less than 21 mm Hg at all times including the 3 baseline measurements and that during the diurnal testing values (every 3 hours from 6 AM to 24 PM); the peak IOP with or without medication after diagnosis was consistently <22 mm Hg throughout the follow-up period; and the absence of a secondary cause for glaucomatous optic neuropathy, such as a previously elevated IOP following trauma, a period of steroid administration, or uveitis.

Control subjects were recruited from among Japanese individuals who had no known eye abnormalities except for cataracts. These subjects numbered 196 and were older than 40 years, with IOP below 20 mm Hg, no glaucomatous disc change, and no family history of glaucoma.

Genotyping

Genomic DNA was isolated from peripheral blood lymphocytes by standard methods. Four SNPs were then detected in all participants: two for PON1 (L55M, Q192R); one for PON2 (Cys311Ser, C311S); and one for PAF-AH (V279F).

These SNPs were genotyped by means of the Invader® assay (Third Wave Technologies, Inc, Madison, Wis., USA) which was recently developed for high-throughput genotyping of SNPs. The oligonucleotide sequences of primary probes and Invader® probes used in this study were listed in Table 34.

sion model to confirm the association between the three clinical variables and the genotype. Comparison of IOPs between genotype groups of Q192R in the PON 1 gene was performed by Kruskal-Wallis test. Statistical analyses were carried out with SPSS (version 12.0; SPSS, Chicago, Ill.). A value of $p<0.05$ was considered to indicate significance.

Results

Distributions of genotypes for the four SNPs in glaucoma patients and controls are shown in Table 35. The L55M polymorphism of the PON1 gene had a significantly different genotype frequency in patients with NTG.

TABLE 34

Sequences of primary probes and Invader oligonucleotides used in assays

| Polymorphism | Nucleotide change | Target | Probe | Probe | Sequence | |
|---|---|---|---|---|---|---|
| PON M55L | A to T | Sense | Wild | A probe | Flap sequence-TGTCTTCAGAGCCAGTT | (SEQ ID NO: 156) |
| | | | Mutant | T probe | Flap sequence-AGTCTTCAGAGCCAGTT | (SEQ ID NO: 157) |
| | | | Invader | Invader | AGAGCTAATGAAAGCCAGTCCATTAGGCAGTATCTCCAC | (SEQ ID NO: 158) |
| PON Q192R | A to G | Anti-sense | Wild | A probe | Flap sequence-AATCCTGGGAGATGTATTTG | (SEQ ID NO: 159) |
| | | | Mutant | G probe | Flap sequence-GATCCTGGGAGATGTATTTG | (SEQ ID NO: 160) |
| | | | Invader | Invader | AGCACTTTTATGGCACAAATGATCACTATTTTCTTGACC CCTACTTACT | (SEQ ID NO: 161) |
| PAF-AH V279F | G to T | Sense | Wild | G probe | Flap sequence-CCGTTGCTCCACCA | (SEQ ID NO: 162) |
| | | | Mutant | T probe | Flap sequence-ACGTTGCTCCACCA | (SEQ ID NO: 163) |
| | | | Invader | Invader | ACTATCTTATTTTCTTACCTGAATCTCTGATCTTCACTA AGAGTCTGAATAAT | (SEQ ID NO: 164) |

Statistical Analysis

Hardy-Weinberg equilibrium was assessed by chi-squared analysis. Frequencies of the genotypes and alleles were compared between cases and controls by chi-squared analysis. Multivariate analyses were performed with a logistic regres- Distribution of genotypes for polymorphisms in the PON2 gene and PAF-AH gene showed no significant differences between any patient group and controls (Table 35). And there was no significant difference in allele frequency of the 4 SNPs.

TABLE 35

Genotype frequency of PON1, PON2, and PAF-AH polymorphisms in Japanese control subjects and glaucoma patients

| | PON1/L55M | | | | PON1/Q192R | | | | PON2/C311S | | | | PAF-AH/V279F | | | |
|---|---|---|---|---|---|---|---|---|---|---|---|---|---|---|---|---|
| Phenotype | LL (%) | LM (%) | MM (%) | P | QQ (%) | QR (%) | RR (%) | P | CC (%) | CS (%) | SS (%) | P | VV (%) | VF (%) | FF (%) | P |
| Control | 190 | 34 | 0 | | 32 | 105 | 85 | | 10 | 74 | 140 | | 153 | 62 | 9 | |
| (N = 224) | 84.8 | 15.2 | 0.0 | | 14.4 | 47.3 | 38.3 | | 4.5 | 33.0 | 62.5 | | 68.3 | 27.7 | 4.0 | |
| POAG | 145 | 29 | 0 | | 22 | 74 | 78 | | 3 | 73 | 100 | | 293 | 113 | 14 | |
| (N = 174) | 83.3 | 16.7 | 0.0 | 0.922 | 12.6 | 42.5 | 44.8 | 0.421 | 1.7 | 41.5 | 56.8 | 0.093 | 69.8 | 26.9 | 3.3 | 0.874 |
| NTG | 224 | 19 | 3 | | 44 | 100 | 102 | | 9 | 88 | 151 | | 121 | 48 | 5 | |
| (N = 246) | 91.1 | 7.7 | 1.2 | 0.009 | 17.9 | 40.7 | 41.5 | 0.265 | 3.6 | 35.5 | 60.9 | 0.814 | 69.5 | 27.6 | 2.9 | 0.824 |

The distributions of the combined two polymorphisms of the PON1 gene in OAG population are shown in Table 36. As clearly shown, methionine (M) at position 55 (M allele) was rarely associated with arginine (R) at position 192 (R allele). Analysis confirmed a linkage disequilibrium between the polymorphisms giving rise to leuicine (L) at position 55 and arginine (R) at position 192 (P<0.001).

TABLE 36

Distribution of genotypes defined by polymorphisms of PON1 gene affecting amino acids at position 55 and 192

| | | Q192R | | | | | | Q192R | |
|---|---|---|---|---|---|---|---|---|---|
| | | QQ | QR | RR | Total | | | Non R-carrier | R-carrier |
| L55M | LL | 72 | 221 | 265 | 558 | L55M | L-carrier | 95 | 544 |
| | LM | 23 | 58 | 0 | 81 | | Non L-carrier | 3 | 0 |
| | MM | 3 | 0 | 0 | 3 | | | | |
| | Total | 98 | 279 | 265 | 642 | | | | |

Characteristics of patients were examined in dominant and recessive models for each polymorphism. In the recessive mode, no significant difference was seen in three characteristics in patients with OAG for any polymorphisms. Significant differences with the dominant model of PON1 polymorphisms are shown in Tables 37 and 38. For L55M polymorphism in the PON1 gene in OAG patients, the LL group (non-55M carriers) was significantly younger at diagnosis than the LM+MM group (55M carriers) (56.8±12.8 years vs. 60.1±11.4, p=0.028) (Table 37). This association was not observed in POAG patients, but in NTG patients (55.6±13.1 years vs. 63.7±9.6, p=0.001).

For Q192R polymorphism, untreated maximum IOPs at diagnosis were significantly higher in OAG patients with QR+RR group (192R carriers) (21.5±7.4 mm Hg) than those with QQ group (non-192Rcarriers) (18.7±5.3 mm Hg, P=0.006, Table 38). Untreated maximum IOPs were higher in 192R carriers than in non-carriers among POAG patients (27.5±7.0 mm Hg vs. 24.0±4.9 for POAG, p=0.049) as well as among NTG patients (15.8±2.8 mm Hg vs. 16.7±2.4 for NTG, p=0.030).

TABLE 37

Clinical characteristics of NTG patients according to genotype of L55M in the PON1 gene

| | | Genotype | | |
|---|---|---|---|---|
| Phenotype | Clinical characteristics | LL | LM + MM | P value* |
| OAG | Age at diagnosis (ys) | 56.8 ± 12.8 (n = 473) | 60.1 ± 11.4 (n = 62) | 0.028 |
| | IOP at diagnosis (mmHg) | 21.1 ± 7.2 (n = 409) | 21.5 ± 6.1 (n = 58) | 0.681 |
| | Visual field score at diagnosis | 2.9 ± 0.8 (n = 476) | 3.0 ± 0.7 (n = 63) | 0.899 |
| POAG | Age at diagnosis (ys) | 58.6 ± 12.2 (n = 199) | 58.2 ± 12.3 (n = 34) | 0.836 |
| | IOP at diagnosis (mmHg) | 27.3 ± 7.1 (n = 170) | 25.9 ± 4.8 (n = 31) | 0.352 |
| | Visual field score at diagnosis | 3.9 ± 0.9 (n = 200) | 3.0 ± 0.7 (n = 35) | 0.475 |
| NTG | Age at diagnosis (ys) | 55.6 ± 13.1 (n = 274) | 63.7 ± 9.6 (n = 28) | 0.001 |
| | IOP at diagnosis (mmHg) | 16.6 ± 2.5 (n = 239) | 16.6 ± 2.7 (n = 27) | 0.984 |
| | Visual field score at diagnosis | 2.8 ± 0.7 (n = 276) | 2.9 ± 0.7 (n = 28) | 0.343 |

P value* with Logistic regression analyses

TABLE 38

Clinical characteristics of glaucoma patients according to genotype of Q192R in the PON1 gene

| | | Genotype | | |
|---|---|---|---|---|
| Phenotype | Clinical characteristics | QQ | QR + RR | P value* |
| OAG | Age at diagnosis (ys) | 56.2 ± 13.9 (n = 77) | 57.5 ± 12.4 (n = 468) | 0.974 |
| | IOP at diagnosis (mmHg) | 18.7 ± 5.3 (n = 66) | 21.5 ± 7.4 (n = 409) | 0.006 |
| | Visual field score at diagnosis | 2.7 ± 0.7 (n = 77) | 2.9 ± 0.8 (n = 472) | 0.100 |
| POAG | Age at diagnosis (ys) | 55.2 ± 12.8 (n = 29) | 58.9 ± 12.0 (n = 210) | 0.259 |
| | Untreated IOP at diagnosis (mmHg) | 24.0 ± 4.9 (n = 23) | 27.5 ± 7.0 (n = 183) | 0.049 |
| | Visual field score at diagnosis | 2.8 ± 0.7 (n = 29) | 3.1 ± 0.9 (n = 212) | 0.415 |
| NTG | Age at diagnosis (ys) | 56.8 ± 14.6 (n = 48) | 56.4 ± 12.7 (n = 258) | 0.395 |
| | Untreated IOP at diagnosis (mmHg) | 15.8 ± 2.8 (n = 43) | 16.7 ± 2.4 (n = 226) | 0.030 |
| | Visual field score at diagnosis | 2.7 ± 0.7 (n = 48) | 2.8 ± 0.7 (n = 260) | 0.155 |

P value* with Logistic regression analyses

The Gly192Arg (Q192R) polymorphism in PON1 gene was associated with POAG (Table 39). The Leu55Met polymorphism was associated with NTG, especially with less than 15 mmHg (Table 40)

TABLE 39

| PON1 Gln192Arg (Q192R) | | | | | | | | | | | | |
|---|---|---|---|---|---|---|---|---|---|---|---|---|
| | | Genotype Frequency | | | | Genotype Frequency | | | Genotype Frequency | | | |
| | N | QQ | QR | RR | p | QQ | QR + RR | p | QQ + QR | RR | $\chi^2$ test p |
| Control | 224 | 32 | 107 | 85 | | 32 | 192 | | 139 | 85 | |
| POAG | 110 | 14 | 39 | 57 | 0.049 | 14 | 96 | 0.021 | 53 | 57 | 0.016 |
| NTG | 160 | 32 | 66 | 62 | | 32 | 128 | | 98 | 62 | |

TABLE 40

| PON1 Leu55Met (L55M) | | | | | | | | | | | |
|---|---|---|---|---|---|---|---|---|---|---|---|
| | | Genotype Frequency | | | | Genotype Frequency | | | Genotype Frequency | | |
| | N | LL | LM | MM | p | LL | LM + MM | p | LL + LM | MM | $\chi^2$ test p |
| Control | 226 | 192 | 34 | 0 | | 192 | 34 | | 226 | 0 | |
| POAG | 110 | 97 | 13 | 0 | | 97 | 13 | | 110 | 0 | |
| NTG | 160 | 144 | 13 | 3 | 0.013 | 144 | 16 | | 157 | 3 | |
| H-NTG | 122 | 111 | 10 | 1 | | 111 | 11 | | 121 | 1 | |
| L-NTG | 34 | 29 | 3 | 2 | 0.034 | 29 | 5 | | 32 | 2 | 0.009 |

H-NTG: NTG patients with intraocular pressure at 16 mmHg-21 mmHg.
L-NTG: MTG patients with maximal intraocular pressure at 15 mmHg or less.

Conclusion: PON1 Gene Polymorphisms May Influence Features of Japanese Patients with OAG, Especially Those with NTG.

Partial nucleotide sequence of Paraoxonase 1 gene containing the targeted polymorphisms is as follows:

```
PON1 Codon 55 (underlined) TTG(Leu) to ATG(Met) (Leu55Met)
and
PON1 Codon 192 (underlined) CAA(Gln) to CGA(Arg) (Gln192Arg)
  1 agagcctcct agcccgtcgg tgtctgcgcc catcgatccc tttgtctatc cccgaccatg  (SEQ ID NO: 165)

 61 gcgaagctga ttgcgctcac cctcttgggg atgggactgg cactcttcag gaaccaccag

121 tcttcttacc aaacacgact taatgctctc cgagaggtac aacccgtaga acttcctaac

181 tgtaatttag ttaaaggaat cgaaactggc tctgaagact tggagatact gcctaatgga

241 ctggctttca ttagctctgg attaaagtat cctggaataa agagcttcaa ccccaacagt

301 cctggaaaaa tacttctgat ggacctgaat gaagaagatc caacagtgtt ggaattgggg

361 atcactggaa gtaaatttga tgtatcttca tttaaccctc atgggattag cacattcaca

421 gatgaagata atgccatgta cctcctggtg gtgaaccatc cagatgccaa gtccacagtg

481 gagttgttta aatttcaaga agaagaaaaa tcgcttttgc atctaaaaac catcagacat

541 aaacttctgc ctaatttgaa tgatattgtt gctgtgggac ctgagcactt ttatggcaca
```

-continued

```
601 aatgatcact attttcttga cccctactta caatcctggg agatgtattt gggtttagcg

661 tggtcgtatg ttgtctacta tagtccaagt gaagttcgag tggtggcaga aggatttgat

721 tttgctaatg gaatcaacat ttcacccgat ggcaagtatg tctatatagc tgagttgctg

781 gctcataaga ttcatgtgta tgaaaagcat gctaattgga ctttaactcc attgaagtcc

841 cttgacttta ataccctcgt ggataacata tctgtggatc ctgagacagg agacctttgg

901 gttggatgcc atcccaatgg catgaaaatc ttcttctatg actcagagaa tcctcctgca

961 tcagaggtgc ttcgaatcca gaacattcta acagaagaac ctaaagtgac acaggtttat
```

EXAMPLE 12

Evaluation of the Noelin 2 Gene in the Ethiology of Open-Angle Glaucoma

Purpose: To screen for mutations in the Noelin 2 gene in Japanese patients with open-angle glaucoma using denaturing high-performance liquid chromatography (DHPLC).

Methods

Subjects

A total of 616 blood samples were collected at eight institutions in Japan. There were 276 POAG patients, 340 NTG patients, and 300 normal controls, and none of the subjects was related to others in this study.

DNA Extraction and PCR Conditions

All of the blood samples were analyzed at Keio University. Genomic DNA was isolated from peripheral blood lymphocytes by phenol-chloroform extraction. The 6 exonic coding regions of the Noelin 2 gene were amplified by polymerase chain reaction (PCR) using the primer sets listed in Table 41.

In high-throughput analysis, samples from three patients were pooled. PCR was performed with a thermal cycler (iCycler, Bio-Rad; Hercules, Calif.) in a total volume of 20 μl containing; 45 ng of genomic DNA, 2 μl GeneAmp 10×PCR buffer II, 2 μl of GeneAmp dNTP mix with a 2.0 mM concentration of each dNTP, 2.4 μl of a 25 mM $MgCl_2$ solution; 4 pmol of each primer, and 0.1 U of AmpliTaq Gold DNA polymerase (Applied Biosystems, Foster City, Calif.). The PCR conditions were; denaturation at 95° C. for 9 min, followed by 35 cycles at 95° C. for 1 min, 65° C. or 67° C. for 30 sec (Table 1), and 72° C. for 1 min and 30 sec, and a final extension step at 72° C. for 7 min.

Denaturing HPLC Analysis

For high-throughput analysis, a 25 μl volume of PCR products from the three patients was automatically injected into the chromatograph for analysis using the WAVE® System for DHPLC analysis (Transgenomic, Omaha, Nebr.). The DHPLC melting temperatures are listed in Table 41.

When abnormal chromatographic patterns were detected in the pooled samples by the high-throughput protocol, the

TABLE 41

Primer sequences, PCR product sizes, and PCR annealing and DHPLC analysis temperatures

| Exon | | Primer Sequences (5' to 3') | PCR product size (bp) | PCR Tm (° C.) | DHPLC Tm (° C.) | |
|---|---|---|---|---|---|---|
| 1 | F | not determined | | | | |
| | R | not determined | | | | |
| 2 | F | GCGAGACCCTCACTGGGATT | 344 | 67 | 62.0, 63.0, 64.0 | (SEQ ID NO: 166) |
| | R | GCCTGGAGAGGAGCTGGATT | | | | (SEQ ID NO: 167) |
| 3 | F | GGTTGGGATTTGGGGAAGGA | 284 | 67 | 60.3, 62.3, 64.3 | (SEQ ID NO: 168) |
| | R | CCAGACATGACTCCATTGTAGGAA | | | | (SEQ ID NO: 169) |
| 4 | F | GAGTCAGAGGTTGGAGTCATGT | 249 | 65 | 62.7, 63.2, 63.7 | (SEQ ID NO: 170) |
| A | R | CCGTTGCTGCAGGTCCTCATA | | | | (SEQ ID NO: 171) |
| 4 | F | CAGACACGCGGACCATTGTA | 208 | 65 | 63.1, 64.1, 65.1 | (SEQ ID NO: 172) |
| B | R | GGGTGTGGCAGTCAGAGATCA | | | | (SEQ ID NO: 173) |
| 5 | F | CCCAACTTGATCACAGCACTT | 269 | 65 | 61.7, 63.7, 64.7 | (SEQ ID NO: 174) |
| | R | CTAGGCACCTATGGGCAGTCAA | | | | (SEQ ID NO: 175) |
| 6 | F | CTAATGGCTGTAGCTGGTGCT | 336 | 65 | 62.5, 63.5, 64.5 | (SEQ ID NO: 176) |
| A | R | GTAGGGGAAGGTGTTGTTGTAA | | | | (SEQ ID NO: 177) |
| 6 | F | CCAGAGCAACGTGGTGGTCA | 248 | 67 | | (SEQ ID NO: 178) |
| B | R | GGTAGCCGGTGTCCCAGGA | | | | (SEQ ID NO: 179) |
| 6 | F | GGCTGTGTACACCACCAACCA | 214 | 67 | | (SEQ ID NO: 180) |
| A | R | CTCGTAACTGGACGTGTTGGT | | | | (SEQ ID NO: 181) |
| 6 | F | CATGATCTGCGGTGTGCTCTA | 267 | 67 | 61.5, 62.0 | (SEQ ID NO: 182) |
| D | R | GCAGCCCGAGCCACAGCATT | | | | (SEQ ID NO: 183) |

sample was reanalyzed individually in the WAVE® System. The PCR product that showed the abnormal chromatographic pattern was then sequenced.

Direct DNA Sequencing

For direct sequencing, PCR products were purified with a QIA Quick PCR purification kit (Qiagen, Valencia, Calif.) to remove unused primers and precursors. The PCR products were directly sequenced with the same forward and reverse PCR amplification primers on an ABI310 automated sequencer using BigDye chemistry according to the manufacturer's recommended protocol (Applied Biosystems, Foster City, Calif.).

Screening Myocilin Gene

Two patients with glaucoma who harbored the mutation in the Noelin 2 gene were screened in the myocilin gene by DHPLC.

Genotyping Noelin 2 c.462G>A (Arg144Gln) Polymorphism

The G to A substitution at position c.462 in exon 4 of the Noelin 2 gene was detected by using restriction enzyme, BstU1. The G allele sequence was cut into two fragments (140 bp+200 bp) by BstU1, while the A allele sequence remained intact (344 bp).

The polymorphism was confirmed by restriction-enzyme assay and by the chromatographic pattern of DHPLC.

Statistical Analyses

The frequencies of the genotypes and alleles in patients and controls were compared with the chi-square test or Fisher's exact test. The Hardy-Weinberg equilibrium for the observed frequencies was also calculated. Statistical analysis was performed with SPSS program (SPSS Inc., Chicago, USA). A P value of <0.05 was considered to be significant.

Results

Noelin 2 Variants in Japanese Subjects

A total of 616 Japanese subjects were studied, and the results are presented in Table 42. Ten sequence changes were identified in the glaucoma patients and control subjects. Among these, two were missense changes, seven were synonymous codon changes, and one was a change in intron sequences. One possible disease causing-mutation, Arg144Gln, was identified in one POAG proband and one POAG proband, and was not present in the 300 normal Japanese controls. No significant difference was detected between glaucoma patients and controls for the Arg106Gln (P=0.30), Ala226Ala (P=0.30), and Arg427Arg (P=0.30).

The NTG patient with Arg144Gln harbored the Arg76Lys change in the myocilin gene.

A possible glaucoma-causing mutation in exon 4, Arg144Gln, was identified in 2(0.3%) of the 616 Japanese glaucoma patients.

TABLE 42

OLFM2 Variants oberved in glaucoma patients and control subjects

| Location | Sequence Changes | Codon Changes | Frequency in Subjects (%) POAG | NTG | Control |
|---|---|---|---|---|---|
| Exon 4 | c.462G > A | Arg144Gln | 1/276 (0.4) | 1/340 (0.3) | 0/300 (0) |
| Exon 3 | c.348G > A | Arg106Gln | 111/211 (52.6) | 135/276 (48.9) | 115/241 (47.7) |
| Exon 3 | c.289G > A | Thr86Thr | 1/211 (0.5) | 0/276 (0) | 0/241 (0) |
| Exon 3 | c.346G > A | Ala105Ala | 1/211 (0.5) | 0/276 (0) | 0/241 (0) |
| Exon 4 | c.451G > A | Lys140Lys | 1/276 (0.4) | 0/340 (0) | 0/300 (0) |
| Exon 4 | c.487G > A | Glu152Glu | 2/276 (0.7) | 0/340 (0) | 0/300 (0) |
| Exon 5 | c.628C > T | Thr199Thr | 0/211 (0) | 1/274 (0.4) | 0/241 (0) |
| Exon 5 | c.709G > A | Ala226Ala | 15/211 (7.1) | 27/274 (9.9) | 28/241 (11.6) |
| Exon 6 | c.1312C > T | Arg427Arg | 34/211 (16.1) | 45/270 (16.7) | 30/240 (12.5) |
| Intron 6 | c.1393 + 42T > C | | 117/210 (55.7) | N/C | N/C |

*Sequence variation was found by direct sequencing analysis.

Partial nucleotide sequence of Noelin 2 comprising the targeted polymorphisms is as follows:

```
Noelin 2 codon 144(underlined) CGG(Arg) to CAG(Gln): (GG:
200 bp + 144 bp, GA: 344 bp + 200 bp + 144 bp, AA: 344 bp)
(BstUI)
codon 140 (underlined) Lys140Lys (AAG > AAA)
codon 152 (underlined) Glu152Glu (GAG > CAA)
79741  ttagttccta caatggagtc atgtctggga agaatctagg gtccaatatg agccacatgt  (SEQ ID NO: 184)

79801  caagggccag gtgtgcatca aagacaaagg gtgaagttat gagtcagagg ttggagtcat

79861  gtctgggtca aaggccaggg gtcaggcttg gccatggttc catcttgatg cacaggagct

79921  gaaggacagg atgacggaac tgttgcccct gagctcggtc ctggagcagt acaaggcaga

79981  cacgcggacc attgtacgct tgcgggagga ggtgaggaat ctctccggca gtctggcggc

80041  cattcaggag gagatgggtg cctacgggta tgaggacctg cagcaacggg tgatggccct

80101  ggaggcccgg ctccacgcct gcgcccagaa gctgggtatg ccttggccct tgaccctgac

80161  ccctgatctc tgactgccac acccaactcc agtatcacct gtttgtgcct agaagctgga

80221  cacagttttg acctctaact tttaaacctc aacccttgac cttcctacct aaggctacac
```

79841-79862, 80164-80184; primers for detecting polymorphism at codon 144
79916-80131, coding region

EXAMPLE 13

Evaluation of the Heat Shock Protein 70-1 (HSP70-1) Gene in the Etiology of Glaucoma Association between glaucoma and gene polymorphism of HSP70-1 (Biogerontology 4: 215-220, 2003 and Hum Genet 114: 236-241, 2004) was examined among POAG, NTG patients and control subject using Invader assay.

The primary probes (wild and mutant probes) and Invader® oligonucleotides (Invader® probe) used to detect the polymorphism of HSP70-1 gene are shown in Table 43.

EXAMPLE 14

Evaluation of the Endothelin Converting Enzyme 1 (ECE1) Gene in the Etiology of Glaucoma Association between glaucoma and gene polymorphism of ECE1 was examined in POAG and NTG patients using Invader assay.

The primary probes (wild and mutant probes) and Invader® oligonucleotides (Invader® probe) used to detect the polymorphism of ECE1 gene are shown in Table 45.

TABLE 43

The oligonucleotide sequence of HSP70-1

| Gene | Polymorphism | nucleotide change | format | Probe | Sequence | |
|---|---|---|---|---|---|---|
| HSP70-1 | −110A > C | A to C | PCR | A | Flap sequence-TTTTCGCCTCCCGT | (SEQ ID NO: 185) |
| | | | | C | Flap sequence-GTTTCGCCTCCCGT | (SEQ ID NO: 186) |
| | | | | Invader | GCTGCCAGGTCGGGAATATTCCAGGGC | (SEQ ID NO: 187) |
| | | | PCR | F | CGCCATGGAGACCAACACCC | (SEQ ID NO: 188) |
| | | | | R | GCCGGTTCCCTGCTCTCTGTC | (SEQ ID NO: 189) |

Results

As shown in Table 44, the polymorphism of −110A>C in HSP70-1 is associated with glaucoma, especially POAG.

TABLE 44

Genotype distribution and allele frequency of HSP70-1 gene polymorphisms in glaucoma patients and controls
HSP70-1 −110A > C

| | Genotype Frequency | | | | | | | | | | Allele frequency | | |
|---|---|---|---|---|---|---|---|---|---|---|---|---|---|
| | AA | AC | CC | p | AA | AC + CC | p | AA + AC | CC | p | A | C | p |
| CONTROL | 67 | 130 | 44 | | 67 | 174 | | 197 | 44 | | 264 | 218 | |
| 241 | 27.8 | 53.9 | 18.3 | | 27.8 | 72.2 | | 81.7 | 18.3 | | 54.8 | 45.2 | |
| NTG | 106 | 130 | 54 | 0.069 | 106 | 184 | 0.032 | 236 | 54 | 0.914 | 342 | 238 | 0.169 |
| 290 | 36.6 | 44.8 | 18.6 | | 36.6 | 63.4 | | 81.4 | 18.6 | | 59.0 | 41.0 | |
| POAG | 84 | 94 | 33 | 0.026 | 84 | 127 | 0.007 | 178 | 33 | 0.460 | 262 | 160 | 0.026 |
| 211 | 39.8 | 44.5 | 15.6 | | 39.8 | 60.2 | | 84.4 | 15.6 | | 62.1 | 37.9 | |
| GLAUCOMA | 190 | 224 | 87 | 0.020 | 190 | 311 | 0.007 | 414 | 87 | 0.765 | 604 | 398 | 0.044 |
| 501 | 37.9 | 44.7 | 17.4 | | 37.9 | 62.1 | | 82.6 | 17.4 | | 60.3 | 39.7 | |

Partial nucleotide sequence of HSP70-1 comprising the targeted sequence is as follows:

HSP70-1 −110A > C (the following sequence is the C allele.)

```
  1 cgccatggag accaacaccc ttcccaccgc cactcccccct tcctctcagg gtccctgtcc  (SEQ ID NO: 190)

 61 cctccagtga atcccagaag actctggaga gttctgagca gggggcggca ctctggcctc

121 tgattggtcc aaggaaggct ggggggcagg acgggaggcg aaacccctgg aatattcccg

181 acctggcagc ctcatcgagc tcggtgattg gctcagaagg gaaaaggcgg gtctccgtga

241 cgacttataa aacgccaggg gcaagcggtc cggataacgg ctagcctgag gagctgctgc

301 gacagtccac taccttttc gagagtgact cccgttgtcc caaggcttcc cagagcgaac
```

TABLE 45

| The oligonucleotide sequence of ECE1 | | | | | | | | | | | |
|---|---|---|---|---|---|---|---|---|---|---|---|
| Gene | Polymorphism | nucleotide change | Target | format | arm | Probe | Sequence | Length (bp) | Tm (° C.) | Dye | |
| ECE1 | C-338A | C to A | Sense | PCR | 1-3 | C | Flap sequence-GTGGCCCAGAGCA | 23 | 63.0 | FAM | (SEQ ID NO: 191) |
| | | | | | | A | Flap-sequence-TTGGCCCAGAGCAA | 26 | 63.2 | RED | (SEQ ID NO: 192) |
| | | | | | | Invader | GGCAGATAACAAAAGTATGAGGAAGGTG CCCTCGATC | 37 | 77.5 | | (SEQ ID NO: 193) |
| | | | | | PCR | F | TAAGTCCCCTTCAACAACC | | | | (SEQ ID NO: 194) |
| | | | | | | R | AAGCTGAAAAGTACGCATAAATG | | | | (SEQ ID NO: 195) |

Results

As shown in Table 46, the polymorphism of −338C>A in ECE1 is associated with high IOP in NTG.

TABLE 46

Genotype distribution of ECE-1 gene polymorphisms in glaucoma patients and controls

| ECE-1/−338C > A polymorphism | | three genotypes | | | | | | |
|---|---|---|---|---|---|---|---|---|
| | Clinical chracteristics | CC | n | CA | n | AA | n | p |
| POAG | Age at diagnosis (ys) | 56.8 ± 12.2 | 68 | 57.8 ± 12.4 | 106 | 61.9 ± 10.5 | 34 | 0.089 |
| | IOP at diagnosis (mmHg) | 26.2 ± 5.8 | 60 | 26.8 ± 6.5 | 94 | 26.6 ± 4.8 | 32 | 0.301 |
| | Visual field score at diagnosis | 3.1 ± 1.0 | 68 | 3.1 ± 0.9 | 105 | 3.0 ± 0.8 | 35 | 0.917 |
| NTG | Age at diagnosis (ys) | 59.1 ± 13.0 | 97 | 54.2 ± 12.2 | 136 | 54.1 ± 14.2 | 53 | 0.015 |
| | IOP at diagnosis (mmHg) | 16.7 ± 2.4 | 91 | 16.8 ± 2.4 | 123 | 15.6 ± 2.6 | 46 | 0.024 |
| | Visual field score at diagnosis | 2.8 ± 0.7 | 99 | 2.8 ± 0.7 | 136 | 2.8 ± 0.7 | 53 | 0.704 |

| ECE-1/−338C > A polymorphism | | two genotypes | | | | | two genotypes | | | | |
|---|---|---|---|---|---|---|---|---|---|---|---|
| | Clinical chracteristics | CC | n | CA + AA | n | p | CC + CA | n | AA | n | p |
| POAG | Age at diagnosis (ys) | 56.8 ± 12.2 | 68 | 58.8 ± 12.1 | 140 | 0.262 | 57.4 ± 12.3 | 174 | 61.9 ± 10.5 | 34 | 0.032 |
| | IOP at diagnosis (mmHg) | 26.2 ± 5.8 | 60 | 26.7 ± 6.1 | 126 | 0.161 | 26.5 ± 6.2 | 154 | 26.6 ± 4.8 | 32 | 0.285 |
| | Visual field score at diagnosis | 3.1 ± 1.0 | 68 | 3.0 ± 0.9 | 140 | 0.715 | 3.1 ± 0.9 | 173 | 3.0 ± 0.8 | 35 | 0.761 |
| NTG | Age at diagnosis (ys) | 59.1 ± 13.0 | 97 | 54.1 ± 12.8 | 189 | 0.004 | 56.2 ± 12.7 | 233 | 54.1 ± 14.2 | 53 | 0.350 |
| | IOP at diagnosis (mmHg) | 16.7 ± 2.4 | 91 | 16.5 ± 2.5 | 169 | 0.507 | 16.7 ± 2.4 | 214 | 15.6 ± 2.6 | 46 | 0.007 |
| | Visual field score at diagnosis | 2.8 ± 0.7 | 99 | 2.8 ± 0.7 | 189 | 0.755 | 2.8 ± 0.7 | 235 | 2.8 ± 0.7 | 53 | 0.534 |

Partial nucleotide sequence of ECE-1 comprising the targeted polymorphism is shown as follows:

```
ECE1 -338C > A (underlined)
  1 ttttgtctgg tctttctagc attaaccccc tagacacacc taaggctgat gccgggggga (SEQ ID NO: 196)

 61 acctgtcttg attgctctgg gccacatcga gggcaccttc ctgatacttt tgttatctgc

121 cactggggac ccggttgttg aagggggact taagattttc tcgaaggagg ggtcactgtg

181 agggcctttc ctgcctgcta ggggcttcag tttgggggcc cccactcccg actccgggca

241 agggaggggt ccccatctcc cccgggcctc tcgggtcttg ggtctcccc gggaggccgg
```

EXAMPLE 15

Evaluation of the CD50 Gene in the Etiology of Open-Angle Glaucoma

Polymorphism of CD50 gene was identified using polymerase chain reaction-restriction fragment length polymorphism (PCR-RFLP) techniques (Table 47).

TABLE 47

Primer sequences, product size, and annealing temperatures

| Gene | Primer sequences (5' to 3') | primer name | Product size (bp) | Annealing temperature (° C.) | Restriction Enzyme | |
|---|---|---|---|---|---|---|
| CD95 | F CTA CCT AAG AGC TAT CTA CCG TTC | CD95F | 232 | 65.0 | Mva I | (SEQ ID NO: 197) |
| (A-670G) | R GGC TGT CCA TGT TGT GGC TGC | CD95R | | | | (SEQ ID NO: 198) |

Results

As shown in Table 48, the polymorphism of A-670G in CD95 is associated with glaucoma, especially POAG.

TABLE 48

Genotype distribution and allele frequency of CD95 gene polymorphisms in glaucoma patients and controls CD95 A-670G

| | Genotype Frequency | | | | | | | | | | Allele frequency | | |
|---|---|---|---|---|---|---|---|---|---|---|---|---|---|
| | A/A | A/G | G/G | p | A/A | A/G + G/G | p | A/A + A/G | G/G | p | A | G | p |
| CONTROL | 60 | 113 | 68 | | 60 | 181 | | 173 | 68 | | 233 | 249 | |
| 241 | 24.9 | 46.9 | 28.2 | | 24.9 | 75.1 | | 71.8 | 28.2 | | 48.3 | 51.7 | |
| NTG | 69 | 145 | 76 | 0.769 | 69 | 221 | 0.768 | 214 | 76 | 0.604 | 283 | 297 | 0.883 |
| 290 | 23.8 | 50.0 | 26.2 | | 23.8 | 76.2 | | 73.8 | 26.2 | | 48.8 | 51.2 | |
| POAG | 45 | 125 | 41 | 0.024 | 45 | 166 | 0.370 | 170 | 41 | 0.029 | 215 | 207 | 0.434 |
| 211 | 21.3 | 59.2 | 19.4 | | 21.3 | 78.7 | | 80.6 | 19.4 | | 50.9 | 49.1 | |

EXAMPLE 16

Evaluation of the EPHX1 Gene in the Etiology of Glaucoma

Association between glaucoma and gene polymorphism of EPHX1 was examined among POAG, NTG patients and control subject using Invader assay.

The primary probes (wild and mutant probes) and Invader® oligonucleotides (Invader® probe) used to detect the polymorphism of ECE1 gene are shown in Table 49.

TABLE 49

The oligonucleotide sequence of

| Mutation | nucleotide change | Target | Probe | Sequence | Length | Tm | Dye | |
|---|---|---|---|---|---|---|---|---|
| EPHX1 K119 | G to A | Sense | Wild | Flap sequence-CTTAGTCTTGAAGTGAGGG | 29 | 62.7 | FAM | (SEQ ID NO: 199) |
| | | | Mutant | Flap sequence-TTTAGTCTTGAAGTGAGGG | 31 | 62.3 | RED | (SEQ ID NO: 200) |
| | | | Invader | TCTCTGGCTGGCGTTTTGGCAAACATACCTTCAATA | 35 | | | (SEQ ID NO: 201) |

Results

As shown in Table 50, the polymorphism of G>A in codon 119 Lys is associated with glaucoma, especially NTG.

TABLE 50

Genotype distribution and allele frequency of EPHX1 gene polymorphisms in glaucoma patients and controls EPHX1 G > A (Lys119Lys)

| | Genotype Frequency | | | | | | | | | | Allele frequency | | |
|---|---|---|---|---|---|---|---|---|---|---|---|---|---|
| | G/G | G/A | A/A | p | G/G | G/A + A/A | p | G/G + G/A | A/A | p | G | A | p |
| CONTROL | 107 | 87 | 30 | | 107 | 117 | | 194 | 30 | | 301 | 147 | |
| 224 | 47.8 | 38.8 | 13.4 | | 47.8 | 52.2 | | 86.6 | 13.4 | | 67.2 | 32.8 | |
| NTG | 121 | 110 | 19 | 0.100 | 121 | 129 | 0.891 | 231 | 19 | 0.039 | 352 | 148 | 0.286 |
| 250 | 48.4 | 44.0 | 7.6 | | 48.4 | 51.6 | | 92.4 | 7.6 | | 70.4 | 29.6 | |
| POAG | 83 | 64 | 29 | 0.669 | 83 | 93 | 0.904 | 147 | 29 | 0.388 | 230 | 122 | 0.583 |
| 176 | 47.2 | 36.4 | 16.5 | | 47.2 | 52.8 | | 83.5 | 16.5 | | 65.3 | 34.7 | |

Partial nucleotide sequence of EPHX1 comprising the targeting polymorphisms is as follows:

(SEQ ID NO: 202)

```
                         primer 1
ccagGACTTA  CACCAGAGGA  TCGATAAGTT  CCGTTTCACC
CCACCTTTGG  AGGACAGCTG  CTTCCACTAT  GGCTTCAACT
CCAACTACCT  GAAGAAAGTC  ATCTCCTACT  GGCGGAATGA
                        codon 113 (T/C)
ATTTGACTGG  AAGAAGCAGG  TGGAGATTCT  CAACAGATAC
  codon 119 (G/A)
CCTCACTTCA  AGACTAAGAT  TGAAGgtatg  tttgcaaaac
       primer 2
gccagccaga  gagggatgta  tgtcatgaga  acagccttct
                              primer 3
```

EXAMPLE 17

Evaluation of the β2 Adrenergic Receptor (ADRB2) Gene in the Etiology of Glaucoma Association between glaucoma and gene polymorphism of ADRB2 was examined in open angle glaucoma patients (POAG and NTG patients) using Invader assay.

The primary probes (wild and mutant probes) and Invader® oligonucleotides (Invader® probe) used to detect the polymorphism of ADRB2 gene are shown in Table 51.

TABLE 51

The oligonucleotide sequence of ADRB2

| Gene | Mutation | nucleotide change | Target | Probe | Sequence | Length (bp) | Tm (° C.) | Dye | |
|---|---|---|---|---|---|---|---|---|---|
| ADRB2 | Gln16Arg | G to A | Sense | A | Flap sequence-TATTGGGTGCCAGCA | 27 | 63.8 | RED | (SEQ ID NO: 203) |
| | (G46A) | | | G | Flap sequence-CATTGGGTGCCAGC | 24 | 63.2 | FAM | (SEQ ID NO: 204) |
| | | | | Invader | TCGTGGTCCGGCGCATGGCTTCA | 23 | 77.5 | | (SEQ ID NO: 205) |
| ADRB2 | Gln27Glu | C to G | Anti-Sense | C | Flap sequence-CAAAGGGACGAGGTGT | 26 | 63.8 | RED | (SEQ ID NO: 206) |
| | (C79G) | | | G | Flap sequence-GAAAGGGACGAGGTGT | 30 | 63.4 | FAM | (SEQ ID NO: 207) |
| | | | | Invader | GCCGGACCACGACGTCACGCAGT | 23 | 77.0 | | (SEQ ID NO: 208) |

Results

As shown in Table 52, the polymorphism of Gly16Arg (G46A) of ADRB2 is associated with early onset of POAG.

TABLE 52

Clinical characteristics of glaucoma patients according to genotype of Gln16Arg in the ADRB2 gene
ADRB2 Gly16Alg

| Phenotype | Clinical characteristics | Genotype RR | Genotype RG + GG | P value* |
|---|---|---|---|---|
| OAG | Age at diagnosis (ys) | 57.9 ± 12.7 (n = 100) | 56.3 ± 12.7 (n = 371) | 0.085 |
| | IOP at diagnosis (mmHg) | 20.3 ± 5.8 (n = 90) | 20.8 ± 6.5 (n = 335) | 0.469 |
| | Visual field score at diagnosis | 2.8 ± 0.7 (n = 99) | 2.9 ± 0.8 (n = 375) | 0.508 |
| POAG | Age at diagnosis (ys) | 62.9 ± 12.7 (n = 39) | 56.7 ± 11.7 (n = 162) | <0.001 |
| | IOP at diagnosis (mmHg) | 26.3 ± 4.9 (n = 33) | 26.3 ± 6.0 (n = 147) | 0.973 |
| | Visual field score at diagnosis | 3.0 ± 0.9 (n = 38) | 3.1 ± 0.9 (n = 164) | 0.898 |
| NTG | Age at diagnosis (ys) | 54.7 ± 11.7 (n = 61) | 56.0 ± 13.5 (n = 209) | 0.531 |
| | IOP at diagnosis (mmHg) | 16.8 ± 2.5 (n = 57) | 16.6 ± 2.4 (n = 188) | 0.581 |
| | Visual field score at diagnosis | 2.7 ± 0.5 (n = 61) | 2.8 ± 0.7 (n = 211) | 0.266 |

P value* with Logistic regression analyses

As shown in Table 53, the polymorphism of Gln27Glu (C79G) is associated with high intraocular pressure (IOP) in OAG, especially POAG.

TABLE 53

Clinical characteristics of glaucoma patients according to genotype of Gln27Glu in the ADRB2 gene
ADRB2 Gln27Glu(Q27E)

| | Phenotype Variable | QQ | QE + EE | P value* |
|---|---|---|---|---|
| POAG | Age at diagnosis (ys) | 58.4 ± 12.3 (n = 162) | 56.3 ± 12.2 (n = 30) | 0.272 |
| | IOP at diagnosis (mmHg) | 26.0 ± 5.1 (n = 144) | 28.6 ± 9.1 (n = 28) | 0.038 |
| | Visual field score at diagnosis | 3.1 ± 0.9 (n = 163) | 3.1 ± 0.9 (n = 30) | 0.837 |
| NTG | Age at diagnosis (ys) | 55.6 ± 12.8 (n = 250) | 58.2 ± 12.6 (n = 23) | 0.986 |
| | IOP at diagnosis (mmHg) | 16.6 ± 2.5 (n = 230) | 17.1 ± 2.0 (n = 17) | 0.447 |
| | Visual field score at diagnosis | 2.8 ± 0.7 (n = 251) | 2.8 ± 0.6 (n = 24) | 0.692 |
| OAG | Age at diagnosis (ys) | 56.7 ± 12.7 (n = 412) | 57.1 ± 12.3 (n = 53) | 0.448 |
| | IOP at diagnosis (mmHg) | 20.2 ± 5.9 (n = 374) | 24.2 ± 9.2 (n = 45) | <0.001 |
| | Visual field score at diagnosis | 2.9 ± 0.8 (n = 414) | 2.9 ± 0.8 (n = 54) | 1.000 |

*P value with Logistic regression analyses

Partial nucleotide sequence for ADRB2 gene containing the targeted polymorphisms is as follows:

ADRB2 codon Nos. Gly16Arg (GGA > AGA): Gln27Glu (CAA > GAA) (underlined)

1 gcgcttacct gccagactgc gcgccatggg gcaacccggg aacggcagcg ccttcttgct (SEQ ID NO: 209)

61 ggcacccaat ggaagccatg cgccggacca cgacgtcacg cagcaaaggg acgaggtgtg 121 ggtggtgggc atgggcatcg tcatgtctct catcgtcctg gccatcgtgt ttggcaatgt 181 gctggtcatc acagccattg ccaagttcga gcgtctgcag acggtcacca actacttcat 241 cacttcactg gcctgtgctg atctggtcat gggcctagca gtggtgcdct ttggggccgc 301 ccatattctt atgaaaatgt ggacttttgg caacttctgg tgcgagtttt ggacttccat

The invention claimed is:

1. A method for diagnosing or predicting susceptibility to open angle glaucoma in a human subject, comprising the steps of: i) obtaining a biological sample from the subject, ii) analyzing said sample to determine the presence or absence of a polymorphism in the noelin 2 gene that results in an arginine to glutamine change at amino acid position 144 of the noelin 2 protein; iii) analyzing said sample to determine the presence or absence of a polymorphism in the myocilin gene that results in a phenylalanine to leucine change at amino acid position 369 of the myocilin protein; and iv) making a diagnosis that said subject has, or is susceptible to, open angle glaucoma when said subject has at least one polymorphism selected from the group consisting of a polymorphism that results in a glutamine at amino acid position 144 of the noelin 2 protein and a polymorphism that results in a leucine at amino acid position 369 of the Myocilin protein.

2. The method of claim 1, wherein said method further comprises analyzing said sample for the presence of at least one other genetic polymorphism associated with open angle glaucoma.

3. The method of claim 1, wherein the analyzing comprises at least one technique selected from the group consisting of polymerase chain reaction (PCR), restriction fragment length polymorphism (PCR-RFLP) analysis, polymerase chain reaction followed by single strand conformation polymorphism (PCR-SSCP) analysis, ASO hybridization analysis, direct sequencing analysis, ARMS analysis, DGGE analysis, RNseA cleaving analysis, chemical restriction analysis, DPL analysis, TAQMAN® PCR analysis, INVADER® assay, MALDI-TOF/MS analysis, TDI analysis, single nucleotide extension assay, WAVE assay and a molecular fluorescent detection assay.

4. The method according to claim 1, further comprising analyzing at least one genetic polymorphism selected from the group consisting of:

(1) AAG to AAT substitution at codon 198 of the endothelin-1 gene (Lys198Asn);
(2) −1370T>G polymorphism of the endothelin-1 gene promoter region;
(3) A138 insertion/deletion (A 138I/D) polymorphism in exon 1 of the endothelin-1 gene;
(4) +70C>G polymorphism in 3' non-coding region of the endothelin receptor A gene; (5)+1222C>T polymorphism of the endothelin receptor A gene;
(6) CAC to CAT substitution at codon 323 in exon 6 of the endothelin receptor A gene (His323His);
(7) −231A>G polymorphism of the endothelin receptor A gene promoter region;
(8) CTG to CTA substitution at codon 277 in exon 4 of the endothelin receptor B gene;
(9) 9099C>A polymorphism of the mitochondrial gene;
(10) 9101 T>G polymorphism of the mitochondrial gene;
(11) 9101 T>C polymorphism of the mitochondrial gene;
(12) 9804G>A polymorphism of the mitochondrial gene;
(13) 11778G>A polymorphism of the mitochondrial gene;
(14) −713T>G polymorphism of the angiotensin II type 1 receptor gene promoter region;
(15) 3123C>A polymorphism of the angiotensin II type 2 receptor gene;
(16) CAA to CGA substitution at codon 192 of the paraoxonase 1 gene (Gln192Arg);
(17) TTG to ATG substitution at codon 55 of the paraoxonase 1 gene (Leu55Met);
(18) GGA to CGA substitution at codon 389 of the β1 adrenergic receptor gene (Gly389Arg);
(19) 1402C>T polymorphism of the E-selectin gene;
(20) the combination of polymorphisms of −857C>T of the tumor necrosis factor a gene promoter region and 412G>A of the optineurin gene;
(21) the combination of polymorphisms of −863C>A of the tumor necrosis factor a gene promoter region and 603T>A of the optineurin gene;
(22) CGC to CCC substitution at codon 72 of the TP53 gene (Arg72Pro);
(23) TAC to CAC substitution at codon 113 of the microsomal epoxide hydrasel gene (Tyr113His);
(24) −110A>C polymorphism of the heatshock protein 70-1 gene promoter region;
(25) −338C>A polymorphism of the endothelin converting enzyme gene promoter region;
(26) −670A>G polymorphism of the CD95 gene promoter region;
(27) AAG to AAA substitution at codon 119 of the microsomal epoxide hydrase 1 gene (Lys 119Lys);
(28) GGA to AGA substitution at codon 16 of the β2 adrenergic receptor gene (Gly16Arg); and
(29) CAA to GAA substitution at codon 27 of the β2 adrenergic receptor gene (Gln27Glu).

5. The method according to claim 1, further comprising analyzing genetic polymorphisms selected from the group consisting of: the combination of polymorphisms of −857C>T of the tumor necrosis factor α gene promoter region and 4120>A of the optineurin gene; and the combination of polymorphisms of −863C>A of the tumor necrosis factor α gene promoter region and 603T>A of the optineurin gene.

6. The method according to claim 1, wherein said open angle glaucoma is primary open angle glaucoma or normal tension glaucoma.

7. The method according to claim 1, wherein said open angle glaucoma is primary open angle glaucoma.

8. The method according to claim 1, wherein said open angle glaucoma is normal tension glaucoma.

* * * * *

SEQUENCE LISTING

<160> NUMBER OF SEQ ID NOS: 210

<210> SEQ ID NO 1
<211> LENGTH: 360

-continued

<212> TYPE: DNA
<213> ORGANISM: Homo Sapiens

<400> SEQUENCE: 1
tctaagatta aaaatgccct agcccacttc ttaccacaag gcacacctac acccccttatc 60 cccatactag ttattatcga aaccatcagc ctactcattc aaccaatagc cctggccgta 120
cgcctaaccg ctaacattac tgcaggccac ctactcatgc acctaattgg aagcgccacc 180
ctagcaatat caaccattaa ccttccctct acacttatca tcttcacaat tctaattcta 240
ctgactatcc tagaaatcgc tgtcgcctta atccaagcct acgttttcac acttctagta 300
agcctctacc tgcacgacaa cacataatga cccaccaatc acatgcctat catatagtaa 360

<210> SEQ ID NO 2
<211> LENGTH: 300
<212> TYPE: DNA
<213> ORGANISM: Homo Sapiens

<400> SEQUENCE: 2
actggaaagc acgggtgctg tggtgtactc ggggagcctc tatttccagg gcgctgagtc 60
cagaactgtc ataagatatg agctgaatac cgagacagtg aaggctgaga aggaaatccc 120
tggagctggc taccacggac agttcccgta ttcttggggt ggctacacgg acattgactt 180
ggctgtggat gaagcaggcc tctgggtcat ttacagcacc gatgaggcca aaggtgccat 240
tgtcctctcc aaactgaacc cagagaatct ggaactcgaa caaacctggg agacaaacat 300

<210> SEQ ID NO 3
<211> LENGTH: 540
<212> TYPE: DNA
<213> ORGANISM: Homo Sapiens

<400> SEQUENCE: 3
ttagttccta caatggagtc atgtctggga agaatctagg gtccaatatg agccacatgt 60
caagggccag gtgtgcatca aagacaaagg gtgaagttat gagtcagagg ttggagtcat 120
gtctgggtca aaggccaggg gtcaggcttg gccatggttc catcttgatg cacaggagct 180
gaaggacagg atgacggaac tgttgcccct gagctcggtc ctggagcagt acaaggcaga 240
cacgcggacc attgtacgct tgcgggagga ggtgaggaat ctctccggca gtctggcggc 300
cattcaggag gagatgggtg cctacgggta tgaggacctg cagcaacggg tgatggccct 360
ggaggcccgg ctccacgcct gcgcccagaa gctgggtatg ccttggccct tgaccctgac 420
ccctgatctc tgactgccac acccaactcc agtatcacct gtttgtgcct agaagctgga 480
cacagttttg acctctaact tttaaacctc aacccttgac cttcctacct aaggctacac 540

<210> SEQ ID NO 4
<211> LENGTH: 23
<212> TYPE: DNA
<213> ORGANISM: Artificial Sequence
<220> FEATURE:
<223> OTHER INFORMATION: Synthetic oligonucleotide primer

<400> SEQUENCE: 4
ttgccgtccc aagcaatgga tga 23

<210> SEQ ID NO 5
<211> LENGTH: 23
<212> TYPE: DNA
<213> ORGANISM: Artificial Sequence
<220> FEATURE:
<223> OTHER INFORMATION: Synthetic oligonucleotide primer

<400> SEQUENCE: 5
tctgggaagg gacagaagat gac 23

<210> SEQ ID NO 6
<211> LENGTH: 22
<212> TYPE: DNA
<213> ORGANISM: Artificial Sequence
<220> FEATURE:
<223> OTHER INFORMATION: Synthetic oligonucleotide primer

<400> SEQUENCE: 6
gatcgataag ttccgtttca cc 22

<210> SEQ ID NO 7
<211> LENGTH: 25
<212> TYPE: DNA
<213> ORGANISM: Artificial Sequence
<220> FEATURE:
<223> OTHER INFORMATION: Synthetic oligonucleotide primer

<400> SEQUENCE: 7
tcaatcttag tcttgaagtg aggat 25

<210> SEQ ID NO 8
<211> LENGTH: 600
<212> TYPE: DNA
<213> ORGANISM: Homo Sapiens

<400> SEQUENCE: 8
tgctgggctt tgccatctac tggttcatct cccgggacaa agaggaaact ttgccacttg 60
aagatgggtg gtgggggcca ggcacgaggt ccgcagccag ggaggacgac agcatccgcc 120
ctttcaaggt ggaaacgtca gatgaggaga tccacgactt acaccagagg atcgataagt 180
tccgtttcac cccacctttg gaggacagct gcttccacta tggcttcaac tccaactacc 240
tgaagaaagt catctcctac tggcggaatg aatttgactg gaagaagcag gtggagattc 300
tcaacagata ccctcacttc aagactaaaa ttgaagggct ggacatccac ttcatccacg 360
tgaagccccc ccagctgccc gcaggccata ccccgaagcc cttgctgatg gtgaacggct 420
ggcccggctc tttctacgag ttttataaga tcatcccact cctgactgac cccaagaacc 480
atggcctgag cgatgagcac gtttttgaag tcatctgccc ttccatccct ggctatggct 540
tctcagaggc atcctccaag aaggggttca actcggtggc caccgccagg atcttttaca 600

<210> SEQ ID NO 9
<211> LENGTH: 780
<212> TYPE: DNA
<213> ORGANISM: Homo Sapiens

<400> SEQUENCE: 9
gcaggcccac caccccgacc ccaaccccag ccccctagca gagacctgtg ggaagcgaaa 60
attccatggg actgactttc tgctcttgtc tttcagactt cctgaaaaca acgttctggt 120
aaggacaagg gttgggctgg ggacctggag ggctggggac ctggagggct ggggggctgg 180
ggggctgagg acctggtcct ctgactgctc ttttcaccca tctacagtcc cccttgccgt 240
cccaagcaat ggatgatttg atgctgtccc cggacgatat tgaacaatgg ttcactgaag 300
acccaggtcc agatgaagct cccagaatgc cagaggctgc tccccgcgtg gcccctgcac 360
cagcagctcc tacaccggcg gcccctgcac cagccccctc ctggcccctg tcatcttctg 420
tcccttccca gaaaacctac cagggcagct acggtttccg tctgggcttc ttgcattctg 480
ggacagccaa gtctgtgact tgcacggtca gttgccctga ggggctggct tccatgagac 540
ttcaatgcct ggccgtatcc ccctgcattt cttttgtttg gaactttggg attcctcttc 600 acccttttggc ttcctgtcag tgtttttttta tagtttaccc acttaatgtg tgatctctga 660
ctcctgtccc aaagttgaat attcccccct tgaatttggg cttttatcca tcccatcaca 720
ccctcagcat ctctcctggg gatgcagaac ttttcttttt cttcatccac gtgtattcct 780

<210> SEQ ID NO 10
<211> LENGTH: 19
<212> TYPE: DNA
<213> ORGANISM: Artificial Sequence
<220> FEATURE:
<223> OTHER INFORMATION: Synthetic oligonucleotide primer

<400> SEQUENCE: 10
gccataaaac tcttcacca 19

<210> SEQ ID NO 11
<211> LENGTH: 21
<212> TYPE: DNA
<213> ORGANISM: Artificial Sequence
<220> FEATURE:
<223> OTHER INFORMATION: Synthetic oligonucleotide primer

<400> SEQUENCE: 11
accataaaac tcttcaccaa a 21

<210> SEQ ID NO 12
<211> LENGTH: 31
<212> TYPE: DNA
<213> ORGANISM: Artificial Sequence
<220> FEATURE:
<223> OTHER INFORMATION: Synthetic oligonucleotide primer

<400> SEQUENCE: 12
ccctacgggc tactacaacc cttcgctgac t 31

<210> SEQ ID NO 13
<211> LENGTH: 21
<212> TYPE: DNA
<213> ORGANISM: Artificial Sequence
<220> FEATURE:
<223> OTHER INFORMATION: Synthetic oligonucleotide primer

<400> SEQUENCE: 13
atgataagtg tagagggaag g 21

<210> SEQ ID NO 14
<211> LENGTH: 20
<212> TYPE: DNA
<213> ORGANISM: Artificial Sequence
<220> FEATURE:
<223> OTHER INFORMATION: Synthetic oligonucleotide primer

<400> SEQUENCE: 14
gtgataagtg tagagggaag 20

<210> SEQ ID NO 15
<211> LENGTH: 47
<212> TYPE: DNA
<213> ORGANISM: Artificial Sequence
<220> FEATURE:
<223> OTHER INFORMATION: Synthetic oligonucleotide primer

<400> SEQUENCE: 15
ggcgacagcg atttctagga tagtcagtag aattagaatt gtgaagt 47

<210> SEQ ID NO 16
<211> LENGTH: 14
<212> TYPE: DNA
<213> ORGANISM: Artificial Sequence
<220> FEATURE:
<223> OTHER INFORMATION: Synthetic oligonucleotide primer

<400> SEQUENCE: 16
gccacaggct tcca 14

<210> SEQ ID NO 17
<211> LENGTH: 15
<212> TYPE: DNA
<213> ORGANISM: Artificial Sequence
<220> FEATURE:
<223> OTHER INFORMATION: Synthetic oligonucleotide primer

<400> SEQUENCE: 17
accacaggct tccac 15

<210> SEQ ID NO 18
<211> LENGTH: 38
<212> TYPE: DNA
<213> ORGANISM: Artificial Sequence
<220> FEATURE:
<223> OTHER INFORMATION: Synthetic oligonucleotide primer

<400> SEQUENCE: 18
catttccgac ggcatctacg gctcaacatt ttttgtat 38

<210> SEQ ID NO 19
<211> LENGTH: 21
<212> TYPE: DNA
<213> ORGANISM: Artificial Sequence
<220> FEATURE:
<223> OTHER INFORMATION: Synthetic oligonucleotide primer

<400> SEQUENCE: 19
gcatcataat cctctctcaa g 21

<210> SEQ ID NO 20
<211> LENGTH: 21
<212> TYPE: DNA
<213> ORGANISM: Artificial Sequence
<220> FEATURE:
<223> OTHER INFORMATION: Synthetic oligonucleotide primer

<400> SEQUENCE: 20
acatcataat cctctctcaa g 21

<210> SEQ ID NO 21
<211> LENGTH: 37
<212> TYPE: DNA
<213> ORGANISM: Artificial Sequence
<220> FEATURE:
<223> OTHER INFORMATION: Synthetic oligonucleotide primer

<400> SEQUENCE: 21
gcctagcaaa ctcaaactac gaacgcactc acagtct 37

<210> SEQ ID NO 22
<211> LENGTH: 23
<212> TYPE: DNA
<213> ORGANISM: Artificial Sequence
<220> FEATURE:
<223> OTHER INFORMATION: Synthetic oligonucleotide primer

<400> SEQUENCE: 22
atggttgtct ttggatatac tac 23

<210> SEQ ID NO 23
<211> LENGTH: 22
<212> TYPE: DNA
<213> ORGANISM: Artificial Sequence
<220> FEATURE:
<223> OTHER INFORMATION: Synthetic oligonucleotide primer

<400> SEQUENCE: 23
gtggttgtct ttggatatac ta 22

<210> SEQ ID NO 24
<211> LENGTH: 56
<212> TYPE: DNA
<213> ORGANISM: Artificial Sequence
<220> FEATURE:
<223> OTHER INFORMATION: Synthetic oligonucleotide primer

<400> SEQUENCE: 24
ttttggggga ggttatatgg gtttaatagt ttttttaatt tatttagggg gaatgt 56

<210> SEQ ID NO 25
<211> LENGTH: 19
<212> TYPE: DNA
<213> ORGANISM: Artificial Sequence
<220> FEATURE:
<223> OTHER INFORMATION: Synthetic oligonucleotide primer

<400> SEQUENCE: 25
atttaggggg aatgatggt 19

<210> SEQ ID NO 26
<211> LENGTH: 18
<212> TYPE: DNA
<213> ORGANISM: Artificial Sequence
<220> FEATURE:
<223> OTHER INFORMATION: Synthetic oligonucleotide primer

<400> SEQUENCE: 26
gtttaggggg aatgatgg 18

<210> SEQ ID NO 27
<211> LENGTH: 57
<212> TYPE: DNA
<213> ORGANISM: Artificial Sequence
<220> FEATURE:
<223> OTHER INFORMATION: Synthetic oligonucleotide primer

<400> SEQUENCE: 27
tgttattatt ctgaattttg ggggaggtta tatgggttta atagtttttt taatttt 57

<210> SEQ ID NO 28
<211> LENGTH: 21
<212> TYPE: DNA
<213> ORGANISM: Artificial Sequence
<220> FEATURE:
<223> OTHER INFORMATION: Synthetic oligonucleotide primer

<400> SEQUENCE: 28
cagtcagagg ttcaattcct c 21

-continued

<210> SEQ ID NO 29
<211> LENGTH: 21
<212> TYPE: DNA
<213> ORGANISM: Artificial Sequence
<220> FEATURE:
<223> OTHER INFORMATION: Synthetic oligonucleotide primer

<400> SEQUENCE: 29
tggggagggg ggttcatagt a 21

<210> SEQ ID NO 30
<211> LENGTH: 20
<212> TYPE: DNA
<213> ORGANISM: Artificial Sequence
<220> FEATURE:
<223> OTHER INFORMATION: Synthetic oligonucleotide primer

<400> SEQUENCE: 30
ggcgcagtca ttctcataat 20

<210> SEQ ID NO 31
<211> LENGTH: 20
<212> TYPE: DNA
<213> ORGANISM: Artificial Sequence
<220> FEATURE:
<223> OTHER INFORMATION: Synthetic oligonucleotide primer

<400> SEQUENCE: 31
aagtaggaga gtgatatttg 20

<210> SEQ ID NO 32
<211> LENGTH: 20
<212> TYPE: DNA
<213> ORGANISM: Artificial Sequence
<220> FEATURE:
<223> OTHER INFORMATION: Synthetic oligonucleotide primer

<400> SEQUENCE: 32
gctttgtttc tgttgagtgt 20

<210> SEQ ID NO 33
<211> LENGTH: 20
<212> TYPE: DNA
<213> ORGANISM: Artificial Sequence
<220> FEATURE:
<223> OTHER INFORMATION: Synthetic oligonucleotide primer

<400> SEQUENCE: 33
aaaatgccct agcccacttc 20

<210> SEQ ID NO 34
<211> LENGTH: 20
<212> TYPE: DNA
<213> ORGANISM: Artificial Sequence
<220> FEATURE:
<223> OTHER INFORMATION: Synthetic oligonucleotide primer

<400> SEQUENCE: 34
gtcattatgt gttgtcgtgc 20

<210> SEQ ID NO 35
<211> LENGTH: 20
<212> TYPE: DNA
<213> ORGANISM: Artificial Sequence
<220> FEATURE:
<223> OTHER INFORMATION: Synthetic oligonucleotide primer

<400> SEQUENCE: 35

-continued cacatccgta ttactcgcat 20

<210> SEQ ID NO 36
<211> LENGTH: 20
<212> TYPE: DNA
<213> ORGANISM: Artificial Sequence
<220> FEATURE:
<223> OTHER INFORMATION: Synthetic oligonucleotide primer

<400> SEQUENCE: 36
cggatgaagc agatagtgag 20

<210> SEQ ID NO 37
<211> LENGTH: 360
<212> TYPE: DNA
<213> ORGANISM: Homo Sapiens

<400> SEQUENCE: 37
tctaagatta aaaatgccct agcccacttc ttaccacaag gcacacctac accccttatc 60
cccatactag ttattatcga aaccatcagc ctactcattc aaccaatagc cctggccgta 120
cgcctaaccg ctaacattac tgcaggccac ctactcatgc acctaattgg aagcgccacc 180
ctagcaatat caaccattaa ccttccctct acacttatca tcttcacaat tctaattcta 240
ctgactatcc tagaaatcgc tgtcgcctta atccaagcct acgttttcac acttctagta 300
agcctctacc tgcacgacaa cacataatga cccaccaatc acatgcctat catatagtaa 360

<210> SEQ ID NO 38
<211> LENGTH: 420
<212> TYPE: DNA
<213> ORGANISM: Homo Sapiens

<400> SEQUENCE: 38
taggagggca ctggccccca acaggcatca ccccgctaaa tcccctagaa gtcccactcc 60
taaacacatc cgtattactc gcatcaggag tatcaatcac ctgagctcac catagtctaa 120
tagaaaacaa ccgaaaccaa ataattcaag cactgcttat tacaatttta ctgggtctct 180
attttaccct cctacaagcc tcagagtact tcgagtctcc cttcaccatt tccgacggca 240
tctacggctc aacatttttt gtagccacag gcttccacgg acttcacgtc attattggct 300
caactttcct cactatctgc ttcatccgcc aactaatatt tcactttaca tccaaacatc 360
actttggctt cgaagccgcc gcctgatact ggcattttgt agatgtggtt tgactatttc 420

<210> SEQ ID NO 39
<211> LENGTH: 420
<212> TYPE: DNA
<213> ORGANISM: Homo Sapiens

<400> SEQUENCE: 39
agccctcgta gtaacagcca ttctcatcca aaccccctga agcttcaccg gcgcagtcat 60
tctcataatc gcccacgggc ttacatcctc attactattc tgcctagcaa actcaaacta 120
cgaacgcact cacagtcgca tcataatcct ctctcaagga cttcaaactc tactcccact 180
aatagctttt tgatgacttc tagcaagcct cgctaacctc gccttacccc ccactattaa 240
cctactggga gaactctctg tgctagtaac cacgttctcc tgatcaaata tcactctcct 300
acttacagga ctcaacatac tagtcacagc cctatactcc ctctacatat ttaccacaac 360
acaatggggc tcactcaccc accacattaa caacataaaa ccctcattca cacgagaaaa 420

<210> SEQ ID NO 40
<211> LENGTH: 21
<212> TYPE: DNA
<213> ORGANISM: Artificial Sequence
<220> FEATURE:
<223> OTHER INFORMATION: Synthetic oligonucleotide primer

<400> SEQUENCE: 40
tgaggttcga gtcggccccc t 21

<210> SEQ ID NO 41
<211> LENGTH: 21
<212> TYPE: DNA
<213> ORGANISM: Artificial Sequence
<220> FEATURE:
<223> OTHER INFORMATION: Synthetic oligonucleotide primer

<400> SEQUENCE: 41
tcgccaaaca tggccacaca t 21

<210> SEQ ID NO 42
<211> LENGTH: 24
<212> TYPE: DNA
<213> ORGANISM: Artificial Sequence
<220> FEATURE:
<223> OTHER INFORMATION: Synthetic oligonucleotide primer

<400> SEQUENCE: 42
gccctgcagg tgtctgcagc atgt 24

<210> SEQ ID NO 43
<211> LENGTH: 24
<212> TYPE: DNA
<213> ORGANISM: Artificial Sequence
<220> FEATURE:
<223> OTHER INFORMATION: Synthetic oligonucleotide primer

<400> SEQUENCE: 43
ggatggctct ccccgccttg tctc 24

<210> SEQ ID NO 44
<211> LENGTH: 24
<212> TYPE: DNA
<213> ORGANISM: Artificial Sequence
<220> FEATURE:
<223> OTHER INFORMATION: Synthetic oligonucleotide primer

<400> SEQUENCE: 44
tggcagcaca gcgcccgcca ctac 24

<210> SEQ ID NO 45
<211> LENGTH: 24
<212> TYPE: DNA
<213> ORGANISM: Artificial Sequence
<220> FEATURE:
<223> OTHER INFORMATION: Synthetic oligonucleotide primer

<400> SEQUENCE: 45
tcgccagccc tcccatgccc ataa 24

<210> SEQ ID NO 46
<211> LENGTH: 24
<212> TYPE: DNA
<213> ORGANISM: Artificial Sequence
<220> FEATURE:
<223> OTHER INFORMATION: Synthetic oligonucleotide primer

<400> SEQUENCE: 46
gaggttgagt gacatgttcg aaac 24

<210> SEQ ID NO 47
<211> LENGTH: 24
<212> TYPE: DNA
<213> ORGANISM: Artificial Sequence
<220> FEATURE:
<223> OTHER INFORMATION: Synthetic oligonucleotide primer

<400> SEQUENCE: 47
cgtcatctgt ctaatgcaaa atgt 24

<210> SEQ ID NO 48
<211> LENGTH: 23
<212> TYPE: DNA
<213> ORGANISM: Artificial Sequence
<220> FEATURE:
<223> OTHER INFORMATION: Synthetic oligonucleotide primer

<400> SEQUENCE: 48
cgtgatgtct ttatctggtt ttg 23

<210> SEQ ID NO 49
<211> LENGTH: 24
<212> TYPE: DNA
<213> ORGANISM: Artificial Sequence
<220> FEATURE:
<223> OTHER INFORMATION: Synthetic oligonucleotide primer

<400> SEQUENCE: 49
cgaactttgg taatacagtt gtgg 24

<210> SEQ ID NO 50
<211> LENGTH: 24
<212> TYPE: DNA
<213> ORGANISM: Artificial Sequence
<220> FEATURE:
<223> OTHER INFORMATION: Synthetic oligonucleotide primer

<400> SEQUENCE: 50
aaactacagt caccctactc acct 24

<210> SEQ ID NO 51
<211> LENGTH: 20
<212> TYPE: DNA
<213> ORGANISM: Artificial Sequence
<220> FEATURE:
<223> OTHER INFORMATION: Synthetic oligonucleotide primer

<400> SEQUENCE: 51
ttcttcacaa actcttccaa 20

<210> SEQ ID NO 52
<211> LENGTH: 21
<212> TYPE: DNA
<213> ORGANISM: Artificial Sequence
<220> FEATURE:
<223> OTHER INFORMATION: Synthetic oligonucleotide primer

<400> SEQUENCE: 52
ggattcagat ttctctttga a 21

<210> SEQ ID NO 53
<211> LENGTH: 21
<212> TYPE: DNA
<213> ORGANISM: Artificial Sequence
<220> FEATURE:
<223> OTHER INFORMATION: Synthetic oligonucleotide primer

<400> SEQUENCE: 53
gcataggagt atgatttaat c 21

<210> SEQ ID NO 54
<211> LENGTH: 27
<212> TYPE: DNA
<213> ORGANISM: Artificial Sequence
<220> FEATURE:
<223> OTHER INFORMATION: Synthetic oligonucleotide primer

<400> SEQUENCE: 54
caggagggat gagcaggcag agcacag 27

<210> SEQ ID NO 55
<211> LENGTH: 29
<212> TYPE: DNA
<213> ORGANISM: Artificial Sequence
<220> FEATURE:
<223> OTHER INFORMATION: Synthetic oligonucleotide primer

<400> SEQUENCE: 55
ctcacccagg aacctgctct ggaaacata 29

<210> SEQ ID NO 56
<211> LENGTH: 25
<212> TYPE: DNA
<213> ORGANISM: Artificial Sequence
<220> FEATURE:
<223> OTHER INFORMATION: Synthetic oligonucleotide primer

<400> SEQUENCE: 56
ggaaatgtga gcagatagtg cagtc 25

<210> SEQ ID NO 57
<211> LENGTH: 25
<212> TYPE: DNA
<213> ORGANISM: Artificial Sequence
<220> FEATURE:
<223> OTHER INFORMATION: Synthetic oligonucleotide primer

<400> SEQUENCE: 57
aatccggagc tggagaactc ttgtc 25

<210> SEQ ID NO 58
<211> LENGTH: 360
<212> TYPE: DNA
<213> ORGANISM: Homo Sapiens

<400> SEQUENCE: 58
attactgtaa actacagtca ccctactcac ctatctaaca ttaattgatt tttggtaaac 60
taatctaatc ttgctttctg gcatcaacct cacttgacca tggtgtatag tccctttcat 120
atgttattgg attcaatttg cctacatttt gttgagaatt tttatctata ctcttaagaa 180
atattgatct gtagtctcgt gatgtcttta tctggttttg ttatcagggt gatactggcc 240
tcatagcatg agttgggaga tcatccttac tcttctattt tttggaagag tttgtgaaga 300
attgatatta tttcttcttt aaatatttat tgggttttta aaatacattt ttaaaatgca 360

<210> SEQ ID NO 59
<211> LENGTH: 323
<212> TYPE: DNA
<213> ORGANISM: Homo Sapiens

<400> SEQUENCE: 59
ggattcagat ttctctttga aacatgcttg tgtttcttag tggggtttta tatccatttt 60
tatcaggatt tcctcttgaa ccagaaccag tctttcaact cattgcatca tttacaagac 120
aacattgtaa gagagatgag cacttctaag ttgagtatat tataatagat tagtactgga 180
ttattcaggc tttaggcata tgcttcttta aaaacgctat aaattatatt cctcttgcat 240
ttcacttgag tggaggttta tagttaatct ataactacat attgaatagg gctaggaata 300
tagattaaat catactccta tgc 323

<210> SEQ ID NO 60
<211> LENGTH: 420
<212> TYPE: DNA
<213> ORGANISM: Homo Sapiens

<400> SEQUENCE: 60
gtgtttctta gtggggtttt atatccattt ttatcaggat ttcctcttga accagaacca 60
gtctttcaac tcattgcatc atttacaaga caacattgta agagagatga gcacttctaa 120
gttgagtata ttataataga ttagtactgg attattcagg ctttaggcat atgcttcttt 180
aaaaacgcta taaattatat tcctcttgca tttcacttga gtggaggttt atagttaatc 240
tataactaca tattgaatag ggctaggaat atagattaaa tcatactcct atgctttagc 300
ttatttttac agttatagaa agcaagatgt actataacat agaattgcaa tctataatat 360
ttgtgtgttc actaaactct gaataagcac tttttaaaaa actttctact cattttaatg 420

<210> SEQ ID NO 61
<211> LENGTH: 17
<212> TYPE: DNA
<213> ORGANISM: Artificial Sequence
<220> FEATURE:
<223> OTHER INFORMATION: Synthetic oligonucleotide primer

<400> SEQUENCE: 61
cttgcctttc agcttgg 17

<210> SEQ ID NO 62
<211> LENGTH: 17
<212> TYPE: DNA
<213> ORGANISM: Artificial Sequence
<220> FEATURE:
<223> OTHER INFORMATION: Synthetic oligonucleotide primer

<400> SEQUENCE: 62
attgcctttc agcttgg 17

<210> SEQ ID NO 63
<211> LENGTH: 31
<212> TYPE: DNA
<213> ORGANISM: Artificial Sequence
<220> FEATURE:
<223> OTHER INFORMATION: Synthetic oligonucleotide primer

<400> SEQUENCE: 63
gttgtgggtc acataacgct ctctggaggg t 31

<210> SEQ ID NO 64
<211> LENGTH: 360
<212> TYPE: DNA
<213> ORGANISM: Homo Sapiens

<400> SEQUENCE: 64
ttgaggtttt atcaaagagt tgcggcgggt ggtgaaagtt cacaaccaga ttcaggtttt 60
gtttgtgcca gattctaatt ttacatgttt cttttgccaa agggtgattt ttttaaaata 120
acatttgttt tctcttatct tgctttatta ggtcggagac catgagaaac agcgtcaaat 180
catcttttca tgatcccaag ctgaaaggca agccctccag agagcgttat gtgacccaca 240
accgagcaca ttggtgacag accttcgggg cctgtctgaa gccatagcct ccacggagag 300
ccctgtggcc gactctgcac tctccaccct ggctgggatc agagcaggag catcctctgc 360

<210> SEQ ID NO 65
<211> LENGTH: 24
<212> TYPE: DNA
<213> ORGANISM: Artificial Sequence
<220> FEATURE:
<223> OTHER INFORMATION: Synthetic oligonucleotide primer

<400> SEQUENCE: 65
agcacagcag agctttccag agga 24

<210> SEQ ID NO 66
<211> LENGTH: 19
<212> TYPE: DNA
<213> ORGANISM: Artificial Sequence
<220> FEATURE:
<223> OTHER INFORMATION: Synthetic oligonucleotide primer

<400> SEQUENCE: 66
ctccaggtct aagcgttgg 19

<210> SEQ ID NO 67
<211> LENGTH: 20
<212> TYPE: DNA
<213> ORGANISM: Artificial Sequence
<220> FEATURE:
<223> OTHER INFORMATION: Synthetic oligonucleotide primer

<400> SEQUENCE: 67
caggccatgt cagtcatcca 20

<210> SEQ ID NO 68
<211> LENGTH: 21
<212> TYPE: DNA
<213> ORGANISM: Artificial Sequence
<220> FEATURE:
<223> OTHER INFORMATION: Synthetic oligonucleotide primer

<400> SEQUENCE: 68
tctcattttc ttgccttagt c 21

<210> SEQ ID NO 69
<211> LENGTH: 18
<212> TYPE: DNA
<213> ORGANISM: Artificial Sequence
<220> FEATURE:
<223> OTHER INFORMATION: Synthetic oligonucleotide primer

<400> SEQUENCE: 69
gaaacccaaa ccagagag 18

<210> SEQ ID NO 70
<211> LENGTH: 24
<212> TYPE: DNA
<213> ORGANISM: Artificial Sequence
<220> FEATURE:
<223> OTHER INFORMATION: Synthetic oligonucleotide primer

<400> SEQUENCE: 70
atatcacctg ctgaactcag agtc 24

<210> SEQ ID NO 71
<211> LENGTH: 24
<212> TYPE: DNA
<213> ORGANISM: Artificial Sequence
<220> FEATURE:
<223> OTHER INFORMATION: Synthetic oligonucleotide primer

<400> SEQUENCE: 71
cctcaacata gtcaatcctt gggc 24

<210> SEQ ID NO 72
<211> LENGTH: 24
<212> TYPE: DNA
<213> ORGANISM: Artificial Sequence
<220> FEATURE:
<223> OTHER INFORMATION: Synthetic oligonucleotide primer

<400> SEQUENCE: 72
acatgaataa agaccatgtg ggca 24

<210> SEQ ID NO 73
<211> LENGTH: 24
<212> TYPE: DNA
<213> ORGANISM: Artificial Sequence
<220> FEATURE:
<223> OTHER INFORMATION: Synthetic oligonucleotide primer

<400> SEQUENCE: 73
gattatggat taagtggtgc ttcg 24

<210> SEQ ID NO 74
<211> LENGTH: 20
<212> TYPE: DNA
<213> ORGANISM: Artificial Sequence
<220> FEATURE:
<223> OTHER INFORMATION: Synthetic oligonucleotide primer

<400> SEQUENCE: 74
tgtctcggta ttcagctcat 20

<210> SEQ ID NO 75
<211> LENGTH: 21
<212> TYPE: DNA
<213> ORGANISM: Artificial Sequence
<220> FEATURE:
<223> OTHER INFORMATION: Synthetic oligonucleotide primer

<400> SEQUENCE: 75
catactgcct aggccactgg a 21

<210> SEQ ID NO 76
<211> LENGTH: 20
<212> TYPE: DNA
<213> ORGANISM: Artificial Sequence
<220> FEATURE:
<223> OTHER INFORMATION: Synthetic oligonucleotide primer

<400> SEQUENCE: 76
attggcgact gactgcttac 20

<210> SEQ ID NO 77
<211> LENGTH: 20

<212> TYPE: DNA
<213> ORGANISM: Artificial Sequence
<220> FEATURE:
<223> OTHER INFORMATION: Synthetic oligonucleotide primer

<400> SEQUENCE: 77
gaatctggaa ctcgaacaaa 20

<210> SEQ ID NO 78
<211> LENGTH: 21
<212> TYPE: DNA
<213> ORGANISM: Artificial Sequence
<220> FEATURE:
<223> OTHER INFORMATION: Synthetic oligonucleotide primer

<400> SEQUENCE: 78
ctgagcatct ccttctgcca t 21

<210> SEQ ID NO 79
<211> LENGTH: 300
<212> TYPE: DNA
<213> ORGANISM: Homo Sapiens

<400> SEQUENCE: 79
actggaaagc acgggtgctg tggtgtactc ggggagcctc tatttccagg gcgctgagtc 60
cagaactgtc ataagatatg agctgaatac cgagacagtg aaggctgaga aggaaatccc 120
tggagctggc taccacggac agttcccgta ttcttggggt ggctacacgg acattgactt 180
ggctgtggat gaagcaggcc tctgggtcat ttacagcacc gatgaggcca aaggtgccat 240
tgtcctctcc aaactgaacc cagagaatct ggaactcgaa caaacctggg agacaaacat 300

<210> SEQ ID NO 80
<211> LENGTH: 21
<212> TYPE: DNA
<213> ORGANISM: Artificial Sequence
<220> FEATURE:
<223> OTHER INFORMATION: Synthetic oligonucleotide primer

<400> SEQUENCE: 80
ccagtgggtt tgtgggactc c 21

<210> SEQ ID NO 81
<211> LENGTH: 21
<212> TYPE: DNA
<213> ORGANISM: Artificial Sequence
<220> FEATURE:
<223> OTHER INFORMATION: Synthetic oligonucleotide primer

<400> SEQUENCE: 81
aaagggatgg catttcttgc a 21

<210> SEQ ID NO 82
<211> LENGTH: 23
<212> TYPE: DNA
<213> ORGANISM: Artificial Sequence
<220> FEATURE:
<223> OTHER INFORMATION: Synthetic oligonucleotide primer

<400> SEQUENCE: 82
gtccactttc ctggtgtgtg act 23

<210> SEQ ID NO 83
<211> LENGTH: 18
<212> TYPE: DNA
<213> ORGANISM: Artificial Sequence
<220> FEATURE:
<223> OTHER INFORMATION: Synthetic oligonucleotide primer

<400> SEQUENCE: 83
caacatcaca atggatcg 18

<210> SEQ ID NO 84
<211> LENGTH: 25
<212> TYPE: DNA
<213> ORGANISM: Artificial Sequence
<220> FEATURE:
<223> OTHER INFORMATION: Synthetic oligonucleotide primer

<400> SEQUENCE: 84
agccttagtt tgatctgttc attca 25

<210> SEQ ID NO 85
<211> LENGTH: 23
<212> TYPE: DNA
<213> ORGANISM: Artificial Sequence
<220> FEATURE:
<223> OTHER INFORMATION: Synthetic oligonucleotide primer

<400> SEQUENCE: 85
gtttcatctt tccaggggag gct 23

<210> SEQ ID NO 86
<211> LENGTH: 42
<212> TYPE: DNA
<213> ORGANISM: Artificial Sequence
<220> FEATURE:
<223> OTHER INFORMATION: Synthetic oligonucleotide primer

<400> SEQUENCE: 86
cgcccgccgc cgcccgccgc aatcccttgc atttctgttt tt 42

<210> SEQ ID NO 87
<211> LENGTH: 21
<212> TYPE: DNA
<213> ORGANISM: Artificial Sequence
<220> FEATURE:
<223> OTHER INFORMATION: Synthetic oligonucleotide primer

<400> SEQUENCE: 87
gtgacaagca cccagtgacg a 21

<210> SEQ ID NO 88
<211> LENGTH: 45
<212> TYPE: DNA
<213> ORGANISM: Artificial Sequence
<220> FEATURE:
<223> OTHER INFORMATION: Synthetic oligonucleotide primer

<400> SEQUENCE: 88
cgcccgccgc cgcccgccgc ggttactctc ttcttagtct ttgga 45

<210> SEQ ID NO 89
<211> LENGTH: 25
<212> TYPE: DNA
<213> ORGANISM: Artificial Sequence
<220> FEATURE:
<223> OTHER INFORMATION: Synthetic oligonucleotide primer

<400> SEQUENCE: 89
gggtgaactg tatggtatct taatt 25

<210> SEQ ID NO 90
<211> LENGTH: 45
<212> TYPE: DNA
<213> ORGANISM: Artificial Sequence
<220> FEATURE:
<223> OTHER INFORMATION: Synthetic oligonucleotide primer

<400> SEQUENCE: 90
cgcccgccgc cgcccgccgc gctatttctc ttaaagccaa agaga 45

<210> SEQ ID NO 91
<211> LENGTH: 21
<212> TYPE: DNA
<213> ORGANISM: Artificial Sequence
<220> FEATURE:
<223> OTHER INFORMATION: Synthetic oligonucleotide primer

<400> SEQUENCE: 91
cagtggctgg actactctcg t 21

<210> SEQ ID NO 92
<211> LENGTH: 44
<212> TYPE: DNA
<213> ORGANISM: Artificial Sequence
<220> FEATURE:
<223> OTHER INFORMATION: Synthetic oligonucleotide primer

<400> SEQUENCE: 92
cgcccgccgc cgcccgccgc gtcagatgat aattgtacag atat 44

<210> SEQ ID NO 93
<211> LENGTH: 25
<212> TYPE: DNA
<213> ORGANISM: Artificial Sequence
<220> FEATURE:
<223> OTHER INFORMATION: Synthetic oligonucleotide primer

<400> SEQUENCE: 93
aatgtatatt tcaaaggagg ataaa 25

<210> SEQ ID NO 94
<211> LENGTH: 21
<212> TYPE: DNA
<213> ORGANISM: Artificial Sequence
<220> FEATURE:
<223> OTHER INFORMATION: Synthetic oligonucleotide primer

<400> SEQUENCE: 94
ccactgcgac gtaaaggagc a 21

<210> SEQ ID NO 95
<211> LENGTH: 25
<212> TYPE: DNA
<213> ORGANISM: Artificial Sequence
<220> FEATURE:
<223> OTHER INFORMATION: Synthetic oligonucleotide primer

<400> SEQUENCE: 95
caaatccgaa ttccaatctg tataa 25

<210> SEQ ID NO 96
<211> LENGTH: 44
<212> TYPE: DNA
<213> ORGANISM: Artificial Sequence
<220> FEATURE:
<223> OTHER INFORMATION: Synthetic oligonucleotide primer

<400> SEQUENCE: 96
cgcccgccgc cgcccgccgc ggttgggagg caagactata agtt 44

<210> SEQ ID NO 97
<211> LENGTH: 25
<212> TYPE: DNA
<213> ORGANISM: Artificial Sequence
<220> FEATURE:
<223> OTHER INFORMATION: Synthetic oligonucleotide primer

<400> SEQUENCE: 97
ttctgttcat tactaggcta tggaa 25

<210> SEQ ID NO 98
<211> LENGTH: 24
<212> TYPE: DNA
<213> ORGANISM: Artificial Sequence
<220> FEATURE:
<223> OTHER INFORMATION: Synthetic oligonucleotide primer

<400> SEQUENCE: 98
caggcagaat tatttcaaaa ccat 24

<210> SEQ ID NO 99
<211> LENGTH: 21
<212> TYPE: DNA
<213> ORGANISM: Artificial Sequence
<220> FEATURE:
<223> OTHER INFORMATION: Synthetic oligonucleotide primer

<400> SEQUENCE: 99
cgagaataca gtcagggctg g 21

<210> SEQ ID NO 100
<211> LENGTH: 25
<212> TYPE: DNA
<213> ORGANISM: Artificial Sequence
<220> FEATURE:
<223> OTHER INFORMATION: Synthetic oligonucleotide primer

<400> SEQUENCE: 100
gcactacctc ctcatcgcat aaaca 25

<210> SEQ ID NO 101
<211> LENGTH: 21
<212> TYPE: DNA
<213> ORGANISM: Artificial Sequence
<220> FEATURE:
<223> OTHER INFORMATION: Synthetic oligonucleotide primer

<400> SEQUENCE: 101
ggccatgctg atgtgagctc t 21

<210> SEQ ID NO 102
<211> LENGTH: 43
<212> TYPE: DNA
<213> ORGANISM: Artificial Sequence
<220> FEATURE:
<223> OTHER INFORMATION: Synthetic oligonucleotide primer

<400> SEQUENCE: 102
cgcccgccgc cgcccgccgc ggactgtctg ctcagtgttg tca 43

<210> SEQ ID NO 103
<211> LENGTH: 21
<212> TYPE: DNA
<213> ORGANISM: Artificial Sequence
<220> FEATURE:
<223> OTHER INFORMATION: Synthetic oligonucleotide primer

<400> SEQUENCE: 103
ggtgccttga tttggaatcc a 21

<210> SEQ ID NO 104
<211> LENGTH: 44
<212> TYPE: DNA
<213> ORGANISM: Artificial Sequence
<220> FEATURE:
<223> OTHER INFORMATION: Synthetic oligonucleotide primer

<400> SEQUENCE: 104
cgcccgccgc cgcccgccgc cacaactgcc tgcaaaatgg aact 44

<210> SEQ ID NO 105
<211> LENGTH: 25
<212> TYPE: DNA
<213> ORGANISM: Artificial Sequence
<220> FEATURE:
<223> OTHER INFORMATION: Synthetic oligonucleotide primer

<400> SEQUENCE: 105
gaggcaaaat atttgagtga aaaca 25

<210> SEQ ID NO 106
<211> LENGTH: 23
<212> TYPE: DNA
<213> ORGANISM: Artificial Sequence
<220> FEATURE:
<223> OTHER INFORMATION: Synthetic oligonucleotide primer

<400> SEQUENCE: 106
aggcaatagg ttttgagggc cat 23

<210> SEQ ID NO 107
<211> LENGTH: 21
<212> TYPE: DNA
<213> ORGANISM: Artificial Sequence
<220> FEATURE:
<223> OTHER INFORMATION: Synthetic oligonucleotide primer

<400> SEQUENCE: 107
gtagtgggcc ctgcaccttc t 21

<210> SEQ ID NO 108
<211> LENGTH: 27
<212> TYPE: DNA
<213> ORGANISM: Artificial Sequence
<220> FEATURE:
<223> OTHER INFORMATION: Synthetic oligonucleotide primer

<400> SEQUENCE: 108
aagtcgagta tggggacccc ccgttaa 27

<210> SEQ ID NO 109
<211> LENGTH: 25
<212> TYPE: DNA
<213> ORGANISM: Artificial Sequence
<220> FEATURE:
<223> OTHER INFORMATION: Synthetic oligonucleotide primer

<400> SEQUENCE: 109
ccccagtgtg tggccatatc ttctt 25

-continued

<210> SEQ ID NO 110
<211> LENGTH: 23
<212> TYPE: DNA
<213> ORGANISM: Artificial Sequence
<220> FEATURE:
<223> OTHER INFORMATION: Synthetic oligonucleotide primer

<400> SEQUENCE: 110
gctgagaaga tgaaggaaaa gtc 23

<210> SEQ ID NO 111
<211> LENGTH: 20
<212> TYPE: DNA
<213> ORGANISM: Artificial Sequence
<220> FEATURE:
<223> OTHER INFORMATION: Synthetic oligonucleotide primer

<400> SEQUENCE: 111
cctctacatg gccctgtcct 20

<210> SEQ ID NO 112
<211> LENGTH: 240
<212> TYPE: DNA
<213> ORGANISM: Homo Sapiens

<400> SEQUENCE: 112
caacagtgac ttttccacag gaacttctgc aatgtcccat caacctctca gctgcctcac 60
tgaaaaggag gacagcccca gtgaaagcac aggaaatgga cccccccacc tggcccaccc 120
aaacctggac acgtttaccc cggaggagct gctgcagcag atgaaagagc tcctgaccga 180
gaaccaccag ctgaaaggtg agcagggctg gcccctgtgt gccccattca tcctgggcct 240

<210> SEQ ID NO 113
<211> LENGTH: 2077
<212> TYPE: DNA
<213> ORGANISM: Homo Sapiens

<400> SEQUENCE: 113
atcccggtcg ggagttctct ccaggcggca cgatgccgag gaaacagtga ccctgagcga 60
agccaagccg ggcggcaggt gtggctttga tagctggtgg tgccacttcc tggccttgga 120
tgagccgtac gcctctgtaa acccaacttc ctcacctttg aaacagctgc ctggttcagc 180
attaatgaag attagtcagt gacaggcctg gtgtgctgag tccgcacata gaagaatcaa 240
aaatgtccaa aatgtaactg gagagaaagt gggcaacttt tggagtgact tttccacagg 300
aacttctgca atgtcccatc aacctctcag ctgcctcact gaaaaggagg acagccccag 360
tgaaagcaca ggaaatggac ccccccacct ggcccaccca aacctggaca cgtttacccc 420
ggaggagctg ctgcagcaga tgaaagagct cctgaccgag aaccaccagc tgaaagaagc 480
catgaagcta aataatcaag ccatgaaagg gagatttgag gagctttcgg cctggacaga 540
gaaacagaag gaagaacgcc agtttttga gatacagagc aaagaagcaa aagagcgtct 600
aatggccttg agtcatgaga atgagaaatt gaaggaagag cttggaaaac taaaagggaa 660
atcagaaagg tcatctgagg accccactga tgactccagg cttcccaggg ccgaagcgga 720
gcaggaaaag gaccagctca ggacccaggt ggtgaggcta caagcagaga aggcagacct 780
gttgggcatc gtgtctgaac tgcagctcaa gctgaactcc agcggctcct cagaagattc 840
ctttgttgaa attaggatgg ctgaaggaga agcagaaggg tcagtaaaag aaatcaagca 900
tagtcctggg cccacgagaa cagtctccac tggcacggca ttgtctaaat ataggagcag 960
atctgcagat ggggccaaga attacttcga acatgaggag ttaactgtga gccagctcct 1020

```
gctgtgccta agggaaggga atcagaaggt ggagagactt gaagttgcac tcaaggaggc   1080

caaagaaaga gtttcagatt ttgaaaagaa aacaagtaat cgttctgaga ttgaaaccca   1140

gacagagggg agcacagaga aagagaatga tgaagagaaa ggcccggaga ctgttggaag   1200

cgaagtggaa gcactgaacc tccaggtgac atctctgttt aaggagcttc aagaggctca   1260

tacaaaactc agcgaagctg agctaatgaa gaagagactt caagaaaagt gtcaggccct   1320

tgaaaggaaa aattctgcaa ttccatcaga gttgaatgaa aagcaagagc ttgtttatac   1380

taacaaaaag ttagagctac aagtggaaag catgctatca gaaatcaaaa tggaacaggc   1440

taaaacagag gatgaaaagt ccaaattaac tgtgctacag atgacacaca acaagcttct   1500

tcaagaacat aataatgcat tgaaaacaat tgaggaacta acaagaaaag agtcagaaaa   1560

agtggacagg gcagtgctga aggaactgag tgaaaaactg gaactggcag agaaggctct   1620

ggcttccaaa cagctgcaaa tggatgaaat gaagcaaacc attgccaagc aggaagagga   1680

cctggaaacc atgaccatcc tcagggctca gatggaagtt tactgttctg attttcatgc   1740

tgaaagagca gcgagagaga aaattcatga ggaaaaggag caactggcat tgcagctggc   1800

agttctgctg aaagagaatg atgctttcga agacggaggc aggcagtcct tgatggagat   1860

gcagagtcgt catggggcga gaacaagtga ctctgaccag caggcttacc ttgttcaaag   1920

aggagctgag gacagggact ggcggcaaca gcggaatatt ccgattcatt cctgccccaa   1980

gtgtggagag gttctgcctg acatagacac gttacagatt cacgtgatgg attgcatcat   2040

ttaagtgttg atgtatcacc tccccaaaac tgttggt                            2077
```

```
<210> SEQ ID NO 114
<211> LENGTH: 240
<212> TYPE: DNA
<213> ORGANISM: Homo Sapiens

<400> SEQUENCE: 114

ccacatgtag cggctctgag gaatgggtta caggagacct ctggggagat gtgaccacag     60

caatgggtag gagaatgtcc agggctatga aagtcgagta tggggacccc cccttaacga    120

agacagggcc atgtagaggg ccccagggag tgaaagagcc tccaggacct ccaggtatgg    180

aatacagggg acgtttaaga agatatggcc acacactggg gccctgagaa gtgagagctt    240


<210> SEQ ID NO 115
<211> LENGTH: 18
<212> TYPE: DNA
<213> ORGANISM: Artificial Sequence
<220> FEATURE:
<223> OTHER INFORMATION: Synthetic oligonucleotide primer

<400> SEQUENCE: 115

ttggtggaga acaaacaa                                                   18


<210> SEQ ID NO 116
<211> LENGTH: 17
<212> TYPE: DNA
<213> ORGANISM: Artificial Sequence
<220> FEATURE:
<223> OTHER INFORMATION: Synthetic oligonucleotide primer

<400> SEQUENCE: 116

gtggtggaga acaaaca                                                    17


<210> SEQ ID NO 117
<211> LENGTH: 27
```

-continued

<212> TYPE: DNA
<213> ORGANISM: Artificial Sequence
<220> FEATURE:
<223> OTHER INFORMATION: Synthetic oligonucleotide primer

<400> SEQUENCE: 117
ggtcttactg ggccactgtg agcgctc 27

<210> SEQ ID NO 118
<211> LENGTH: 16
<212> TYPE: DNA
<213> ORGANISM: Artificial Sequence
<220> FEATURE:
<223> OTHER INFORMATION: Synthetic oligonucleotide primer

<400> SEQUENCE: 118
taacggggag aaaagg 16

<210> SEQ ID NO 119
<211> LENGTH: 17
<212> TYPE: DNA
<213> ORGANISM: Artificial Sequence
<220> FEATURE:
<223> OTHER INFORMATION: Synthetic oligonucleotide primer

<400> SEQUENCE: 119
ttaacgggga gaaaagg 17

<210> SEQ ID NO 120
<211> LENGTH: 26
<212> TYPE: DNA
<213> ORGANISM: Artificial Sequence
<220> FEATURE:
<223> OTHER INFORMATION: Synthetic oligonucleotide primer

<400> SEQUENCE: 120
gcgatccttc agcccaagtg cccttc 26

<210> SEQ ID NO 121
<211> LENGTH: 19
<212> TYPE: DNA
<213> ORGANISM: Artificial Sequence
<220> FEATURE:
<223> OTHER INFORMATION: Synthetic oligonucleotide primer

<400> SEQUENCE: 121
gaaaatcatt ttggggagc 19

<210> SEQ ID NO 122
<211> LENGTH: 19
<212> TYPE: DNA
<213> ORGANISM: Artificial Sequence
<220> FEATURE:
<223> OTHER INFORMATION: Synthetic oligonucleotide primer

<400> SEQUENCE: 122
aaaaatcatt ttggggagc 19

<210> SEQ ID NO 123
<211> LENGTH: 44
<212> TYPE: DNA
<213> ORGANISM: Artificial Sequence
<220> FEATURE:
<223> OTHER INFORMATION: Synthetic oligonucleotide primer

<400> SEQUENCE: 123
tgcctctctg agtcaatgta tttaccactt tccctgagaa atct 44

<210> SEQ ID NO 124
<211> LENGTH: 17
<212> TYPE: DNA
<213> ORGANISM: Artificial Sequence
<220> FEATURE:
<223> OTHER INFORMATION: Synthetic oligonucleotide primer

<400> SEQUENCE: 124
cttgcctttc agcttgg 17

<210> SEQ ID NO 125
<211> LENGTH: 17
<212> TYPE: DNA
<213> ORGANISM: Artificial Sequence
<220> FEATURE:
<223> OTHER INFORMATION: Synthetic oligonucleotide primer

<400> SEQUENCE: 125
attgcctttc agcttgg 17

<210> SEQ ID NO 126
<211> LENGTH: 31
<212> TYPE: DNA
<213> ORGANISM: Artificial Sequence
<220> FEATURE:
<223> OTHER INFORMATION: Synthetic oligonucleotide primer

<400> SEQUENCE: 126
gttgtgggtc acataacgct ctctggaggg t 31

<210> SEQ ID NO 127
<211> LENGTH: 14
<212> TYPE: DNA
<213> ORGANISM: Artificial Sequence
<220> FEATURE:
<223> OTHER INFORMATION: Synthetic oligonucleotide primer

<400> SEQUENCE: 127
ctcctgggca ctgc 14

<210> SEQ ID NO 128
<211> LENGTH: 14
<212> TYPE: DNA
<213> ORGANISM: Artificial Sequence
<220> FEATURE:
<223> OTHER INFORMATION: Synthetic oligonucleotide primer

<400> SEQUENCE: 128
ttcctgggca ctgc 14

<210> SEQ ID NO 129
<211> LENGTH: 29
<212> TYPE: DNA
<213> ORGANISM: Artificial Sequence
<220> FEATURE:
<223> OTHER INFORMATION: Synthetic oligonucleotide primer

<400> SEQUENCE: 129
ctgcacagct tccccggctt cagaaaaca 29

<210> SEQ ID NO 130
<211> LENGTH: 23
<212> TYPE: DNA
<213> ORGANISM: Artificial Sequence
<220> FEATURE:
<223> OTHER INFORMATION: Synthetic oligonucleotide primer

<400> SEQUENCE: 130
tttaagccgt atattgaaga aaa 23

<210> SEQ ID NO 131
<211> LENGTH: 23
<212> TYPE: DNA
<213> ORGANISM: Artificial Sequence
<220> FEATURE:
<223> OTHER INFORMATION: Synthetic oligonucleotide primer

<400> SEQUENCE: 131
cttaagccgt atattgaaga aaa 23

<210> SEQ ID NO 132
<211> LENGTH: 40
<212> TYPE: DNA
<213> ORGANISM: Artificial Sequence
<220> FEATURE:
<223> OTHER INFORMATION: Synthetic oligonucleotide primer

<400> SEQUENCE: 132
cttggttgta atttttgctc tttgctggtt ccctcttcaa 40

<210> SEQ ID NO 133
<211> LENGTH: 16
<212> TYPE: DNA
<213> ORGANISM: Artificial Sequence
<220> FEATURE:
<223> OTHER INFORMATION: Synthetic oligonucleotide primer

<400> SEQUENCE: 133
gtcacagttg ccttgt 16

<210> SEQ ID NO 134
<211> LENGTH: 16
<212> TYPE: DNA
<213> ORGANISM: Artificial Sequence
<220> FEATURE:
<223> OTHER INFORMATION: Synthetic oligonucleotide primer

<400> SEQUENCE: 134
ctcacagttg ccttgt 16

<210> SEQ ID NO 135
<211> LENGTH: 31
<212> TYPE: DNA
<213> ORGANISM: Artificial Sequence
<220> FEATURE:
<223> OTHER INFORMATION: Synthetic oligonucleotide primer

<400> SEQUENCE: 135
ggaagaagga tcagagaaga gattcccgga t 31

<210> SEQ ID NO 136
<211> LENGTH: 19
<212> TYPE: DNA
<213> ORGANISM: Artificial Sequence
<220> FEATURE:
<223> OTHER INFORMATION: Synthetic oligonucleotide primer

<400> SEQUENCE: 136
cttggggttt tcagtatga 19

<210> SEQ ID NO 137
<211> LENGTH: 19

<212> TYPE: DNA
<213> ORGANISM: Artificial Sequence
<220> FEATURE:
<223> OTHER INFORMATION: Synthetic oligonucleotide primer

<400> SEQUENCE: 137
tttggggttt tcagtatga 19

<210> SEQ ID NO 138
<211> LENGTH: 38
<212> TYPE: DNA
<213> ORGANISM: Artificial Sequence
<220> FEATURE:
<223> OTHER INFORMATION: Synthetic oligonucleotide primer

<400> SEQUENCE: 138
cccacaaatg ccaccagaac ttaacgattc ttcactta 38

<210> SEQ ID NO 139
<211> LENGTH: 22
<212> TYPE: DNA
<213> ORGANISM: Artificial Sequence
<220> FEATURE:
<223> OTHER INFORMATION: Synthetic oligonucleotide primer

<400> SEQUENCE: 139
attcagtttc tatttctgct tg 22

<210> SEQ ID NO 140
<211> LENGTH: 22
<212> TYPE: DNA
<213> ORGANISM: Artificial Sequence
<220> FEATURE:
<223> OTHER INFORMATION: Synthetic oligonucleotide primer

<400> SEQUENCE: 140
gttcagtttc tatttctgct tg 22

<210> SEQ ID NO 141
<211> LENGTH: 43
<212> TYPE: DNA
<213> ORGANISM: Artificial Sequence
<220> FEATURE:
<223> OTHER INFORMATION: Synthetic oligonucleotide primer

<400> SEQUENCE: 141
ctcatcccta tagttttaca agacagcaaa agattggtgg ctt 43

<210> SEQ ID NO 142
<211> LENGTH: 290
<212> TYPE: DNA
<213> ORGANISM: Homo Sapiens

<400> SEQUENCE: 142
ttgaattcca ccctccatcc ccagaaaaac tggagtaaaa caaaaagagg agatggacaa 60
agtgtgtatt tgatggcatc ccctgggaag agactctaaa tttatcccat aggtcttact 120
gggccactgt gagcgctttg gtggagaaca aacaaaaatt ctgggtgctc agttgtctaa 180
cctgaaaaat gggactagcg gaaaaagcca atgtgttcca tgcacctttt gctttcttta 240
ttaaggcatg atgtcacctg tacagtaact gccctgtgtg tacttcaggg 290

<210> SEQ ID NO 143
<211> LENGTH: 240
<212> TYPE: DNA
<213> ORGANISM: Homo Sapiens

<400> SEQUENCE: 143
ccagctctcc accgccgcgt gcgcctgcag acgctccgct cgctgccttc tctcctggca 60
ggcgctgcct tttctccccg ttaaagggca cttgggctga aggatcgctt tgagatctga 120
ggaacccgca gcgctttgag ggacctgaag ctgtttttct tcgttttcct ttgggttcag 180
tttgaacggg aggtttttga tccctttttt tcagaatgga ttatttgctc atgattttct 240

<210> SEQ ID NO 144
<211> LENGTH: 300
<212> TYPE: DNA
<213> ORGANISM: Homo Sapiens

<400> SEQUENCE: 144
atccagtgga agaaccacga tcaaaacaac cacaacacag accggagcag ccataaggac 60
agcatgaact gaccaccctt agaagcactc ctcggtactc ccataatcct ctcggagaaa 120
aaaatcacaa ggcaactgtg actccgggaa tctcttctct gatccttctt ccttaattca 180
ctcccacacc caagaagaaa tgctttccaa aaccgcaagg gtagactggt ttatccaccc 240
acaacatcta cgaatcgtac ttctttaatt gatctaattt acatattctg cgtgttgtat 300

<210> SEQ ID NO 145
<211> LENGTH: 300
<212> TYPE: DNA
<213> ORGANISM: Homo Sapiens

<400> SEQUENCE: 145
ttaatttttc ttaaaatgtt aactggcagt aagtcttttt tgatcattcc cttttccata 60
taggaaacat aattttgaag tggccagatg agtttatcat gtcagtgaaa aataattacc 120
cacaaatgcc accagaactt aacgattctt cacttcttgg ggttttcagt atgaacctaa 180
ctccccaccc caacatctcc ctcccacatt gtcaccattt caaagggccc acagtgactt 240
ttgctgggca ttttcccaga tgtttacaga ctgtgagtac agcagaaaat cttttactag 300

<210> SEQ ID NO 146
<211> LENGTH: 360
<212> TYPE: DNA
<213> ORGANISM: Homo Sapiens

<400> SEQUENCE: 146
gaggtagagg cagtgtaagc caggctgttc tcctggctct tctttgaatt attctttctc 60
tggtgtctgc tacttcttgg tactgtagtt cttgcatcta gtataaaaac actaaatttg 120
ttgtcctatt tttttctcac tttcctttag cgtcgagaag tggcaaaaac agttttctgc 180
ttggttgtaa tttttgctct ttgctggttc cctcttcatt taagccgtat attgaagaaa 240
actgtgtata acgagatgga caagaaccga tgtgaattac ttaggtatga tcctgtgtac 300
tcgctagaaa attggagttt ctcagatttt catatttata atacttttac aaaaccagct 360

<210> SEQ ID NO 147
<211> LENGTH: 360
<212> TYPE: DNA
<213> ORGANISM: Homo Sapiens

<400> SEQUENCE: 147
ggaggagacg gggaggacag actggaggcg tgttcctccg gagttttctt tttcgtgcga 60
gccctcgcgc gcgcgtacag tcatcccgct ggtctgacga ttgtggagag gcggtggaga 120
ggcttcatcc atcccacccg gtcgtcgccg gggattgggg tcccagcgag acctccccgg 180

-continued gagaagcagt gcccaggagg ttttctgaag ccggggaagc tgtgcagccg aagccgccgc 240
cgcgccggag cccgggacac cggccaccct ccgcgccacc caccctcgcc ggctccggct 300
tcctctggcc caggcgccgc gcggacccgg cagctgtctg cgcacgccga gctccacggt 360

<210> SEQ ID NO 148
<211> LENGTH: 300
<212> TYPE: DNA
<213> ORGANISM: Homo Sapiens

<400> SEQUENCE: 148
taatcattcc ctgatgaatt tttttaagtt taacatttgt tatataagat tttcttacag 60
aggagtatta atcgtaaaaa ttctctcatc cctatagttt tacaagacag caaaagattg 120
gtggctgttc agtttctatt tctgcttgcc attggccatc actgcatttt tttatacact 180
aatgacctgt gaaatgttga gaaagaaaag tggcatgcag attgctttaa atgatcacct 240
aaagcaggta agaaaataca aatatttgat aactcgtggt tgaatttata attatgaata 300

<210> SEQ ID NO 149
<211> LENGTH: 24
<212> TYPE: DNA
<213> ORGANISM: Artificial Sequence
<220> FEATURE:
<223> OTHER INFORMATION: Synthetic oligonucleotide primer

<400> SEQUENCE: 149
ccgcctcttc gtcttcttca actg 24

<210> SEQ ID NO 150
<211> LENGTH: 24
<212> TYPE: DNA
<213> ORGANISM: Artificial Sequence
<220> FEATURE:
<223> OTHER INFORMATION: Synthetic oligonucleotide primer

<400> SEQUENCE: 150
gatagcaggt gaactcgaag ccca 24

<210> SEQ ID NO 151
<211> LENGTH: 300
<212> TYPE: DNA
<213> ORGANISM: Homo Sapiens

<400> SEQUENCE: 151
ttcctggcca acgtggtgaa ggccttccac cgcgagctgg tgcccgaccg cctcttcgtc 60
ttcttcaact ggctgggcta cgccaactcg gccttcaacc ccatcatcta ctgccgcagc 120
cccgacttcc gcaaggcctt ccagggactg ctctgctgcg cgcgcagggc tgcccgccgg 180
cgccacgcga cccacggaga ccggccgcgc gcctcgggct gtctggcccg gcccggaccc 240
ccgccatcgc ccggggccgc ctcggacgac gacgacgacg atgtcgtcgg ggccacgccg 300

<210> SEQ ID NO 152
<211> LENGTH: 20
<212> TYPE: DNA
<213> ORGANISM: Artificial Sequence
<220> FEATURE:
<223> OTHER INFORMATION: Synthetic oligonucleotide primer

<400> SEQUENCE: 152
catggatcaa ctcaacttga 20

<210> SEQ ID NO 153
<211> LENGTH: 21
<212> TYPE: DNA
<213> ORGANISM: Artificial Sequence
<220> FEATURE:
<223> OTHER INFORMATION: Synthetic oligonucleotide primer

<400> SEQUENCE: 153
tatggatcaa ctcaacttga g 21

<210> SEQ ID NO 154
<211> LENGTH: 37
<212> TYPE: DNA
<213> ORGANISM: Artificial Sequence
<220> FEATURE:
<223> OTHER INFORMATION: Synthetic oligonucleotide primer

<400> SEQUENCE: 154
tcttgtgcct tcagctgtga ggagggattt gaattaa 37

<210> SEQ ID NO 155
<211> LENGTH: 600
<212> TYPE: DNA
<213> ORGANISM: Homo Sapiens

<400> SEQUENCE: 155
tgtttttatt ttattttaag ataaaaagaa ctattgaaga gcttgggaac ttggttacct 60
tgggaaacgt attgctggag atgcaaacaa acttctaaag tgctctctcg tgtgttccag 120
ctgtgagatg cgatgctgtc caccagcccc cgaagggttt ggtgaggtgt gctcattccc 180
ctattggaga attcacctac aagtcctctt gtgccttcag ctgtgaggag ggatttgaat 240
tacatggatc aactcaactt gagtgcacat ctcagggaca atggacagaa gaggttcctt 300
cctgccaagg tagaattgag tgcagacttt tttagggtac aggtcaaata cttcataaag 360
tttctgaacc tagattgccc caaaggggtt tggtcctaat ttcctacatg ctgaaaacta 420
agtagcgctt acactttaca ttcattgttg acttttaagc aagttttgga agttttccag 480
tagatttttc tgaaactctg cctgtgtacc taacatttgc agtggtaaaa tgttcaagcc 540
tggcagttcc gggaaagatc aacatgagct gcagtgggga gcccgtgttt ggcactgtgt 600

<210> SEQ ID NO 156
<211> LENGTH: 17
<212> TYPE: DNA
<213> ORGANISM: Artificial Sequence
<220> FEATURE:
<223> OTHER INFORMATION: Synthetic oligonucleotide primer

<400> SEQUENCE: 156
tgtcttcaga gccagtt 17

<210> SEQ ID NO 157
<211> LENGTH: 17
<212> TYPE: DNA
<213> ORGANISM: Artificial Sequence
<220> FEATURE:
<223> OTHER INFORMATION: Synthetic oligonucleotide primer

<400> SEQUENCE: 157
agtcttcaga gccagtt 17

<210> SEQ ID NO 158
<211> LENGTH: 39
<212> TYPE: DNA
<213> ORGANISM: Artificial Sequence
<220> FEATURE:
<223> OTHER INFORMATION: Synthetic oligonucleotide primer

<400> SEQUENCE: 158
agagctaatg aaagccagtc cattaggcag tatctccac 39

<210> SEQ ID NO 159
<211> LENGTH: 20
<212> TYPE: DNA
<213> ORGANISM: Artificial Sequence
<220> FEATURE:
<223> OTHER INFORMATION: Synthetic oligonucleotide primer

<400> SEQUENCE: 159
aatcctggga gatgtatttg 20

<210> SEQ ID NO 160
<211> LENGTH: 20
<212> TYPE: DNA
<213> ORGANISM: Artificial Sequence
<220> FEATURE:
<223> OTHER INFORMATION: Synthetic oligonucleotide primer

<400> SEQUENCE: 160
gatcctggga gatgtatttg 20

<210> SEQ ID NO 161
<211> LENGTH: 49
<212> TYPE: DNA
<213> ORGANISM: Artificial Sequence
<220> FEATURE:
<223> OTHER INFORMATION: Synthetic oligonucleotide primer

<400> SEQUENCE: 161
agcactttta tggcacaaat gatcactatt ttcttgaccc ctacttact 49

<210> SEQ ID NO 162
<211> LENGTH: 14
<212> TYPE: DNA
<213> ORGANISM: Artificial Sequence
<220> FEATURE:
<223> OTHER INFORMATION: Synthetic oligonucleotide primer

<400> SEQUENCE: 162
ccgttgctcc acca 14

<210> SEQ ID NO 163
<211> LENGTH: 14
<212> TYPE: DNA
<213> ORGANISM: Artificial Sequence
<220> FEATURE:
<223> OTHER INFORMATION: Synthetic oligonucleotide primer

<400> SEQUENCE: 163
acgttgctcc acca 14

<210> SEQ ID NO 164
<211> LENGTH: 53
<212> TYPE: DNA
<213> ORGANISM: Artificial Sequence
<220> FEATURE:
<223> OTHER INFORMATION: Synthetic oligonucleotide primer

<400> SEQUENCE: 164
actatcttat tttcttacct gaatctctga tcttcactaa gagtctgaat aat 53

-continued

<210> SEQ ID NO 165
<211> LENGTH: 1020
<212> TYPE: DNA
<213> ORGANISM: Homo Sapiens

<400> SEQUENCE: 165
agagcctcct agcccgtcgg tgtctgcgcc catcgatccc tttgtctatc cccgaccatg 60
gcgaagctga ttgcgctcac cctcttgggg atgggactgg cactcttcag gaaccaccag 120
tcttcttacc aaacacgact taatgctctc cgagaggtac aacccgtaga acttcctaac 180
tgtaatttag ttaaaggaat cgaaactggc tctgaagact tggagatact gcctaatgga 240
ctggctttca ttagctctgg attaaagtat cctggaataa agagcttcaa ccccaacagt 300
cctggaaaaa tacttctgat ggacctgaat gaagaagatc caacagtgtt ggaattgggg 360
atcactggaa gtaaatttga tgtatcttca tttaaccctc atgggattag cacattcaca 420
gatgaagata atgccatgta cctcctggtg gtgaaccatc cagatgccaa gtccacagtg 480
gagttgttta aatttcaaga agaagaaaaa tcgcttttgc atctaaaaac catcagacat 540
aaacttctgc ctaatttgaa tgatattgtt gctgtgggac ctgagcactt ttatggcaca 600
aatgatcact atttcttgga cccctactta caatcctggg agatgtattt gggtttagcg 660
tggtcgtatg ttgtctacta tagtccaagt gaagttcgag tggtggcaga aggatttgat 720
tttgctaatg gaatcaacat ttcacccgat ggcaagtatg tctatatagc tgagttgctg 780
gctcataaga ttcatgtgta tgaaaagcat gctaattgga ctttaactcc attgaagtcc 840
cttgacttta ataccctcgt ggataacata tctgtggatc ctgagacagg agacctttgg 900
gttggatgcc atcccaatgg catgaaaatc ttcttctatg actcagagaa tcctcctgca 960
tcagaggtgc ttcgaatcca gaacattcta acagaagaac ctaaagtgac acaggtttat 1020

<210> SEQ ID NO 166
<211> LENGTH: 20
<212> TYPE: DNA
<213> ORGANISM: Artificial Sequence
<220> FEATURE:
<223> OTHER INFORMATION: Synthetic oligonucleotide primer

<400> SEQUENCE: 166
gcgagaccct cactgggatt 20

<210> SEQ ID NO 167
<211> LENGTH: 20
<212> TYPE: DNA
<213> ORGANISM: Artificial Sequence
<220> FEATURE:
<223> OTHER INFORMATION: Synthetic oligonucleotide primer

<400> SEQUENCE: 167
gcctggagag gagctggatt 20

<210> SEQ ID NO 168
<211> LENGTH: 20
<212> TYPE: DNA
<213> ORGANISM: Artificial Sequence
<220> FEATURE:
<223> OTHER INFORMATION: Synthetic oligonucleotide primer

<400> SEQUENCE: 168
ggttgggatt tggggaagga 20

<210> SEQ ID NO 169
<211> LENGTH: 24

<212> TYPE: DNA
<213> ORGANISM: Artificial Sequence
<220> FEATURE:
<223> OTHER INFORMATION: Synthetic oligonucleotide primer

<400> SEQUENCE: 169
ccagacatga ctccattgta ggaa 24

<210> SEQ ID NO 170
<211> LENGTH: 22
<212> TYPE: DNA
<213> ORGANISM: Artificial Sequence
<220> FEATURE:
<223> OTHER INFORMATION: Synthetic oligonucleotide primer

<400> SEQUENCE: 170
gagtcagagg ttggagtcat gt 22

<210> SEQ ID NO 171
<211> LENGTH: 21
<212> TYPE: DNA
<213> ORGANISM: Artificial Sequence
<220> FEATURE:
<223> OTHER INFORMATION: Synthetic oligonucleotide primer

<400> SEQUENCE: 171
ccgttgctgc aggtcctcat a 21

<210> SEQ ID NO 172
<211> LENGTH: 20
<212> TYPE: DNA
<213> ORGANISM: Artificial Sequence
<220> FEATURE:
<223> OTHER INFORMATION: Synthetic oligonucleotide primer

<400> SEQUENCE: 172
cagacacgcg gaccattgta 20

<210> SEQ ID NO 173
<211> LENGTH: 21
<212> TYPE: DNA
<213> ORGANISM: Artificial Sequence
<220> FEATURE:
<223> OTHER INFORMATION: Synthetic oligonucleotide primer

<400> SEQUENCE: 173
gggtgtggca gtcagagatc a 21

<210> SEQ ID NO 174
<211> LENGTH: 21
<212> TYPE: DNA
<213> ORGANISM: Artificial Sequence
<220> FEATURE:
<223> OTHER INFORMATION: Synthetic oligonucleotide primer

<400> SEQUENCE: 174
cccaacttga tcacagcact t 21

<210> SEQ ID NO 175
<211> LENGTH: 22
<212> TYPE: DNA
<213> ORGANISM: Artificial Sequence
<220> FEATURE:
<223> OTHER INFORMATION: Synthetic oligonucleotide primer

<400> SEQUENCE: 175
ctaggcacct atgggcagtc aa 22

<210> SEQ ID NO 176
<211> LENGTH: 21
<212> TYPE: DNA
<213> ORGANISM: Artificial Sequence
<220> FEATURE:
<223> OTHER INFORMATION: Synthetic oligonucleotide primer

<400> SEQUENCE: 176
ctaatggctg tagctggtgc t 21

<210> SEQ ID NO 177
<211> LENGTH: 22
<212> TYPE: DNA
<213> ORGANISM: Artificial Sequence
<220> FEATURE:
<223> OTHER INFORMATION: Synthetic oligonucleotide primer

<400> SEQUENCE: 177
gtaggggaag gtgttgttgt aa 22

<210> SEQ ID NO 178
<211> LENGTH: 20
<212> TYPE: DNA
<213> ORGANISM: Artificial Sequence
<220> FEATURE:
<223> OTHER INFORMATION: Synthetic oligonucleotide primer

<400> SEQUENCE: 178
ccagagcaac gtggtggtca 20

<210> SEQ ID NO 179
<211> LENGTH: 19
<212> TYPE: DNA
<213> ORGANISM: Artificial Sequence
<220> FEATURE:
<223> OTHER INFORMATION: Synthetic oligonucleotide primer

<400> SEQUENCE: 179
ggtagccggt gtcccagga 19

<210> SEQ ID NO 180
<211> LENGTH: 21
<212> TYPE: DNA
<213> ORGANISM: Artificial Sequence
<220> FEATURE:
<223> OTHER INFORMATION: Synthetic oligonucleotide primer

<400> SEQUENCE: 180
ggctgtgtac accaccaacc a 21

<210> SEQ ID NO 181
<211> LENGTH: 21
<212> TYPE: DNA
<213> ORGANISM: Artificial Sequence
<220> FEATURE:
<223> OTHER INFORMATION: Synthetic oligonucleotide primer

<400> SEQUENCE: 181
ctcgtaactg gacgtgttgg t 21

<210> SEQ ID NO 182
<211> LENGTH: 21
<212> TYPE: DNA
<213> ORGANISM: Artificial Sequence
<220> FEATURE:
<223> OTHER INFORMATION: Synthetic oligonucleotide primer

<400> SEQUENCE: 182
catgatctgc ggtgtgctct a 21

<210> SEQ ID NO 183
<211> LENGTH: 20
<212> TYPE: DNA
<213> ORGANISM: Artificial Sequence
<220> FEATURE:
<223> OTHER INFORMATION: Synthetic oligonucleotide primer

<400> SEQUENCE: 183
gcagcccgag ccacagcatt 20

<210> SEQ ID NO 184
<211> LENGTH: 540
<212> TYPE: DNA
<213> ORGANISM: Homo Sapiens

<400> SEQUENCE: 184
ttagttccta caatggagtc atgtctggga agaatctagg gtccaatatg agccacatgt 60
caagggccag gtgtgcatca aagacaaagg gtgaagttat gagtcagagg ttggagtcat 120
gtctgggtca aaggccaggg gtcaggcttg gccatggttc catcttgatg cacaggagct 180
gaaggacagg atgacggaac tgttgcccct gagctcggtc ctggagcagt acaaggcaga 240
cacgcggacc attgtacgct tgcgggagga ggtgaggaat ctctccggca gtctggcggc 300
cattcaggag gagatgggtg cctacgggta tgaggacctg cagcaacggg tgatggccct 360
ggaggcccgg ctccacgcct gcgcccagaa gctgggtatg ccttggccct tgaccctgac 420
ccctgatctc tgactgccac acccaactcc agtatcacct gtttgtgcct agaagctgga 480
cacagttttg acctctaact tttaaacctc aacccttgac cttcctacct aaggctacac 540

<210> SEQ ID NO 185
<211> LENGTH: 14
<212> TYPE: DNA
<213> ORGANISM: Artificial Sequence
<220> FEATURE:
<223> OTHER INFORMATION: Synthetic oligonucleotide primer

<400> SEQUENCE: 185
ttttcgcctc ccgt 14

<210> SEQ ID NO 186
<211> LENGTH: 14
<212> TYPE: DNA
<213> ORGANISM: Artificial Sequence
<220> FEATURE:
<223> OTHER INFORMATION: Synthetic oligonucleotide primer

<400> SEQUENCE: 186
gtttcgcctc ccgt 14

<210> SEQ ID NO 187
<211> LENGTH: 27
<212> TYPE: DNA
<213> ORGANISM: Artificial Sequence
<220> FEATURE:
<223> OTHER INFORMATION: Synthetic oligonucleotide primer

<400> SEQUENCE: 187
gctgccaggt cgggaatatt ccagggc 27

<210> SEQ ID NO 188
<211> LENGTH: 20
<212> TYPE: DNA
<213> ORGANISM: Artificial Sequence
<220> FEATURE:
<223> OTHER INFORMATION: Synthetic oligonucleotide primer

<400> SEQUENCE: 188
cgccatggag accaacaccc 20

<210> SEQ ID NO 189
<211> LENGTH: 21
<212> TYPE: DNA
<213> ORGANISM: Artificial Sequence
<220> FEATURE:
<223> OTHER INFORMATION: Synthetic oligonucleotide primer

<400> SEQUENCE: 189
gccggttccc tgctctctgt c 21

<210> SEQ ID NO 190
<211> LENGTH: 360
<212> TYPE: DNA
<213> ORGANISM: Homo Sapiens

<400> SEQUENCE: 190
cgccatggag accaacaccc ttcccaccgc cactccccct tcctctcagg gtccctgtcc 60
cctccagtga atcccagaag actctggaga gttctgagca gggggcggca ctctggcctc 120
tgattggtcc aaggaaggct ggggggcagg acgggaggcg aaacccctgg aatattcccg 180
acctggcagc ctcatcgagc tcggtgattg gctcagaagg gaaaaggcgg gtctccgtga 240
cgacttataa aacgccaggg gcaagcggtc cggataacgg ctagcctgag gagctgctgc 300
gacagtccac taccttttc gagagtgact cccgttgtcc caaggcttcc cagagcgaac 360

<210> SEQ ID NO 191
<211> LENGTH: 13
<212> TYPE: DNA
<213> ORGANISM: Artificial Sequence
<220> FEATURE:
<223> OTHER INFORMATION: Synthetic oligonucleotide primer

<400> SEQUENCE: 191
gtggcccaga gca 13

<210> SEQ ID NO 192
<211> LENGTH: 14
<212> TYPE: DNA
<213> ORGANISM: Artificial Sequence
<220> FEATURE:
<223> OTHER INFORMATION: Synthetic oligonucleotide primer

<400> SEQUENCE: 192
ttggcccaga gcaa 14

<210> SEQ ID NO 193
<211> LENGTH: 37
<212> TYPE: DNA
<213> ORGANISM: Artificial Sequence
<220> FEATURE:
<223> OTHER INFORMATION: Synthetic oligonucleotide primer

<400> SEQUENCE: 193
ggcagataac aaaagtatca ggaaggtgcc ctcgatc 37

<210> SEQ ID NO 194
<211> LENGTH: 20
<212> TYPE: DNA
<213> ORGANISM: Artificial Sequence
<220> FEATURE:
<223> OTHER INFORMATION: Synthetic oligonucleotide primer

<400> SEQUENCE: 194
taagtccccc ttcaacaacc 20

<210> SEQ ID NO 195
<211> LENGTH: 23
<212> TYPE: DNA
<213> ORGANISM: Artificial Sequence
<220> FEATURE:
<223> OTHER INFORMATION: Synthetic oligonucleotide primer

<400> SEQUENCE: 195
aagctgaaaa gtacgcataa atg 23

<210> SEQ ID NO 196
<211> LENGTH: 300
<212> TYPE: DNA
<213> ORGANISM: Homo Sapiens

<400> SEQUENCE: 196
ttttgtctgg tctttctagc attaaccccc tagacacacc taaggctgat gccgggggga 60
acctgtcttg attgctctgg gccacatcga gggcaccttc ctgatacttt tgttatctgc 120
cactggggac ccggttgttg aagggggact taagattttc tcgaaggagg ggtcactgtg 180
agggcctttc ctgcctgcta ggggcttcag tttgggggcc cccactcccg actccgggca 240
agggaggggt ccccatctcc cccgggcctc tcgggtcttg gggtctcccc gggaggccgg 300

<210> SEQ ID NO 197
<211> LENGTH: 24
<212> TYPE: DNA
<213> ORGANISM: Artificial Sequence
<220> FEATURE:
<223> OTHER INFORMATION: Synthetic oligonucleotide primer

<400> SEQUENCE: 197
ctacctaaga gctatctacc gttc 24

<210> SEQ ID NO 198
<211> LENGTH: 21
<212> TYPE: DNA
<213> ORGANISM: Artificial Sequence
<220> FEATURE:
<223> OTHER INFORMATION: Synthetic oligonucleotide primer

<400> SEQUENCE: 198
ggctgtccat gttgtggctg c 21

<210> SEQ ID NO 199
<211> LENGTH: 19
<212> TYPE: DNA
<213> ORGANISM: Artificial Sequence
<220> FEATURE:
<223> OTHER INFORMATION: Synthetic oligonucleotide primer

<400> SEQUENCE: 199
cttagtcttg aagtgaggg 19

<210> SEQ ID NO 200
<211> LENGTH: 19

<212> TYPE: DNA
<213> ORGANISM: Artificial Sequence
<220> FEATURE:
<223> OTHER INFORMATION: Synthetic oligonucleotide primer

<400> SEQUENCE: 200
tttagtcttg aagtgaggg 19

<210> SEQ ID NO 201
<211> LENGTH: 35
<212> TYPE: DNA
<213> ORGANISM: Artificial Sequence
<220> FEATURE:
<223> OTHER INFORMATION: Synthetic oligonucleotide primer

<400> SEQUENCE: 201
tctctggctg gcgttttgca aacatacctt caata 35

<210> SEQ ID NO 202
<211> LENGTH: 240
<212> TYPE: DNA
<213> ORGANISM: Homo Sapiens

<400> SEQUENCE: 202
ccaggactta caccagagga tcgataagtt ccgtttcacc ccacctttgg aggacagctg 60
cttccactat ggcttcaact ccaactacct gaagaaagtc atctcctact ggcggaatga 120
atttgactgg aagaagcagg tggagattct caacagatac cctcacttca agactaagat 180
tgaaggtatg tttgcaaaac gccagccaga gagggatata tgtcatgaga acagccttct 240

<210> SEQ ID NO 203
<211> LENGTH: 15
<212> TYPE: DNA
<213> ORGANISM: Artificial Sequence
<220> FEATURE:
<223> OTHER INFORMATION: Synthetic oligonucleotide primer

<400> SEQUENCE: 203
tattgggtgc cagca 15

<210> SEQ ID NO 204
<211> LENGTH: 14
<212> TYPE: DNA
<213> ORGANISM: Artificial Sequence
<220> FEATURE:
<223> OTHER INFORMATION: Synthetic oligonucleotide primer

<400> SEQUENCE: 204
cattgggtgc cagc 14

<210> SEQ ID NO 205
<211> LENGTH: 23
<212> TYPE: DNA
<213> ORGANISM: Artificial Sequence
<220> FEATURE:
<223> OTHER INFORMATION: Synthetic oligonucleotide primer

<400> SEQUENCE: 205
tcgtggtccg gcgcatggct tca 23

<210> SEQ ID NO 206
<211> LENGTH: 16
<212> TYPE: DNA
<213> ORGANISM: Artificial Sequence
<220> FEATURE:
<223> OTHER INFORMATION: Synthetic oligonucleotide primer -continued

<400> SEQUENCE: 206
caaagggacg aggtgt 16

<210> SEQ ID NO 207
<211> LENGTH: 16
<212> TYPE: DNA
<213> ORGANISM: Artificial Sequence
<220> FEATURE:
<223> OTHER INFORMATION: Synthetic oligonucleotide primer

<400> SEQUENCE: 207
gaaagggacg aggtgt 16

<210> SEQ ID NO 208
<211> LENGTH: 23
<212> TYPE: DNA
<213> ORGANISM: Artificial Sequence
<220> FEATURE:
<223> OTHER INFORMATION: Synthetic oligonucleotide primer

<400> SEQUENCE: 208
gccggaccac gacgtcacgc agt 23

<210> SEQ ID NO 209
<211> LENGTH: 360
<212> TYPE: DNA
<213> ORGANISM: Homo Sapiens

<400> SEQUENCE: 209
gcgcttacct gccagactgc gcgccatggg gcaacccggg aacggcagcg ccttcttgct 60
ggcacccaat ggaagccatg cgccggacca cgacgtcacg cagcaaaggg acgaggtgtg 120
ggtggtgggc atgggcatcg tcatgtctct catcgtcctg gccatcgtgt ttggcaatgt 180
gctggtcatc acagccattg ccaagttcga gcgtctgcag acggtcacca actacttcat 240
cacttcactg gcctgtgctg atctggtcat gggcctagca gtggtgccct ttggggccgc 300
ccatattctt atgaaaatgt ggacttttgg caacttctgg tgcgagtttt ggacttccat 360

<210> SEQ ID NO 210
<211> LENGTH: 11
<212> TYPE: DNA
<213> ORGANISM: Homo Sapiens
<220> FEATURE:
<221> NAME/KEY: misc_feature
<222> LOCATION: (5)..(5)
<223> OTHER INFORMATION: n is c or t

<400> SEQUENCE: 210
acagntcccg t 11